US005587311A

United States Patent [19]
Cobon et al.

[11] Patent Number: 5,587,311
[45] Date of Patent: Dec. 24, 1996

[54] DNA ENCODING A CELL MEMBRANE GLYCOPROTEIN OF A TICK GUT

[75] Inventors: Gary S. Cobon, New South Wales, Australia; Joanna T. Moore, Umea, Sweden; Law A. Y. Johnston, Capalaba, Australia; Peter Willadsen, Chapel Hill, Australia; David H. Kemp, Upper Brookfield, Australia; Alagacone Sriskantha, Florey, Australia; George A. Riding, Indooroopilly, Australia; Keith N. Rand, Frenchs Forest, Australia

[73] Assignees: Biotechnology Australia Pty. Ltd., Roseville; Commonwealth Scientific and Industrial Research Organization, Campbell, both of Australia

[21] Appl. No.: 325,071

[22] Filed: Oct. 19, 1994

Related U.S. Application Data

[63] Continuation of Ser. No. 62,109, May 17, 1993, abandoned, which is a continuation-in-part of Ser. No. 926,368, Aug. 7, 1992, abandoned, which is a continuation-in-part of Ser. No. 242,196, filed as PCT/AU87/00401, Nov. 27, 1987, abandoned.

[30] Foreign Application Priority Data

| Nov. 27, 1986 | [AU] | Australia | PH9196 |
| Jun. 19, 1987 | [AU] | Australia | PH2570 |
| Oct. 16, 1987 | [AU] | Australia | PH4912 |

[51] Int. Cl.$^6$ ............... C12N 1/00; C12N 1/15; C12N 1/21; C12N 5/10; C12N 15/12; C12N 15/63
[52] U.S. Cl. ............... 435/240.2; 435/240.1; 435/252.3; 435/252.33; 435/254.11; 435/320.1; 435/254.2; 536/23.5
[58] Field of Search ............... 435/240.1, 252.3, 435/252.33, 172.3, 240.2, 254.11, 254.2, 320.1; 536/23.5

[56] References Cited

U.S. PATENT DOCUMENTS 4,237,224  12/1980  Cohen et al. ............... 435/69.1

FOREIGN PATENT DOCUMENTS

| 16459/83 | 1/1984 | Australia . |
| 45936/85 | 2/1986 | Australia . |
| 59707/86 | 1/1987 | Australia . |
| 2142334 | 1/1985 | United Kingdom . |

OTHER PUBLICATIONS

Allen et al., "Immunization of Guinea Pigs and Cattle Against Ticks", Nature, vol. 280, Aug. 1979, pp. 491–493.
Johnston et al., "Immunization of Cattle Against *Boophilus microplus* Using Extracts Derived from Adult Female Ticks: Effects of Induced Immunity on Tick Populations", Inter. Journ. Parasitology, vol. 16, No. 1, 1984, pp. 27–34.
Brown et al., "Characterization of Tick Antigens Inducing Host Immune Resistance", Journ. Immun., vol. 133, No. 6, Dec. 1984, pp. 3319–3325.
Ackerman et al., "Artifical Immunity to *Dermacentor variabilis* (Acari: Ixodidae): Vaccination Using Tick Antigens$_1$", J. Med. Entomol., vol. 17, No. 5, 1980, pp. 391–397.
McGowan et al., "Success of Tick Feeding on Calves Immunized with *Amblyomma americanum* (Acari: Ixodidae) Extract$_1$", J. Med. Entomol., vol. 18, No. 4, 1981, pp. 328–332.
Stephen K. Wikel, "The Induction of Host Resistance to Tick Infestation with Salivary Gland Antigen", Am. J. Trop. Med. Hyg., vol. 30, No. 1, 1981, pp. 284–288.
Briggs et al., "Molecular Mechanisms of Protein Secretion", Advances in Protein Chemistry, Academic Press, vol. 38, pp. 110–180. (no date supplied).
van Hemert et al., "The Primary Structure of Elongation Factor EF–1 α from the Brine Shrimp Artemia", EMBO Journ. vol. 3, No. 5, 1984, pp. 1109–1113.
P. Willadsen, "Immunological Approaches to the Control of Ticks", Int. J. Parasit., 17:pp. 671–677. 1987.
Per Vretblad, "Purification of Lectins by Biospecific Affinity Chromatography", Biochimica et Biophysica Acta, vol. 434., 1976, pp. 169–176.
Sage et al., "Common Lentil (Lens culinaris) Phytohemagglutinin", Ginsburg. V. Ed., pp. 332–339 Methods in Enzymology 28 (1972).
Stephen K. Wikel, "Tick and Mite Toxicosis and Allergy", Handbook of Natural Toxins, vol. 2, 1984, pp. 371–396.
Stephen A. Wikel, "Immunomodulation of Host Responses to Ectoparasite Infestation–an Overview", Vet., Para., vol. 14, 1984, pp. 321–339.
George et al., "Acquistion and Expression of Resistance by *Bos indicus* and *Bos indicus* x *Bos taurus* Calves to Amblyomma Americanum Infestation", J. Parasit. vol. 71, No. 2, 1985, pp. 174–182.
S. K. Wikel., "Effects of Tick Infestation on the Plaque–Forming Cell Response to a Thymic Dependent Antigen", Ann. Trop. Med. Parasit., vol. 79, No. 2, 1985, pp. 195–198.
S. K. Wilkel, "Resistance to Ixodid Tick Infestation Induced by Administration of Tickl–Tissue Culture Cells", Ann. Trop. Med. Parasit., vol. 79, No. 5, 1985, pp. 513–518.
Wikel et al., "Ixodid–Host Immune Interaction. Identification and Characterization of Relevant Antigens and Tick–Induced Host Immunosuppresion", Vet. Parasit., vol. 20, 1986, pp. 149–174.

(List continued on next page.)

*Primary Examiner*—Charles L. Patterson, Jr.
*Assistant Examiner*—Gabriele E. Bugaisky
*Attorney, Agent, or Firm*—Foley & Lardner

[57] ABSTRACT

The invention relates to antigens derived from ticks and to their purification. It also relates to genes encoding such antigens and to their cloning and expression from recombinant DNA molecules. Further, the invention describes the use of purified antigens and recombinant expression products having similar biological activity to those purified antigens to provide vaccines to protect cattle against tick infestation.

16 Claims, 29 Drawing Sheets

OTHER PUBLICATIONS

Whelen et al., "Dot–Elisa Assessment of Guinea Pig Antibody Responses to Repeated *Dermacentor andersoni* Infestations", J. Parasit. vol. 72, No. 1, 1986, pp. 155–162.

Wikel et al., "Immunological Studies of Ixodid Tick–Host Interaction: Analysis of Immunogens", J. Toxicol. Toxin Rev. vol. 5, No. 2, 1986, pp. 145–160.

Sharp et al., "Chromatography and Generation of Specific Antisera to Synthetic Peptides from a Protective Boophilus Microplus Antigen", J. Chrom., vol. 512, 1990, pp. 189–202.

"Principles of Gene Manipulation", Blackwell Scientific Pibl., 1985, p. 13.

Purification of WGL+ and LL+ Antigens

LANE 1  GF5/6
LANE 4  WGL+   0.2 μg
LANE 5  WGL+   0.8 μg
LANE 6  LL+    0.7 μg
LANE 7  LL+    0.17 μg

LANES 2,3 & 8   BRL MARKERS:
| | |
|---|---|
| MYOSIN H CHAIN | 200,000 D |
| PHOSPHORYLASE B | 97,400 D |
| BOVINE SERUM ALBUMIN | 68,000 D |
| OVALBUMIN | 43,000 D |
| αCHYMOTRYPSINOGEN | 25,700 D |
| βLACTOGLOBULIN | 18,400 D |
| LYSOZYME | 12,300 D |

FIG. 6

```
                                        1
                                        CCGCGACAGCTGCGGTGGTTCGACGCAGTGAG 33                                          63
ATG CGT GGC ATC GCT TTG TTC GTC GCC GCT GTT TCA CTG ATT GTA GAG GGC ACA GCA
Met Arg Gly Ile Ala Leu Phe Val Ala Ala Val Ser Leu Ile Val Glu Gly Thr Ala 93                                         123
GAA TCA TCC ATT TGC TCT GAC TTC GGG AAC GAG TTC TGT CGC AAC GCT GAA TGT GAA
Glu Ser Ser Ile Cys Ser Asp Phe Gly Asn Glu Phe Cys Arg Asn Ala Glu Cys Glu 153                                        183
GTG GTG CCT GGT GCA GAG GAT GAT TTC GTG TGC AAA TGT CCG CGA GAT AAT ATG TAC
Val Val Pro Gly Ala Glu Asp Asp Phe Val Cys Lys Cys Pro Arg Asp Asn Met Tyr 213                                        243
TTC AAT GCT GCT GAA AAG CAA TGC GAA TAT AAA GAC ACG TGC AAG ACA AGG GAG TGC
Phe Asn Ala Ala Glu Lys Gln Cys Glu Tyr Lys Asp Thr Cys Lys Thr Arg Glu Cys 273                                        303
AGC TAT GGA CGT TGC GTT GAA AGT AAC CCG AGC AAG GCT AGC TGC GTC TGC GAA GCA
Ser Tyr Gly Arg Cys Val Glu Ser Asn Pro Ser Lys Ala Ser Cys Val Cys Glu Ala 333                                        363
TCG GAC GAT CTA ACG CTA CAA TGC AAA ATT AAA AAT GAC TAC GCA ACT GAC TGC CGA
Ser Asp Asp Leu Thr Leu Gln Cys Lys Ile Lys Asn Asp Tyr Ala Thr Asp Cys Arg 393                                        423
AAT CGA GGT GGC ACT GCT AAG TTG CGC ACG GAT GGG TTT ATT GGC GCA ACG TGT GAC
Asn Arg Gly Gly Thr Ala Lys Leu Arg Thr Asp Gly Phe Ile Gly Ala Thr Cys Asp 453                                        483
TGT GGT GAA TGG GGT GCG ATG AAC ATG ACC ACC CGG AAC TGT GTC CCT ACC ACG TGT
Cys Gly Glu Trp Gly Ala Met Asn Met Thr Thr Arg Asn Cys Val Pro Thr Thr Cys 513                                        543
CTT CGT CCC GAC TTG ACC TGC AAA GAC CTC TGC GAG AAA AAC CTG CTT CAA AGG GAT
Leu Arg Pro Asp Leu Thr Cys Lys Asp Leu Cys Glu Lys Asn Leu Leu Gln Arg Asp

573
TCT CGT TGT TGC CAG GGG TGG AAC ACA GCA AAC TGT TCA GCC GCT CCT CCA GCT
Ser Arg Cys Cys Gln Gly Trp Asn Thr Ala Asn Cys Ser Ala Ala Pro Pro Ala 603                                        633
GAC TCC TAT TGC TCT CCT GGG AGC CCC AAA GGA CCG GAC GGA CAG TGT ATA AAT GCT
Asp Ser Tyr Cys Ser Pro Gly Ser Pro Lys Gly Pro Asp Gly Gln Cys Ile Asn Ala 663                                        693
TGC AAG ACG AAA GAA GCT GGG TTT GTC TGC AAG CAT GGA TGC AGG TCG ACC GGC AAG
Cys Lys Thr Lys Glu Ala Gly Phe Val Cys Lys Mis Gly Cys Arg Ser Thr Gly Lys 723                                        753
GCG TAC GAG TGC ACG TGC CCG AGT GGC TCT ACC GTC GCC GAA GAT GGC ATT ACC TGC
Ala Tyr Glu Cys Thr Cys Pro Ser Gly Ser Thr Val Ala Glu Asp Gly Ile Thr Cys
```

FIG. 6(1)

```
            783                                           813
AAA AGT ATT TCG CAC ACA GTC AGC TGC ACT GCT GAG CAA AAA CAG ACC TGC CGC CCA
Lys Ser Ile Ser His Thr Val Ser Cys Thr Ala Glu Gln Lys Gln Thr Cys Arg Pro 843                                           873
ACC GAA GAC TGT CGT GTG CAC AAA GGA AGT GTG TTG TGT GAG TGC CCG TGG AAT CAA
Thr Glu Asp Cys Arg Val His Lys Gly Ser Val Leu Cys Glu Cys Pro Trp Asn Gln 903                                           933
CAT CTA GTG GGG GAC ACG TGC ATA AGT GAT TGC GTC GAC AAG AAA TGC CAC GAA GAA
His Leu Val Gly Asp Thr Cys Ile Ser Asp Cys Val Asp Lys Lys Cys His Glu Glu 963                                           993
TTT ATG GAC TGT GGC GTA TAT ATG AAT CGA CAA AGC TGC TAT TGT CCA TGG AAA TCA
Phe Met Asp Cys Gly Val Tyr Met Asn Arg Gln Ser Cys Tyr Cys Pro Trp Lys Ser 1023                                          1053
AGG AAG CCG GGC CCA AAT GTC AAC ATC AAT GAA TGC CTA CTG AAT GAG TAT TAC TAC
Arg Lys Pro Gly Pro Asn Val Asn Ile Asn Glu Cys Leu Leu Asn Glu Tyr Tyr Tyr

1083
ACG GTG TCA TTC ACC CCA AAC ATA TCT TTT GAT TCT GAC CAT TGC AAA TGG TAT
Thr Val Ser Phe Thr Pro Asn Ile Ser Phe Asp Ser Asp His Cys Lys Trp Tyr 1113                                      1143
GAG GAT CGT GTT TTG GAA GCG ATA CGG ACC AGT ATC GGA AAA GAA GTT TTT AAG GTT
Glu Asp Arg Val Leu Glu Ala Ile Arg Thr Ser Ile Gly Lys Glu Val Phe Lys Val 1173                                          1203
GAG ATA CTT AAC TGC ACG CAG GAC ATT AAG GCA AGA CTC ATA GCA GAG AAA CCA CTG
Glu Ile Leu Asn Cys Thr Gln Asp Ile Lys Ala Arg Leu Ile Ala Glu Lys Pro Leu 1233                                          1263
TCA AAA CAC GTG CTC AGG AAA CTA CAA GCA TGC GAG CAT CCA ATC GGC GAA TGG TGC
Ser Lys His Val Leu Arg Lys Leu Gln Ala Cys Glu His Pro Ile Gly Glu Trp Cys 1293                                          1323
ATG ATG TAT CCG AAG TTG CTG ATC AAG AAA AAC TCT GCA ACA GAA ATC GAA GAA GAG
Met Met Tyr Pro Lys Leu Leu Ile Lys Lys Asn Ser Ala Thr Glu Ile Glu Glu Glu 1353                                          1383
AAC CTT TGC GAC AGT CTG CTC AAG GAT CAG GAA GCT GCC TAC AAA GGT CAA AAC AAA
Asn Leu Cys Asp Ser Leu Leu Lys Asp Gln Glu Ala Ala Tyr Lys Gly Gln Asn Lys 1413                                          1443
TGC GTC AAG GTC GAC AAC CTC TTC TGG TTC CAG TGC GCT GAT GGT TAC ACA ACA ACT
Cys Val Lys Val Asp Asn Leu Phe Trp Phe Gln Cys Ala Asp Gly Tyr Thr Thr Thr 1473                                          1503
TAC GAG ATG ACA CGA GGT CGC CTA CGC CGC TCC GTG TGT AAA GCT GGA GTT TCT TGC
Tyr Glu Met Thr Arg Gly Arg Leu Arg Arg Ser Val Cys Lys Ala Gly Val Ser Cys
```

FIG. 6(2)

```
                    1533                                              1563
AAC GAA AAC GAG CAG TCG GAG TGT GCT GAC AAA GGG CAA ATA TTT GTT TAC GAA AAC
Asn Glu Asn Glu Gln Ser Glu Cys Ala Asp Lys Gly Gln Ile Phe Val Tyr Glu Asn

1593
GGC AAA GCG AAT TGC CAA TGC CCA CCA GAC ACT AAA CCT GGG GAG ATT GGC TGC
Gly Lys Ala Asn Cys Gln Cys Pro Pro Asp Thr Lys Pro Gly Glu Ile Gly Cys 1623                                     1653
ATT GAG CGT ACC ACA TGC AAC CCT AAA GAA ATA CAA GAA TGC CAA GAC AAG AAG CTG
Ile Glu Arg Thr Thr Cys Asn Pro Lys Glu Ile Gln Glu Cys Gln Asp Lys Lys Leu 1683                                           1713
GAG TGC GTT TAC AAA AAC CAT AAA GCA GAA TGC GAG TGT CCT GAT GAT CAC GAG TGT
Glu Cys Val Tyr Lys Asn His Lys Ala Glu Cys Glu Cys Pro Asp Asp His Glu Cys 1743                                           1773
TAC AGG GAG CCT GCC AAA GAC TCT TGC AGT GAA GAG GAT AAT GGT AAA TGT CAA AGC
Tyr Arg Glu Pro Ala Lys Asp Ser Cys Ser Glu Glu Asp Asn Gly Lys Cys Gln Ser 1803                                           1833
AGT GGG CAG CGT TGT GTA ATA GAA AAC GGA AAG GCT GTT TGC AAG GAA AAG TCT GAA
Ser Gly Gln Arg Cys Val Ile Glu Asn Gly Lys Ala Val Cys Lys Glu Lys Ser Glu 1863                                           1893
GCA ACA ACA GCT GCG ACT ACA ACA ACG AAA GCG AAA GAC AAG GAT CCA GAT CCT GGA
Ala Thr Thr Ala Ala Thr Thr Thr Thr Lys Ala Lys Asp Lys Asp Pro Asp Pro Gly 1923                                           1953
AAG TCA AGT GCT GCA GCA GTA TCA GCT ACT GGG CTC TTG TTA CTG CTC GCA GCT ACT
Lys Ser Ser Ala Ala Ala Val Ser Ala Thr Gly Leu Leu Leu Leu Leu Ala Ala Thr 1983                                           2013
TCA GTC ACC GCA GCA TCG TTG TAA GGA AGA TGT CCA ACT TGA ATA CGG AAC
Ser Val Thr Ala Ala Ser Leu ***
```

FIG. 7

```
          10         20         30         40         50         60         70
MRGIALFVAA VSLIVEGTAE SSICSDFGNE FCRNAECEVV PGAEDDFVCK CPRDNMYFNA AEKQCEYKDT
                        F 12                          F 9/10

80         90        100        110        120        130        140
CKTRECSYGR CVESNPSKAS CVCEASDDLT LQCKIKNDYA TDCRNRGGTA KLRTDGFIGA TCDCGEWGAM
    F 13

150        160        170        180        190        200        210
NMTTRNCVPT TCLRPDLTCK DLCEKNLLQR DSRCCQGWNT ANCSAAPPAD SYCSPGSPKG PDGQCINACK
                           F 15                                          F 5

220        230        240        250        260        270        280
TKEAGFVCKH GCRSTGKAYE CTCPSGSTVA EDGITCKSIS HTVSCTAEQK QTCRPTEDCR VHKGSVLCEC
   F 4                  F 14                                               F 16

290        300        310        320        330        340        350
PWNQHLVGDT CISDCVDKKC HEEFMDCGVY MNRQSCYCPW KSRKPGPNVN INECLLNEYY YTVSFTPNIS 360        370        380        390        400        410        420
FDSDHCKWYE DRVLEAIRTS IGKEVFKVEI LNCTQDIKAR LIAEKPLSKH VLRKLQACEH PIGEWCMMYP
             F 2                                                        F 3/17

430        440        450        460        470        480        490
KLLIKKNSAT EIEEENLCDS LLKDQEAAYK GQNKCVKVDN LFWFQCADGY TTTYEMTRGR LRRSVCKAGV
                         F 8

500        510        520        530        540        550        560
SCNENEQSEC ADKGQIFVYE NGKANCQCPP DTKPGEIGCI ERTTCNPKEI QECQDKKLEC VYKNHKAECE
   F 6                            F 9/10

570        580        590        600        610        620        630
CPDDHECYRE PAKDSCSEED NGKCQSSGQR CVIENGKAVC KEKSEATTAA TTTTKAKDKD PDPGKSSAAA
                                                                         F 1

640        650        660        670
VSATGLLLLL AATSVTAASL *GRCPT*IRN SLNMYIYITL TSNT*LGF
```

FIG. 8B

| Enzymes which cut 1 times | |
|---|---|
| ApaI | 1007 |
| BamHI | 1889 |
| BanI | 149 |
| BglI | 730 |
| FspI | 397 |
| HaeIII | 1008 |
| NcoI | 987 |
| NheI | 297 |
| PstI | 1915 |
| SphI | 1251 |
| SplI | 715 |
| SspI | 1547 |
| StyI | 987 |
| XmnI | 116 |

| Enzymes which cut 2 times | | |
|---|---|---|
| ApaLI | 722 | 843 |
| AvaI | 287 | 731 |
| AvaII | 630 | 1135 |
| BclI | 1300 | 1721 |
| BsmI | 693 | 1259 |
| FnuDII | 2 | 187 |
| NciI | 463 | 1005 |
| Nsp7534I | 1251 | 1632 |
| XhoII | 1889 | 1895 |

| Enzymes which cut 3 times | | | |
|---|---|---|---|
| AccI | 701 | 918 | 1404 |
| BanII | 620 | 1007 | 1935 |
| DdeI | 391 | 802 | 1236 |
| HgiAI | 722 | 843 | 1233 |
| HhaI | 398 | 418 | 1429 |
| HphI | 435 | 1066 | 1966 |
| MaeI | 298 | 888 | 2054 |
| RsaI | 200 | 716 | 1627 |
| SalI | 701 | 918 | 1404 |

| Enzymes which cut 4 times | | | | |
|---|---|---|---|---|
| HgaI | 22 | 304 | 916 | 1396 |
| HindII | 701 | 918 | 1017 | 1404 |
| HpaII | 464 | 633 | 706 | 1005 |
| PvuII | 7 | 595 | 791 | 1855 |
| Sau96I | 630 | 1007 | 1008 | 1135 |

| Enzymes which cut 5 times | | | | | |
|---|---|---|---|---|---|
| BinI | 1112 | 1361 | 1889 | 1890 | 1896 |
| BspMI | 504 | 529 | 697 | 765 | 816 |
| EcoRII | 153 | 557 | 615 | 1602 | 1899 |
| FokI | 94 | 164 | 404 | 693 | 1260 |
| TthIIII | 653 | 686 | 1072 | 1248 | 1826 |

| Enzymes which cut 6 times | | | | | | |
|---|---|---|---|---|---|---|
| MaeIII | 283 | 427 | 1438 | 1732 | 1943 | 1965 |
| NlaIII | 455 | 690 | 988 | 1252 | 1280 | 1633 |
| NlaIV | 149 | 619 | 1007 | 1420 | 1739 | 1889 |
| SfaNI | 32 | 40 | 315 | 694 | 1259 | 1974 |

GEL A    COOMASSIE STAIN
GEL B    WESTERN TRANSFER

LANE 1: BRL HIGH MOLECULAR WEIGHT MARKERS
      2,4: BTA LYSATE UNINDUCED
      3,5: BTA LYSATE INDUCED WITH IPTG 1 2 3 4     5 6 7      8 9

27,300 bp 930
630
340

A: SOUTHERN BLOT GENOMIC DNA Sau3A DIGEST
B: STAINED GEL
C: SOUTHERN BLOT

LANE: 1 B. MICROPLUS         LANE: 5 LAMBDA HindIII
      2 B. DECOLORATUS              6,8 B. DECOLORATUS CLONE HaeIII DIGEST
      3 R. APPENDICULATUS           7,9 B. DECOLORATUS CLONE ApaI DIGEST
      4 A. VARIAGATUM

FIG. 11

```
GAA TTC GCG GCC AAA GTG CGA CAG CTG CGG TGG GAC GCA GTC GAG ATG CGT GGC ATC GCT TTG TTC GTC    75
                                                        Met Arg Gly Ile Ala Leu Phe Val

GCC GTT TCA CTG ATT GTA GAG GGC ACA GCA GAA TCA TCC ATT TGC TCT GAC TTC GGG AAC GAG TTC CGC   150
Ala Val Ser Leu Ile Val Glu Gly Thr Ala Glu Ser Ser Ile Cys Ser Asp Phe Gly Asn Glu Phe Cys Arg

AAC GCT GAA TGT GAA AAG GTG GTG CCT GGT GCA GAG GAT GAT TTC GTG TGC AAA GAT CGA AAT ATG TAC TTC   225
Asn Ala Glu Cys Glu Lys Val Val Pro Gly Ala Glu Asp Asp Phe Val Cys Lys Asp Arg Asn Met Tyr Phe

AAT GCT GAA AAG CAA TAT AAA GAC ACG AGG GAG TGC ACG AGC TAT GGA CGT TGC GTT GAA   300
Asn Ala Glu Lys Gln Tyr Lys Asp Thr Arg Glu Cys Thr Ser Tyr Gly Arg Cys Val Glu

AGT GCT GAA AAG GTC TGC GAA GCA TCG TGC GAT CTA ACG CTA CAA TGC AAA ATT AAA AAT GAC   375
Ser Ala Glu Lys Val Cys Glu Ala Ser Cys Asp Leu Thr Leu Gln Cys Lys Ile Lys Asn Asp

TAC GCA ACT GAC TGC CGA AAC ATG ACT GCT GGT GGC GAT TTG ATT GGC GCA ACG TGT GAC   450
Tyr Ala Thr Asp Cys Arg Asn Met Thr Ala Gly Gly Asp Leu Ile Gly Ala Thr Cys Asp

TGT GGT GAA TGG GGT GCG GAG AAA AAC CGG ACC ACG TGT CTT CGT CCC GAC TTG AGC   525
Cys Gly Glu Trp Gly Ala Glu Lys Asn Arg Thr Thr Cys Leu Arg Pro Asp Leu Ser

TGC AAA GAC CTC TGC GAG CTC TGC CTT CAA AGG GAT TGT TGC CAG GGG TGG AAC ACA GCA AAC TGT   600
Cys Lys Asp Leu Cys Glu Leu Cys Leu Gln Arg Asp Cys Cys Gln Gly Trp Asn Thr Ala Asn Cys

TCA GCC GCT CCA GCT GAC TCC TAT TGC TCT CCT GGG AGC CCC AAA GGA GAC CAG TGT ATA AAT GCT   675
Ser Ala Ala Pro Ala Asp Ser Tyr Cys Ser Pro Gly Ser Pro Lys Gly Asp Gln Cys Ile Asn Ala

TGC AAG ATG AAA GAA GCT GGT GTC TTT GTC CAT GGA TGC AAG TCG ACC GCC TAC GCG TGG ACG TGC   750
Cys Lys Met Lys Glu Ala Gly Val Phe Val His Gly Cys Lys Ser Thr Ala Tyr Ala Trp Thr Cys

CCA CGT GCC TTT ACC GTC GCG GAT GCG GAA GAT GGC ATT ACC ACA AGT ATT TCG AGC TGC ACT GCT GAG   825
Pro Arg Ala Phe Thr Val Ala Asp Ala Glu Asp Gly Ile Thr Thr Ser Ile Ser Ser Cys Thr Ala Glu

CAA AAA CAG ACC TGC CCA CGC GTG CAC GTG ACT CGT CGT TGT TGT CCG TGG AAT   900
Gln Lys Gln Thr Cys Pro Arg Val His Val Thr Cys Arg Val Leu Cys Cys Pro Trp Asn

CAA CAT CTA GTG GGG GAC ACG TGC ATA AGT GAC GAC TGC CAC GAA GAA AAG AAG AAC TGC CAC GAA TTT ATG GAC TGT GGC   975
Gln His Leu Val Gly Asp Thr Cys Ile Ser Asp Asp Cys His Glu Glu Lys Lys Asn Cys His Glu Phe Met Asp Cys Gly
```

FIG. II(1)

| | | | | | | | | | | |
|---|---|---|---|---|---|---|---|---|---|---|
| GTA Val | TAT Tyr | ATG Met | AAT Asn | CGA Arg | CAA Gln | AGC Ser | TGC Cys | TAT Tyr | TGT Cys | CCA Pro | TGG Trp | AAA Lys | TCA Ser | AGG Arg | AAG Lys | CCG Pro | GGC Gly | CCA Pro | AAT Asn | GTC Val | AAC Asn | ATC Ile | AAT Asn | GGA Gly | 1050 |
| TGC Cys | CTA Leu | AAT Asn | GAG Glu | CTG Leu | TAT Tyr | TAC Tyr | ACG Thr | GTG Val | TCA Ser | TTC Phe | ACC Thr | CCA Pro | AAC Asn | ATA Ile | TCT Ser | GAT Asp | CAT His | TGC Cys | AAA Lys | 1125 |
| TAT Tyr | GAG Glu | GAT Asp | CGT Arg | GTT Val | TTG Leu | GAA Glu | GCG Ala | ATA Ile | CGG Arg | ACC Thr | AGT Ser | ATC Ile | GGA Gly | AAG Lys | GAA Glu | GTT Val | TTT Phe | AAG Lys | GTT Val | GAG Glu | ATA Ile | CTT Leu | AAC Asn | TGC Cys | 1200 |
| ACG Thr | CAG Gln | GAC Asp | ATT Ile | AAG Lys | GCA Ala | CTC Leu | ATA Ile | GCA Ala | AGA Arg | CTG Leu | TTA Leu | TCA Ser | AAA Lys | CAC His | GTG Val | CTC Leu | AGG Arg | AAA Lys | CTA Leu | CAA Gln | TGC Cys | 1275 |
| GAG Glu | CAT His | CCA Pro | ATC Ile | GGC Gly | GAA Glu | ATG Met | TGC Cys | ATG Met | TAT Tyr | CCG Pro | AAG Lys | ATC Ile | ATC Ile | AAG Lys | AAC Asn | TCT Ser | GCA Ala | ACA Thr | GAA Glu | ATC Ile | 1350 |
| GAA Glu | GAG Glu | AAC Asn | CTT Leu | TGC Cys | AGT Ser | GAC Asp | CTG Leu | CTC Leu | AAG Lys | GAT Asp | CAG Gln | GCA Ala | GCT Ala | CAA Gln | GCT Ala | TAC Tyr | CAA Gln | AAC Asn | AAA Lys | GGT Gly | CAA Gln | AAC Asn | AAG Lys | GTC Val | 1425 |
| GAC Asp | AAC Asn | CTC Leu | TTC Phe | TGG Trp | TTC Phe | CAG Gln | GTT Val | GCT Ala | GAT Asp | GGT Gly | GAT Asp | TAC Tyr | ACA Thr | ACA Thr | ACT Thr | GAG Glu | ATG Met | ACA Thr | CGA Arg | GGT Gly | CTA Leu | CGC Arg | CGC Arg | 1500 |
| TCC Ser | GTG Val | TGT Cys | AAA Lys | GCT Ala | GGA Gly | GTT Val | TCT Ser | TGC Cys | AAT Asn | GAA Glu | GAG Glu | CAG Gln | TCG Ser | GAG Glu | TGT Cys | GAG Glu | AAA Lys | GGG Gly | CAA Gln | ATA Ile | TGT Cys | GTT Val | 1575 |
| TAC Tyr | GAA Glu | AAC Asn | GGC Gly | AAA Lys | GCG Ala | AAT Asn | TGC Cys | CAA Gln | GAA Glu | TGC Cys | CCA Pro | CCA Pro | GAC Asp | ACT Thr | AAA Lys | CCT Pro | AAG Lys | GAG Glu | ATT Ile | GGC Gly | CTA Leu | ATT Ile | GAG Glu | ACC Thr | 1650 |
| ACA Thr | TGC Cys | AAC Asn | CCT Pro | AAA Lys | GAG Glu | CAA Gln | ATA Ile | CAA Gln | GAA Glu | AAG Lys | CTG Leu | AAG Lys | GAG Glu | TGC Cys | TGC Cys | GAG Glu | GTT Val | TAC Tyr | TAC Tyr | AAC Asn | CAT His | AAA Lys | GCA Ala | GAA Glu | 1725 |
| TSS Xaa | AAG Lys | TGT Cys | CCT Pro | GAT Asp | CAC His | GAG Glu | TGT Cys | ACC Thr | TGC Cys | AGG Arg | TAC Tyr | GCC Ala | AAA Lys | GAG Glu | CCT Pro | GAA Glu | GAT Asp | GAT Asp | GAG Glu | AAG Lys | AAT Asn | GGT Gly | AAA Lys | 1800 |
| TGT Cys | CAA Gln | AGC Ser | AGT Ser | CGT Arg | CAG Gln | CAG Gln | TGT Cys | GTA Val | ATA Ile | GAA Glu | GAC Asp | AAG Lys | CCA Pro | GGT Gly | GTT Val | GCT Ala | AAG Lys | TCT Ser | GAA Glu | GAA Glu | GCA Ala | ACA Thr | ACA Thr | 1875 |
| GCT Ala | GCG Ala | ACT Thr | ACA Thr | ACG Thr | AAA Lys | GCA Ala | ACG Thr | AAG Lys | GAC Asp | GAT Asp | CCT Pro | GGA Gly | AAG Lys | GAC Asp | CCT Pro | GAT Asp | CCA Pro | GAT Asp | CCA Pro | GAT Asp | GGA Gly | GGA Gly | GTA Val | TCA Ser | GCT Ala | 1950 |

FIG. 11(2)

```
ACT GGG CTC TTG TTA CTG CTC GCA GCT ACT TCA GTC ACC GCA GCA TCG TTG TAA GGA AGA TGT CCA ACT TGA ATA 2025
Thr Gly Leu Leu Leu Leu Leu Ala Ala Thr Ser Val Thr Ala Ala Ser Leu

CGG AAC AGC TTG AAT ATG TAT ATA ACG CTT ACA TCG AAC ACC TAG CTT GGT TTT TGG AAT TTC AAT ATT 2100

GCG CAT TGG TAC TCA CGG CAA CAT GAA TGT ATT ACT TTA GAA TGA CAG GGA AGA GGG ACG TGA AAG GAG TTT CCT 2175

TGT CTG AAC ATA TCA AAG AAA ATT TTC CCC TAT CCG ACC GAT GTC AAA TAA AGA TAG TTG GGT CTA AAC AGC GGC 2250

CGC GAA TTC                                                                                       2259
```

FIG. 12

```
GTT  GAA  AGT  AAC  CCG  AGC  AAG  GCT  AGC  TGC  GTC  TGC  GAA  CGA  TCG  GAC  GAT  CTA  CAA  TGC  AAA  ATT  AAA      75
Val  Glu  Ser  Asn  Pro  Ser  Lys  Ala  Ser  Cys  Val  Cys  Glu  Arg  Ser  Asp  Asp  Leu  Gln  Cys  Lys  Ile  Lys

AAT  GAC  GCA  TAC  GCA  ACT  GAC  TGC  CGA  AAT  CGA  AAT  GCT  GCT  AAG  ACG  CTA  CAA  TTT  ATT  GGC  GCA  ACG     150
Asn  Asp  Ala  Tyr  Ala  Thr  Asp  Cys  Arg  Asn  Arg  Asn  Ala  Ala  Lys  Thr  Leu  Gln  Phe  Ile  Gly  Ala  Thr

TGC  GAC  TGT  GGT  GAA  GGC  TGG  ATG  GGC  GGT  GGG  ATG  TTG  CGC  ACG  GAT  CTT  CGT  CCC  GAC     225
Cys  Asp  Cys  Gly  Glu  Gly  Trp  Met  Gly  Gly  Gly  Met  Leu  Arg  Thr  Asp  Leu  Arg  Pro  Asp

TTG  ACC  TGC  AAA  GAC  CTC  TGC  GAG  AAA  AAC  CTG  CTT  GTC  AAC  TGT  TGT  CGT  TGG  AAC  ACA  GCA     300
Leu  Thr  Cys  Lys  Asp  Leu  Cys  Glu  Lys  Asn  Leu  Leu  Val  Asn  Cys  Cys  Arg  Trp  Asn  Thr  Ala

AAC  TGT  TCA  GCC  GCT  CCA  GCT  GAC  TCC  TAT  TGC  CAA  AGG  TCT  CGT  CCT  CAG  GGA  CCG  CAG  ATA     375
Asn  Cys  Ser  Ala  Ala  Pro  Ala  Asp  Ser  Tyr  Cys  Gln  Arg  Ser  Arg  Pro  Gln  Gly  Pro  Gln  Ile

AAT  GCT  TCA  AAG  ATG  GAA  GAA  GCT  GGG  TTT  GTC  GGG  AGC  CCC  AAA  GGA  CCG  TAC  CAG  GAG     450
Asn  Ala  Ser  Lys  Met  Glu  Glu  Ala  Gly  Phe  Val  Gly  Ser  Pro  Lys  Gly  Pro  Tyr  Gln  Glu

ACG  TGC  CCA  CGT  GGC  TTT  ACC  GCG  GTC  GAG  GAT  GGG  CAT  GGA  TGC  AAA  AGT  ATT  ACC  CAC  ACA  AGC  ACT     525
Thr  Cys  Pro  Arg  Gly  Phe  Thr  Ala  Val  Glu  Asp  Gly  His  Gly  Cys  Lys  Ser  Ile  Thr  His  Thr  Ser  Thr

GCT  GAG  CAA  CAG  ACC  TGC  CCA  GAA  GAT  GAA  ACC  TGT  GTG  ACT  GTG  TTG  TGT  GAG  TGC  CCG     600
Ala  Glu  Gln  Gln  Thr  Cys  Pro  Glu  Asp  Glu  Thr  Cys  Val  Thr  Val  Leu  Cys  Glu  Cys  Pro

TGG  AAT  CAA  CAT  CTA  ACG  ACG  GGG  GAC  GAC  GAT  GAT  TGC  CAC  CAC  GAA  GAA  AGG  GAA  GAA  ATG  GAC     675
Trp  Asn  Gln  His  Leu  Thr  Thr  Gly  Asp  Asp  Asp  Asp  Cys  His  His  Glu  Glu  Arg  Glu  Glu  Met  Asp

TGT  GGC  GTA  TAT  ATG  CGA  CAA  AGC  AGC  TGC  TGT  CCA  TGG  AAA  TCA  AGG  AAG  CCG  GGA  CCA  AAT  GTC  AAC  ATC     750
Cys  Gly  Val  Tyr  Met  Asn  Arg  Gln  Ser  Ser  Cys  Cys  Tyr  Trp  Lys  Ser  Arg  Lys  Pro  Gly  Pro  Asn  Val  Asn  Ile
```

FIG. 12(1)

```
AAT GGA TGC CTA CTG AAT GAG TAT TAC ACG GTG TCA TTC ACC CCA AAC ATA TCT TTT GAT TCT GAC CAT TGC
Asn Gly Cys Leu Leu Asn Glu Tyr Tyr Thr Val Ser Phe Thr Pro Asn Ile Ser Phe Asp Ser Asp His Cys   825

AAA TAT GAG GAT CGT GTT GAA TTG ATC CGG ACC GTG TCA TTC ATC GGA AAA GAA GTT TTT AAG GTT GAG ATA CTT
Lys Tyr Glu Asp Arg Val Glu Leu Ile Arg Thr Val Ser Phe Ile Gly Lys Glu Val Phe Lys Val Glu Ile Leu   900

AAC TGC ACG CAG GAC GAC ATT AAG AGA GCA CTC ATA GCA AAC CAC CTG TCA CTC AGG CTC AAA CTA CAA
Asn Cys Thr Gln Asp Asp Ile Lys Arg Ala Leu Ile Ala Asn His Leu Ser Leu Arg Leu Lys Leu Gln   975

GCA TGC GAG CAT CCA ATC GGC GAA ATG TGC ATG TAT CCG AAG TTG CTG AAA AAC TCT GCA ACA GAA
Ala Cys Glu His Pro Ile Gly Glu Met Cys Met Tyr Pro Lys Leu Leu Lys Asn Ser Ala Thr Glu   1050

ATC GAA GAA AAC CTT TGC AGT CTG TGC GAA CAG GCT CTG TAC AAT CAA ACA CGA AAA TGC GTC
Ile Glu Glu Asn Leu Cys Ser Leu Cys Glu Gln Ala Leu Tyr Asn Gln Thr Arg Lys Cys Val   1125

AAG GTC GAC AAC CTC TTC TGG CAG TGC GCT TAC ACT GAG ATG CAG CAG GTT TGT ATG GGT CGC CTA
Lys Val Asp Asn Leu Phe Trp Gln Cys Ala Tyr Thr Glu Met Gln Gln Val Cys Met Gly Arg Leu   1200

CGC CGC GTG TCC AAA GCT GGA GCT GAA AAC GAA CAG TTG CTT GAA GGG CAA ATA
Arg Arg Val Ser Lys Ala Gly Ala Glu Asn Glu Gln Leu Leu Glu Gly Gln Ile   1275

TGT GTT TAC GAA AAC GGC GCG AAT TCT TGC CCA CCA GAC ACT AAG AAG ATT GGC ATT
Cys Val Tyr Glu Asn Gly Ala Asn Ser Cys Pro Pro Asp Thr Lys Lys Ile Gly Ile   1350

CGT ACC ACA TGC AAC CCT AAA ATA CAA GAA GAC GTG AAG TAC AAC CAT AAA
Arg Thr Thr Cys Asn Pro Lys Ile Gln Glu Asp Val Lys Tyr Asn His Lys   1425

GCA GAA GCT CCT GAT GAT CAC GAG AGG AGG GAG CCT GCC AAA TCT TGC AGT GAT AAT
Ala Glu Ala Pro Asp Asp His Glu Arg Arg Glu Pro Ala Lys Ser Cys Ser Asp Asn   1500
```

FIG. 12(2)

```
                                                                              1575              1647
GGT AAA TGT CAA AGC AGT GGG CAG CGT TGT GTA ATA GAA AAC GGA AAG GCT GTT TGC AAG GAA AAG TCT GAA GCA
Gly Lys Cys Gln Ser Ser Gly Gln Arg Cys Val Ile Glu Asn Gly Lys Ala Val Cys Lys Glu Lys Ser Glu Ala

ACA ACA ACT GCG ACA ACA ACG AAA GCG AAA GAC AAG GAT CCA GAT CCT GGA AAG TCA AGT GCA GCA
Thr Thr Thr Ala Thr Thr Thr Lys Ala Lys Asp Lys Asp Pro Asp Pro Gly Lys Ser Ser Ala Ala
```

FIG. 13

```
CCC CCT CGA GGT CGA CGG TAT CGA TAA GCT TGA TAT CGA ATT CCG CCG GCC GAG ATG CGT GGC ATC GCT TTG  75
                                                                 Met Arg Gly Ile Ala Leu

TTC GTC GCC GCT GTT TCA CTG ATT GTA GAG TGC ACA GCA GAA TCA TCC ATT TGC TCT GAC TTC GGG AAC GAG TTC 150
Phe Val Ala Ala Val Ser Leu Ile Val Glu Cys Thr Ala Glu Ser Ser Ile Cys Ser Asp Phe Gly Asn Glu Phe

TGC CGC AAC GCT GAA TGT GAA GTG GTG CCT GGT GCA GAG GAT TTC GTG TGC AAA TGT CCG CGA CGA GAT AAT ATG 225
Cys Arg Asn Ala Glu Cys Glu Val Val Pro Gly Ala Glu Asp Phe Val Cys Lys Cys Pro Arg Asp Asn Met

TAC TTC AAT GCT GCT GAA CAA TGC TAT AAA GAC ACG ACG AAG AGG GAG TGT GGA TAT GGA CGT TGC 300
Tyr Phe Asn Ala Ala Glu Gln Cys Tyr Lys Asp Thr Thr Lys Arg Glu Cys Gly Tyr Gly Arg Cys

GTT GAA AGT GCT AAC CCG AGC AAG TGC GTC TGC GAA GCA TCG ACG CTA ACG CAA TGC AAA ATT AAA 375
Val Glu Ser Asn Pro Ser Lys Cys Val Cys Glu Ala Ser Thr Leu Thr Gln Cys Lys Ile Lys

AAT GAC TAC GCA ACT GAC TGC CGA AAT GCT GGC GAT TTG CGC ACG GAT GGG TTT ATT GGC GCA ACG 450
Asn Asp Tyr Ala Thr Asp Cys Arg Asn Ala Gly Asp Leu Arg Thr Asp Gly Phe Ile Gly Ala Thr

TGT GAC TGT GAA TGG GGT GCG ATG AAC CGG AAC ACC ACC CCT GTC CTT CGT CCC GAC 525
Cys Asp Cys Glu Trp Gly Ala Met Asn Arg Asn Thr Thr Pro Val Cys Leu Arg Pro Asp

TTG ACC TGC AAA GAC CTC TGC GAG AAA CTG CTT CAA AGG GAT TCT TGT TGC CAG GGG TGG AAC ACA GCA 600
Leu Thr Cys Lys Asp Leu Cys Glu Lys Leu Leu Gln Arg Asp Ser Cys Cys Gln Gly Trp Asn Thr Ala

AAC TGT TCA GCC GCT GCT CCA GCT GAC TCC TAT TGC TCT CCT GGG AGC CCC AAA GGA CCG CAG TGT ATA 675
Asn Cys Ser Ala Ala Ala Pro Ala Asp Ser Tyr Cys Ser Pro Gly Ser Pro Lys Gly Pro Gln Cys Ile

AAT GCT TGC AAG ATG AAA GAA CAG GCT GGT TTT GTC TGC TGG CAT GGA ACC AGG TCG ACC GCC AAG TAC GAG TGC 750
Asn Ala Cys Lys Met Lys Glu Gln Ala Gly Phe Val Cys Trp His Gly Thr Arg Ser Thr Ala Lys Tyr Glu Cys

ACG TGC CCA CGT GGC TTT ACC GTC ACC GAA GAT GCG ATT ACC AGT ATT ATC TCG CAC ACA GTC AGC TGC ACT 825
Thr Cys Pro Arg Gly Phe Thr Val Thr Glu Asp Ala Ile Thr Ser Ile Ser His Thr Val Ser Cys Thr

GCT GAG CAA CAG CAA ACC GAA ACC CCA CAC TGC CGT GTG ACT TTG TGT GAG TGC CCG 900
Ala Glu Gln Gln Gln Thr Glu Thr Pro His Cys Arg Val Thr Leu Cys Glu Cys Pro

TGG AAT CAA CAT CTA GTG GGG GAC ACG TGC ATA AGT GAT TGC GAC AAG AAA TGC CAC GAA TTT ATG GAC 975
Trp Asn Gln His Leu Val Gly Asp Thr Cys Ile Ser Asp Cys Asp Lys Lys Cys His Glu Phe Met Asp
```

FIG. 13(1)

```
TGT GGC GTA TAT ATG AAT CGA CAA AGC TGC TAT TGT CCA TGG AAA TCA AGG AAG CCG GGC CCA AAT GTC AAC ATC 1050
Cys Gly Val Tyr Met Asn Arg Gln Ser Cys Tyr Cys Pro Trp Lys Ser Arg Lys Pro Gly Pro Asn Val Asn Ile

AAT GGA TGC CTA CTG CTA AAT GAG TAT TAC ACG GTG TCA TTC ACC CCA AAC ATA TCT GAC TTT GAT TCT GAC CAT TGC 1125
Asn Gly Cys Leu Leu Leu Asn Glu Tyr Tyr Thr Val Ser Phe Thr Pro Asn Ile Ser Asp Phe Asp Ser Asp His Cys

AAA TGG TAT GAG GAT CGT GTT GAA TTG GAA GCG ATA CGG ACC AGT ATC GGA AAA GAA GTT TTT AAG GTT GAG ATA CTT 1200
Lys Trp Tyr Glu Asp Arg Val Glu Leu Glu Ala Ile Arg Thr Ser Ile Gly Lys Glu Val Phe Lys Val Glu Ile Leu

AAC TGC ACG CAG GAC ATT AAG GCA AGA CTC ATA GCA GAG CCA CTG TCA AAC CAC GTG CTC AGG AAA CTA CAA 1275
Asn Cys Thr Gln Asp Ile Lys Ala Arg Leu Ile Ala Glu Pro Leu Ser Asn His Val Leu Arg Lys Leu Gln

GCA TGC GAG CAT CCA ATC GGC GAA TGG GAA GGT CTG AAG TTG CTG ATC AAG AAA AAC TCT GCA ACA GAA 1350
Ala Cys Glu His Pro Ile Gly Trp Glu Trp Cys Met Met Tyr Pro Lys Leu Leu Ile Lys Lys Asn Ser Ala Thr Glu

ATC GAA GAG AAC CTT TGC AGT GCC CTG CTC AAG GCT GAA AAT CAG TAC AAA GGT CAA AAC AAA TGC GTC 1425
Ile Glu Glu Asn Leu Cys Ser Asp Ser Leu Leu Lys Ala Glu Asn Gln Tyr Lys Gly Gln Asn Lys Cys Val

AAG GTC GAC AAC CTC TTC TGG TGC GCT GAT GGT TAC ACA ACT TAC GAG ATG ACA CGA GGT CGC CTA 1500
Lys Val Asp Asn Leu Phe Trp Cys Ala Asp Gly Tyr Thr Thr Tyr Glu Met Thr Arg Gly Arg Leu

CGC CGC TCC GTG TGT AAA GCT GGA GTT TCT TGC AAC GAA CAG TTG CAG GAG TGT GCT GAC AAA CCT GGG CAA AAA ATA 1575
Arg Arg Ser Val Cys Lys Ala Gly Val Ser Cys Asn Glu Gln Leu Gln Glu Cys Ala Asp Lys Pro Gly Gln Lys Ile

TGT GTT TAC GAA CTG TAC GAT GAT CAC CAA TGC CAA GAA ATA GAA GAC CAA AAG CTG TTG TAC AAA AAC CAT GAG 1650
Cys Val Tyr Glu Leu Tyr Asp Asp His Gln Cys Gln Glu Ile Glu Asp Gln Lys Leu Leu Tyr Lys Asn His Glu

CGT ACA ACA CCT CGT CCT GAT CAC CGT CAG ATA TTG CAA GAC TGT GTT TCC AGG GAG CCT GCC AAG GAG CTG GTT TGC AGT GAA 1725
Arg Thr Thr Pro Arg Pro Asp His Arg Gln Ile Leu Gln Asp Cys Val Ser Arg Glu Pro Ala Lys Glu Leu Val Cys Ser Glu

GCA TGC AAG TGT CCT CCT GAT CAC CGT CAG ATA TTG CAA GAC TCT TGC AGT TGC GAA CTG GTT CCT GCC AAG GAG TCT GAA GAT 1800
Ala Cys Lys Cys Pro Pro Asp His Arg Gln Ile Leu Gln Asp Ser Cys Ser Cys Glu Leu Val Pro Ala Lys Glu Ser Glu Asp

GGT AAA TGT CAA AGT GGG AAG ATA GTA ATA GAA AAC GGA AAG GCT GTT GTT CTC AAG GCT AAA TCT GAA GCA 1875
Gly Lys Cys Gln Ser Gly Lys Ile Val Ile Glu Asn Gly Lys Ala Val Val Leu Lys Ala Lys Ser Glu Ala

ACA ACA GCT GCG ACT ACA ACA ACG AAA GCG AAA GCC CCT GGA AAG TCA AGT GCA GCA GTA 1950
Thr Thr Ala Ala Thr Thr Thr Thr Lys Ala Lys Ala Pro Gly Lys Ser Ser Ala Ala Val
```

FIG. 13(2)

```
TCA GCT ACT GGG CTC TTG TTA CTG CTC GCA GCT ACT TCA GTC ACC GCA GCA TCG TTG TAA GGA AGM TGT CCA ACT 2025
Ser Ala Thr Gly Leu Leu Leu Leu Leu Ala Ala Thr Ser Val Thr Ala Ala Ser Leu

NCA ATA CGG AAC AGC TTG AAT ATG TAT ATA TAC ATC ACG CTT ACA TCG AAC ACC TAG CTT GGT TTT TGG AAT TTC 2100

AAT ATT GCG CAT TGG TAC TCA CNG CAA CAT GAA TGT ATT ACT TTA GAA TGA CAG GGA AGA GGG ACG TGA AAG GAG 2175

TTT CCT TGT CTG AAC ATA TCA AAG AAA ATT TTC CCC TAT CCG ACC GAT GTC AGC GGC CGC GAA TTC CTG CAG CCC 2250

GGG GGA TCC ACT AGT TCT AGA GCG GCC GGC CGC GTT AAC CAC CGC GGT GGA GCT CCA G                      2308
```

FIG. 14

```
TTC TGT CGC AAC GCT GAA TGC GAA GAG GTG CCT GGT GCC GAG GAT GAT TTC GTG TGC AAA TGT CCG CGA TAT AAT   75
Phe Cys Arg Asn Ala Glu Cys Glu Glu Val Pro Gly Ala Glu Asp Asp Phe Val Cys Lys Cys Pro Arg Tyr Asn

ATG TAC TTC AAT GCT GCT CCG AAC CAA GAG TAT GGT TGT ACA AGA GAT ACG TGC AAG GAG TGC AGC TAT GGC CGT  150
Met Tyr Phe Asn Ala Ala Pro Asn Gln Glu Tyr Gly Cys Thr Arg Asp Thr Cys Lys Glu Cys Ser Tyr Gly Arg

TGC GTT CAA AGT AAC CCG AAG AGC TGT GTC TGC GAA GCA TCT CTA GAC ACT CTA CAA TGC AAC ATT  225
Cys Val Gln Ser Asn Pro Lys Ser Cys Val Cys Glu Ala Ser Leu Asp Thr Leu Gln Cys Asn Ile

AAC AAT GAC TAC GCA ACT GAC TGC CGA AAC AGG GGT GGT ACC GCT AAG TTG CGC ACG GAT GGG TTT ATT GGC GCA  300
Asn Asn Asp Tyr Ala Thr Asp Cys Arg Asn Arg Gly Gly Thr Ala Lys Leu Arg Thr Asp Gly Phe Ile Gly Ala

ACG TGT GAC GGT GAA ATG GGC GCA ATG AAC ACC ACC CGG AAC AAG ACC CCT GTC CTT ATT CGT CTT CGT CCC  375
Thr Cys Asp Gly Glu Met Gly Ala Met Asn Thr Thr Arg Asn Lys Thr Pro Val Pro Ile Arg Thr Leu Arg Pro

GAC TTG ACC TGC AAA GAC CTC TGC GAG AAA ATG CTG CTT CAA CTC TCT CGT TGT CAG AAC ACA  450
Asp Leu Thr Cys Lys Asp Leu Cys Glu Lys Met Leu Leu Gln Leu Ser Arg Cys Gln Asn Thr

GCA AAC TGT TTA GCC GCT CCA GCT GAC TCC TAT GAC TCC TAT GAC TCC CCT CCT AGC CCC AAA GGA CAG TGT  525
Ala Asn Cys Leu Ala Ala Pro Ala Asp Ser Tyr Cys Ser Pro Lys Gly Ala Asp Pro Lys Ser Gly Gln Cys

AAA AAT GCT TGC AGG ACG GAA GAA GCT GGG GTC GTC TTT GTC TGC CAT GGA AAG TCC TGG GGA CCG TAC GAG  600
Lys Asn Ala Cys Arg Thr Glu Glu Ala Gly Val Val Phe Val Cys His Gly Lys Ser Trp Gly Pro Tyr Glu

TGC ACG TGC CCG AGT GGC TCT ACC GTC GCC CGA CCA GAT GAT GGG GCT ATT GTG ATT ACC GAC AAG GCG TGC  675
Cys Thr Cys Pro Ser Gly Ser Thr Val Ala Arg Pro Asp Asp Gly Ala Ile Val Ile Thr Asp Lys Ala Cys

ACT GTT GAG CAA CAG CAT CTA GTG AAT CAG AAG CGT GAT TGT CCA CGG GAC TGT GTC AAA AAG GGC ACT GTG TTG TGT GAG  750
Thr Val Glu Gln Gln His Leu Val Asn Gln Lys Arg Asp Cys Pro Thr Asp Val Lys Lys Gly Thr Val Leu Cys Glu

CCG TGG CAA CAA CAT CTA ATG TAT CGA CAA AGC GAA GAC TGC AAG AGT CGC TGC TCA CCA TGG CCA GAA GAA TTT ATG  825
Pro Trp Gln Gln His Leu Met Tyr Arg Gln Ser Glu Asp Cys Lys Ser Arg Cys Ser Pro Trp Pro Glu Glu Phe Met

GAC TGT GGC GTA AAT CAA CGA GAG CAA AGC GAC GTC AAA TGG AGG AAG CCG GGC CCA AAT GTC AAC  900
Asp Cys Gly Val Asn Gln Arg Glu Gln Ser Asp Val Lys Trp Arg Lys Pro Gly Pro Asn Val Asn

ATC AAT GAA CTG CTA AAT GAG TAT GAG ACG TCA TTC ACC CCG AAG ATA TCT TTT GAT TCT GAC CAT  975
Ile Asn Glu Leu Leu Asn Glu Tyr Tyr Thr Ser Phe Thr Pro Asn Ile Ser Phe Asp Ser Asp His
```

FIG. 14(1)

```
TGC AAA CGG TAT GAG GAT CGT GTT TTG GAA GCG ATA CGG ACC AGT ATC GGA AAA GAA GTT TTT AAG GTT GAG ATA 1050
Cys Lys Arg Tyr Glu Asp Arg Val Leu Glu Ala Ile Arg Thr Ser Ile Gly Lys Glu Val Phe Lys Val Glu Ile

CTT AAC TGC ACG CAG GAC GAC ATT AAG GCA AGA CTC ATA ATA GCA GAG CTG TCA AAA TAC GTG CTC AGG AAA CTA 1125
Leu Asn Cys Thr Gln Asp Asp Ile Lys Ala Arg Leu Ile Ile Ala Glu Leu Ser Lys Tyr Val Leu Arg Lys Leu

CAA GCA TGC GAG CAT CCA ATC GGC GAA TGG TGC ATG ATG TAT CCG AAG ATC AAG AAA AAC TCT GCA ACA 1200
Gln Ala Cys Glu His Pro Ile Gly Glu Trp Cys Met Met Tyr Pro Lys Ile Lys Lys Asn Ser Ala Thr

GAA ATT GAA GAA GAG CTT TGC GAC AGT CTG CTC AAG AAT CAG GAA GCC TAC AAA GGT CAA AAC AAA TGC 1275
Glu Ile Glu Glu Glu Leu Cys Asp Ser Leu Leu Lys Asn Gln Glu Ala Tyr Lys Gly Gln Asn Lys Cys

GTC AAG GTC GAC AAC CTC TTC TTC CAG TGC GCT GAT GGT TAC ACA ACT TAC GAG ATG ACA CGA GGT CGC 1350
Val Lys Val Asp Asn Leu Phe Phe Gln Cys Ala Asp Gly Tyr Thr Thr Tyr Glu Met Thr Arg Gly Arg

CTA CGC CGC TCC GTG TGT AAA GCT GTT TCT TGC GAG CAG TTG GAG TGT AAC AAA GGT CAA 1425
Leu Arg Arg Ser Val Cys Lys Ala Val Ser Cys Glu Gln Leu Glu Cys Asn Lys Gly Gln

ATA CGC TGT GTC TAC GAA TGC ACA GAA AAC GCG AAA CCT CCA GAC ACT AAA CCA GGG GAG ATT GGC TGC ATT 1500
Ile Arg Cys Val Tyr Glu Cys Thr Glu Asn Ala Lys Pro Pro Asp Thr Lys Pro Gly Glu Ile Gly Cys Ile

GAG CGT ACC ACA TGC AAC CCT ACT TGC AAA GAG ATA CAA GAA CTC GAG CTC GTT TGC TAC AAA AAC CAT 1575
Glu Arg Thr Thr Cys Asn Pro Thr Cys Lys Glu Ile Gln Glu Leu Glu Leu Val Cys Tyr Lys Asn His

AAA GCA GAA TSS AAG TGT CCT GAT GAT CAC GAG TGT TCT GCC AAA GAC TCT AGT TGC AGT GAA GAA GAT 1650
Lys Ala Glu Xaa Lys Cys Pro Asp Asp His Glu Cys Ser Ala Lys Asp Ser Ser Cys Ser Glu Glu Asp

AAT GGT CAA AGC TCG CAA AGT CGT TGT GTA ATG CAG CGT AAA GCG AAT GCT GTT TGC AAA GAG AAG TCT GAT 1725
Asn Gly Gln Ser Ser Gln Ser Arg Cys Val Met Gln Arg Lys Ala Asn Ala Val Cys Lys Glu Lys Ser Asp

GCA ACA ACA GCT TCG ACT ACA ACG ACA AAA GAC GAT CCA GAT CCT GAA GCA AGT TCA AAG GCT GCA GCA 1800
Ala Thr Thr Ala Ser Thr Thr Thr Thr Lys Asp Asp Pro Asp Pro Glu Ala Ser Ser Lys Ala Ala Ala

GTA TCA GCT ACT GGG CTC TTG TTA CTC CTC GCA GCT ACT TCA GTC ACC GCA TCG AAC ATC TAG CTT GGT CTT TGG AGA TGT CCA 1875
Val Ser Ala Thr Gly Leu Leu Leu Leu Leu Ala Ala Thr Ser Val Thr Ala Ser Leu

ACT TGA ATA CGG AAC AGC TTG AAA ATG TAT ATA TAC ATC ACG CTT ACA TCG AAC ATC TAG CTT GGT CTT TGG AAT 1950
```

FIG. 14(2)

```
TTA AAT ATT GCA CAT GGG TAC TCA CGG CAA AAT GGA CGT ATT ATT TTA GAA TGA CAG GGA AGA TGG ACG TGA AAG  2025

GAG TTT CCT TGT CTG AAA ATA TCA AAG AAA AAC TTT CCC TAT CTG AAT GAT GTC AAA TAA AGA TAG TTG GGT CTA  2100

AAC AAA AAA AAA AAA AAA AAA AAA GCG GCC G                                                             2131
```

FIG. 15

```
CAG GAT CCG TGG AAA GTG CGA CAG CTG CGG TGG TTC GAC GCA GTC GAG ATG CGT GGC ATC GCT TTG TTC GTC GCC  75
                                                         Met Arg Gly Ile Ala Leu Phe Val Ala

GCT GTT TCA CTG ATT GTA GAG TGC ACA GCA GAA TCA GCA GAG TGC TTC GAC TCT ATT TGC TCT GAG TTC GTC GCC AAC 150
Ala Val Ser Leu Ile Val Glu Cys Thr Ala Glu Ser Asp Phe Ile Cys Ser Glu Asn Glu Phe Cys Arg Asn

GCT GAA TGT GAA GTG GTG CCT GGT GCA GAG GAT TTC CCG AAA TGT GAT TAC ATG TAC TTC AAT 225
Ala Glu Cys Glu Val Val Pro Gly Ala Glu Asp Phe Pro Lys Cys Asp Asn Met Tyr Phe Asn

GCT GCT GAA AAG CAA TGC GAA TAT AAA GAT ACG TGC AAG GAG TGC TGC CGT TGC GTT GAA AGT 300
Ala Ala Glu Lys Gln Cys Glu Tyr Lys Asp Thr Cys Lys Glu Cys Cys Arg Cys Val Glu Ser

AAC CCG AGC AAG TGC GTC GAA GCA TCG CTA ACG GAC GAT TGC CAA CTA AAA ATT AAA GAC TTC 375
Asn Pro Ser Lys Cys Val Glu Ala Ser Thr Asp Asp Cys Gln Leu Thr Lys Ile Lys Asp Phe

GCA ACT GAC TGC CGA AAC GGT GGT ACT GCT AAG GCT GAT TTG CGC CCA ACG TGT GAC TGT 450
Ala Thr Asp Cys Arg Asn Gly Gly Thr Ala Lys Ala Asp Leu Arg Pro Thr Cys Asp Cys

GGT GAA GCG ATG AAA ACC CGG AAC CGT GTC CCT CTT CGT CCC GAC TTG ACC TGC 525
Gly Glu Ala Met Asn Lys Thr Arg Asn Cys Val Pro Leu Arg Pro Asp Leu Thr Cys

AAA GAC CTC TGC GAG AAA CTG CTT CAA AGG GAT TCT TGT TGT CAG GGG TGG AAC ACA GCA AAC TGT TCA 600
Lys Asp Leu Cys Glu Lys Leu Leu Gln Arg Asp Ser Cys Cys Gln Gly Trp Asn Thr Ala Asn Cys Ser

GCC GCT CCA CCA GCT GAC TCC TAT TGC CCT GGG AGC CCC AAA GGA CAG GGA GAC AAG AAT GCT TGC 675
Ala Ala Pro Pro Ala Asp Ser Tyr Cys Pro Gly Ser Pro Lys Gly Gln Gly Asp Lys Asn Ala Cys

AGG ACG AAA GAA GCT GGG CAT GTC TGC AAG CAT GGA CCC AGG TCC AGG TCC GCC GCA TAC GAG TGC ACG 750
Arg Thr Lys Glu Ala Gly His Val Cys Lys His Gly Ala Tyr Glu Cys Thr

AGT GGC TCT ACC GTC GCC GAT GGC ATT ACC AAA AGT ATT TCG CAG ACT GTG TTG TGT AGC ACT GTT GAG 825
Ser Gly Ser Thr Val Ala Asp Gly Ile Thr Lys Ser Ile Ser Gln Thr Val Leu Cys Ser Thr Val Glu

AAA CAG ACC TGC CGC CCA GAA ACC CAG GAT GTC CGT TGT CGT CAG AAA AAA GGA TGC CCG TGG AAT CAA 900
Lys Gln Thr Cys Arg Pro Glu Thr Gln Asp Val Arg Cys Arg Gln Lys Lys Gly Cys Pro Trp Asn Gln

CAT CTA GTG GGG GAC ACG ATA AGT GAT TGC GTC GAC AAG AAG AAA TGT CAC GAA GAA TTT ATG GAC TGT GGC GTA 975
His Leu Val Gly Asp Thr Ile Ser Asp Cys Val Asp Cys Lys Lys Lys Cys His Glu Phe Met Asp Cys Gly Val
```

FIG. 15(I)

```
TAT ATG AAT CGA CAA AGC TGC TAT TGT CCA TGG AAA AGG CCG AAT GTC AAT GAA TGC 1050
Tyr Met Asn Arg Gln Ser Cys Tyr Cys Pro Trp Lys Arg Pro Asn Val Asn Glu Cys

CTA CTG AAT GAG TAT TAC TAC ACG GTG TCA TTC ACC CCG AAC CAT TGC AAA CGG TAT 1125
Leu Leu Asn Glu Tyr Tyr Tyr Thr Val Ser Phe Thr Pro Asn His Cys Lys Arg Tyr

GAG GAT CGT GTT TTG GAA GCA ATA CGG AGT ACC ATC GGA GTT TTT AAG GTT AAC TGC ACG 1200
Glu Asp Arg Val Leu Glu Ala Ile Arg Ser Thr Ile Gly Val Phe Lys Leu Asn Cys Thr

CAG GAC ATT AAG GCA AGA CTC ATA ATA CCA AAA CTG CTC TCA CAA CTA CAA GCA TGC GAG 1275
Gln Asp Ile Lys Ala Arg Leu Ile Ile Pro Lys Leu Leu Ser Gln Leu Gln Ala Cys Glu

CAT CCA ATC GGC GAA ATG TGC TAT CCG AAG TTG CTG TTG AAA AAC TCT GCA ACA ATT GAA GAA 1350
His Pro Ile Gly Glu Met Cys Tyr Pro Lys Leu Leu Leu Lys Asn Ser Ala Thr Ile Glu Glu

GAG AAC CTT TGC GAC AGT CTG CTC AAG AAT CAG CAA GCT GCC AAA AAA TGC AAG GTC GAC 1425
Glu Asn Leu Cys Asp Ser Leu Leu Lys Asn Gln Gln Ala Ala Lys Lys Cys Lys Val Asp

AAC CTC TTC TGG TTC CAG TGC GAT TAC ACA ACT ACT CGA ATG CGC CTA CGC TCC 1500
Asn Leu Phe Trp Phe Gln Cys Asp Tyr Thr Thr Thr Arg Met Arg Leu Arg Ser

GTG TGT GGA GTT TCT GGA AAT TGC CAA TGC CAG ACT TTG GAG TGT AAA GGT CAA ATA TGC TAC 1575
Val Cys Gly Val Ser Gly Asn Cys Gln Cys Gln Thr Leu Glu Cys Lys Gly Gln Ile Cys Tyr

GAA AAC GGT CTA AAA GCT GAG CAC GAT AAA GAC AAG CTC GAG CCA GGG TGC GTT TAC AAA AAC CAT AAA GCA GAA TGC 1725
Glu Asn Gly Leu Lys Ala Glu His Asp Lys Asp Lys Leu Glu Pro Gly Cys Val Tyr Lys Asn His Lys Ala Glu Cys

TGC AAC CCT AAG CAC CAG CCT GCA AAG AAG AAG GCT GTT GTT AAA TGC GAT GAA GAG TCT GAA AAT GGT AAA TGT 1800
Cys Asn Pro Lys His Gln Pro Ala Lys Lys Lys Ala Val Val Lys Cys Asp Glu Glu Ser Glu Asn Gly Lys Cys

AAG TGT CCT GAT GAT CAC CGT TCT AGG CAG CCT GTT CCT GGA AAG TCT GAA GAG AAG TCT GAA GAG AAG ACA GCT 1875
Lys Cys Pro Asp Asp His Arg Ser Arg Gln Pro Val Pro Gly Lys Ser Glu Glu Lys Ser Glu Glu Lys Thr Ala

CAA AGC AGT GGG CAG CGT TGT GTA ATG GAA AAG GCT CCT GGA AAG TCA AGJ GCT GCA GTA TCA GCT ACT 1950
Gln Ser Ser Gly Gln Arg Cys Val Met Glu Lys Ala Pro Gly Lys Ser Arg Ala Ala Val Ser Ala Thr

GCG ACT ACA ACG AAA GAC AAG AAG GAT CCT GGA AAG TCA AGJ GCT GCA GTA TCA GCT ACT
Ala Thr Thr Thr Lys Asp Lys Lys Asp Pro Gly Lys Ser Arg Ala Ala Val Ser Ala Thr
```

FIG. 15(2)

```
GGG CTC TTG TTA CTG CTC GCA GCT ACT TCA GTC ACC GTA GCA TCG TTG TAA TGA AGA TGT CCA ACT TGA ATA CGG 2025
Gly Leu Leu Leu Leu Leu Ala Ala Thr Ser Val Thr Val Ala Ser Leu

AAC AGC TTG AAA ATG TAT ATA TAC ATC GCG CTT ACA TCG AAC ACC TAG CTT GGT TTT TGG GAT TTC AAT ATT GCG 2100

CAT GGG TAC TCA CGT CAA CAT GGG ATG TAT TAT TTG AGA ATG ACA AG                                     2147
```

FIG. 16

```
GCC CTT GTT TTG GAC GCG ATA AAG ACC AGT ATC GGA AGC GAA GTT TCT AAA CTT GAG ATA CTG AAC TGC ACG CAG  75
Ala Leu Val Leu Asp Ala Ile Lys Thr Ser Ile Gly Ser Glu Val Ser Lys Leu Glu Ile Leu Asn Cys Thr Gln

GAT ATT AAG GCA AGG CTC ATA GTA CCG AAA CCG CTA TCA AAG CAC GTG CTC AAG AAG CTT CAA GCA TGC GAG CAT 150
Asp Ile Lys Ala Arg Leu Ile Val Pro Lys Pro Leu Ser Lys His Val Leu Lys Lys Leu Gln Ala Cys Glu His

CCC GTC GGG GAC TTG TGT ATG CTG TAT CCG AAG TTG CCG ATC AAG AAA AAC TCT GCG ACA GAA ATT GAA GAA GAG 225
Pro Val Gly Asp Leu Cys Met Leu Tyr Pro Lys Leu Pro Ile Lys Lys Asn Ser Ala Thr Glu Ile Glu Glu Glu

AAC CTT TGC GAC AGC CTC CTC AAG CGT CAG GAA GCT GCC TAC AAG GGT CAG AAC AAA TGC GTC AAG GTC GGT AAC 300
Asn Leu Cys Asp Ser Leu Leu Lys Arg Gln Glu Ala Ala Tyr Lys Gly Gln Asn Lys Cys Val Lys Val Gly Asn

ATT TTC TGG TTC CAG TGC GCT GAT TAC AGA TCA GTT TAC GAC ATC ACA CAA GGT CTA CGC CGC CTC GTG 375
Ile Phe Trp Phe Gln Cys Ala Asp Tyr Arg Ser Val Tyr Asp Ile Thr Gln Gly Leu Arg Arg Ser Val

TGC GAA CGT GGA ATT TCT TGC AGT GAT AAT GAA CAG TTG GAG TGT GCC AAG AAA GGA CAA ATA TGT 441
Cys Glu Arg Gly Ile Ser Cys Ser Asp Asn Glu Gln Leu Glu Cys Ala Lys Lys Gly Gln Ile Cys
```

DNA ENCODING A CELL MEMBRANE GLYCOPROTEIN OF A TICK GUT

This application is a continuation of Ser. No. 08/062,109, filed May 17, 1993, abandoned, which is a continuation-in-part of Ser. No. 07/926,368, filed Aug. 7, 1992, abandoned, which is a continuation-in-part of Ser. No. 07/242,196, filed as PCT/AU87/00401, Nov. 27, 1987, abandoned.

TECHNICAL FIELD

This invention relates to an antigen isolated from the cattle tick *Boophilus microplus* and to the gene coding for that antigen and to the protein product of that gene. The antigen when used in part or in entirety as an immunogen administered to cattle as a vaccine results in the production by the cattle of an immune response which is capable of damaging ticks feeding on vaccinated cattle to such an extent that the survival of such ticks is decreased and/or the reproductive capacity of the ticks is decreased to such an extent that the antigen coded for by the gene can be used as an effective vaccine against said ticks.

BACKGROUND ART

On first infestation with ticks such as the cattle tick, *Boophilus microplus,* animals such as cattle are very susceptible to the parasite. Typically about 50% of the tick larvae which attach, complete the full life cycle to eventually drop off as engorged adults. On prolonged exposure to the parasite, cattle acquire some degree of immunological resistance to it, but this resistance reaches a relatively stable level at which economically important losses to cattle production still occur. The losses to production are largely due to losses of blood and tissue fluid taken up by the parasite during feeding. Additional losses are due to the hypersensitive or allergic response which animals develop to tick salivary and cement antigens in conjunction with natural immunity, a condition known as tick worry.

A large number of approaches are used to control ticks. The most widely used is treatment of cattle with acaracides -chemicals which kill ticks. This approach has several short comings. For example resistance to the chemicals arises in the tick population and new classes of chemicals must be introduced frequently. The chemicals have little residual effect so cattle must be treated frequently in order to control the ticks effectively. The chemicals may have detrimental effects on the cattle, personnel and the environment. A second method for control of ticks is to breed for host resistance. Zebu breeds and Zebu cross breeds are more resistant to ticks than the highly susceptible British breeds. However Zebu crosses have behavioural problems, are less productive than pure British breeds and, even with the use of chemicals, the degree of resistance to ticks is far from ideal. Other methods of tick management such as pasture spelling and tick eradication present practical problems in most cattle producing areas throughout the world. An effective vaccine against ticks would provide a highly attractive alternative to the currently available methods of tick control.

Intermittent attempts have been made in the past to immunise animals against ticks. (1–5, see 13 for review) The majority of these studies have used tick-host systems in which strong immunity seems to develop naturally, and have usually used laboratory animals as hosts. Usually the effects observed have been some reduction in engorgement weights and egg masses of adult ticks and some decrease in the viability of those eggs (1–5) although in two reports some decrease in the viability of engorging adults has been reported (3,4). Many of these studies have used antigens derived from salivary glands in order to attempt to mimic natural immunity. However, it is unlikely that a vaccine which mimics natural immunity would be of great commercial benefit due to the economic losses which still occur once natural immunity has been expressed and the deleterious effect of hypersensitivity responses to ticks.

The alternative approach is to vaccinate animals with "concealed" or "novel" antigens, "Concealed" or "novel" antigens are, in this context, components of the parasite which can be used to raise a protective immune response in animals when used (in partially or fully purified form) to vaccinate those animals, but are antigens which are not involved in naturally acquired immunity.

The successful vaccination against ticks using concealed or novel antigens has been reported (2,5). Animals were immunised with extracts of whole ticks or tick midgut. Immunization led to reductions in tick engorgement weights, feeding period, egg masses and egg viability but no significant increase in tick mortality was observed. However, the antigen fractions used in these experiments were so complex that it was not possible to identify the individual tick antigens which were responsible for the effects noted and the reasons for the effects were not investigated in detail.

In a recent patent application (Australian Patent Application No. 59707/86), claims are made that antigens derived from the synganglia of ticks can act as effective vaccines against tick infestation. However, there is no evidence presented in that patent that synganglia antigens can be effective alone. In this work dissected guts and synganglia were isolated, the gut cells were lysed, centrifuged and both the supernatant and pellet were used to vaccinate the same animals together, in some cases, with a cell suspension of synganglia. All cattle in the experiments reported were vaccinated with tick gut components and some received synganglia in addition. Therefore, it is clearly implicit in the experimental design that gut damage as a result of an immune response against gut components of ticks such as the gut cell antigens described herein and in the CSIRO patent application (45936/85), is an essential prerequisite for any secondary protective effects which may possibly result from an immune response against synganglia-specific antigens.

In all of the examples cited above, the tick extracts which were used to vaccinate the animals were extremely complex. In the majority of the reports the fractions used were homogenates of tick organs and in some cases, the pellets derived therefrom by centrifugation. In this and the other studies, no data on the complexity of the fractions is presented but it is certain that they must contain many hundreds and probably thousands of components. In the one study where any purification and characterization of the protective fraction was carried out (Australian patent application No. 45936/85) the most highly purified fraction, GF ⅚ was still very complex as will be shown below and it was not possible from this work to identify the individual component(s) of this fraction which were responsible for the protective immune response. In the present invention one such antigen is purified and characterized.

*Boophilus microplus* presents a particularly challenging problem. Since the naturally-acquired immunity is only partially effective, duplication of natural immunity by artificial immunization would be of comparatively little commercial value. *Boophilus microplus* is a parasite of cattle and does not feed readily on laboratory animals. The possibility of inducing "unnatural immunity" to *Boophilus microplus* has been examined and shown to be possible (6, 7, 8, Australian Patent Application No. 45936/85). The practical exploitation of this, however, would require as a first step the isolation of the antigen or antigens responsible, and as a second step, the development of means by which the effective antigens could be produced in quantities which would be sufficient for commercial uses.

The initial steps in the purification of the antigens in question and the demonstration of the efficacy of these antigens has been described previously (Australian Patent Application No. 45936/85). Briefly, ticks removed from cattle were disrupted, and sonicated, the cuticles and debris removed by low speed centrifugation, the supernatant was subjected to high speed centrifugation at 100,000× g for 1 hour, the membrane enriched pellet was extracted with a non-ionic detergent, the extract was subjected sequentially to chromatography on Sephacryl S-300 columns, broad range isoelectric focussing, narrow range isoelectric focussing and gel filtration chromatography on HPLC. At each step, fractions obtained were tested for efficacy as immunogens and the most highly protective fractions subjected to the next purification step. The most highly protective antigens were thus identified as being membranous, possessing an isoelectric point (pI) of between 5.05 and 5.65 and molecular weights in the range 205 to 79 kilodaltons. Other less highly protective fractions were also described and are of interest in both this and the preceding Australian Patent Application 45936/85.

Further development of the purification procedure as described herein has enabled the most highly protective antigens to be more clearly defined and characterised more precisely and has enabled animals to be vaccinated with more highly purified immunogen preparations. One such antigen has been purified to near homogeneity and it has been shown that when cattle are vaccinated with this tick component an immune response is generated in those cattle which results in the death of the majority of ticks used to challenge those vaccinated animals. The antigen isolated from ticks has been shown to be a glycoprotein with a molecular weight of approximately 89 kilodaltons and an isoelectric point in the range of 5.30 to 5.67. The method for the purification of this glycoprotein (referred to hereafter as the WGL$^+$ antigen or WGL$^+$) has been improved and a method is disclosed herein which results in a much larger yield of the antigen than could be obtained by the method previously described (Aust. Patent Application No. 45936/85). During this and previous work, other fractions which give protection have been identified.

Having devised means by which the WGL$^+$ antigen can be obtained in larger amounts (not sufficient for commercial uses), experiments have been performed to analyse the structure of parts of the protein portion of the antigen. The purified preparation was reduced and carboxy-methylated and digested with endoproteinase lys-C. The peptide fragments so produced were purified and the partial amino acid sequence determined for some peptides. This amino acid sequence data has enabled the design of oligonucleotides which have been used to isolate bacterial cells containing cDNA coding for the WGL$^+$ antigen.

Analysis of the DNA from these bacterial cells leads to the unambiguous identification of the gene coding for one protective antigen and the production of recombinant proteins which can be used as effective vaccines against ticks. These developments are the subject of the present invention.

DEFINITIONS

Whilst the invention provides products and processes suitable for the protection of cattle against tick infestation, it is to be understood that the principles of the invention can be equally applied to the protection of other animals such as horses, deer, goats, sheep, dogs, cats and pigs against tick infestation.

It is recognised that the tick population worldwide is genetically diverse as is the case for all organisms which reproduce sexually. Each individual of a population differs subtly from the others in the population and these differences are a consequence of differences in the sequence of the DNA which each individual inherits from its parents.

Further, random mutational events which can occur in either sexually or asexually reproducing organisms are a further source of genetic variation.

Thus for each gene encoding a particular protein, there are likely to be differences in the sequence among the population of individuals.

Such related molecules are referred to herein as homologues of antigens according to the invention and to the extent that they fulfill the functions of immunogens as defined herein they are included within the scope of the invention.

Homologous antigens may be defined as antigens related by evolution but not necessarily by function. Similar but not necessarily identical DNA or protein sequences may be provided. It should be noted however that function in this sense relates to the natural in vivo function of the protein.

Illustration of this point is provided by considering:

1. WGL$^+$ form *Boophilus microplus* and other tick species
2. WGL$^+$ from variants or different individuals of the *Boophilus microplus* population
3. WGL$^+$ and related gut cell plasma membrane glycoproteins from ticks which are homologues of the WGL$^+$ antigen defined herein.

It is stressed that for the purposes of this invention, homologues include only those WGL$^+$ related plasma membrane glycoproteins which function as immunogens as defined herein.

Such homologous WGL$^+$ related plasma membrane glycoproteins may exist in the tick population worldwide and will be capable, when incorporated into a vaccine, of eliciting in animals vaccinated with those antigens an immune response which is capable of killing ticks, by damaging tick gut cells and which additionally results in a reduction in tick engorgement weights or otherwise damaging the surviving ticks in such a way that for example egg production by those ticks is decreased to such an extent that the vaccine can be used commercially agains infestation by tick species such as Boophilus spp, Haemaphysalis spp, Otobius spp, Rhiphicephalus spp, Ambylomma spp, Dermacentor spp, Ixodes spp and Hyalomma spp, and especially from *B. annulatus, B. decoloratus, Otobius megnini, Rhiphicephalus appendiculatus, Dermacentor andersoni, D. variabilis, Haemaphysalis longicornis, Ambylomma variegatum* and *Ixodes holocyclus*.

Further, it should be recognised that it is possible to generate chemicals which are not related to the WGL$^+$ antigen by evolution or necessarily by structure but which may serve as immunogens to generate an immune response against protective epitopes on the WGL$^+$ antigen and thereby act as effective vaccines. These molecules are referred to herein as analogues and to the extent that they fulfill the functions of immunogens as defined herein, they are included within the scope of the invention. Such analogues include chemically synthesized oligopeptide molecules with sequences corresponding to portions of the amino acid backbone of the WGL$^+$ molecule, oligopeptides which when used as immunogens elicit an immune response which recognises native WGL$^+$ antigen in ticks, carbohydrate structures from whatever source which when used as antigens elicit an immune response which recognises the WGL$^+$ antigen in ticks, and anti-idiotype antibodies raised against the variable region of antibodies which recognise the epitope(s) of the WGL$^+$ antigen.

DISCLOSURE OF THE INVENTION

In a first embodiment the invention provides an immunogen comprising an antigen derived from a tick species or tick cell line which antigen is capable of inducing immunity to tick infestation of a mammalian host to which said immunogen has been administered characterised in that said immunity results in the mammalian host producing an immune response which is capable of damaging the plasma membrane of the gut cells of ticks feeding on said host to such an extent that the majority of said ticks fail to survive to adult stage or surviving ticks become red in colour and the reproductive capacity of said surviving ticks is substantially decreased wherein said immunogen includes immunogens displaying similar immunological activity to said antigen including parts, analogues, homologues, derivatives and combinations thereof of said antigen.

Preferably the antigen is derived from *Boophilus microplus*.

In a preferred embodiment the immunity induced is immunity to infestation by a Boophilus species.

More preferably the immunity induced is immunity to *B. microplus* infestation.

However, immunity may also be induced to other species of ticks, including Haemaphysalis spp, Otobius spp, Rhiphicephalus spp, Ambylomma spp, Dermacentor spp, Ixodes spp and Hyalomma spp and especially to other species of Boophilus such as *B. annulatus* or *B. decoloratus*.

Of the other species of ticks against which immunity can be induced preferred species include *Otobius megnini, Rhiphicephalus appendiculatus, Dermacentor andersoni, D. variabilis, Haemaphysalis longicornis, Ambylomma variegatum* and *Ixodes holocyclus*.

By immunization with related antigens isolated from other species of ticks including Boophilus spp, Haemaphysalis spp, Otobius spp, Rhiphicephalus spp, Ambylomma spp, Dermacentor spp, Ixodes spp and Hyalomma spp., immunity to infestation by other ticks may also be induced. Preferred species from which the related antigens are isolated include *B. annulatus, B. decoloratus, Otobius megnini, Rhiphicephalus appendiculatus, Dermacentor andersoni, D. variabilis, Haemaphysalis longicornis, Ambylomma variegatum* and *Ixodes holocyclus*. By protecting against infestation with ticks, the antigen may also provide protection against diseases caused by agents such as *Babesia bovis, Babesia bigemina, Anaplasma marginale, Cowdria ruminantium, Theileria parva parva, T. parva lawrencii, T. annulata* and *T. hirci*.

In a second embodiment the invention provides a polynucleotide sequence comprising a first polynucleotide sequence which acts as a coding sequence for amino acid sequences of an immunogen according to the invention, a polynucleotide sequence which hybridises to said first sequence or a polynucleotide sequence related to said first sequence or hybridising sequence by mutation including single or multiple base substitutions, deletions, insertions and inversions.

Preferably the polynucleotide sequence is a DNA sequence.

In a further preferred form of the invention the DNA sequence is a cDNA sequence.

The DNA sequence coding for part or all of the protective antigen isolated from *Boophilus microplus* can be used in DNA hybridization experiments to identify related DNA sequence from other species of ticks. These latter DNA sequences can be constructed by genetic engineering techniques to obtain the expression by bacterial or eukaryote cells such as yeast, plant, insect, tick or mammalian cell lines of all or parts of the antigen from other species of ticks and provide an effective vaccine against those tick species which are responsible for morbidity or economic losses to man or morbidity and productivity losses to animals.

The invention also provides recombinant DNA molecule which comprises at least one DNA sequence according to the invention and vector DNA.

In a preferred form the vector DNA comprises plasmid, phage or viral DNA.

Preferred vectors include lambda gt11, pUR290, pUR291, pUR282, pUK270, pUC8, pUC9, baculovirus, pZipNeo, an SV40 based vector, lambda gt10, an EMBL vector, pBR327, pBR329, and pBR329 containing a par locus.

The invention further provides a transformant cell line, said transformant carrying at least one recombinant DNA molecule according to the invention.

In a further embodiment the invention provides a vaccine comprising at least one immunogen according to the invention together with a pharmaceutically acceptable carrier, adjuvant, immunopotentiator or diluent.

In accordance with the present invention an antigen derived from a tick species which antigen is capable of inducing a highly significant degree of immunity to tick challenge when used to vaccinate cattle has been purified and characterised. Further, bacterial cells which contain DNA sequences derived from a tick species have been produced and those bacterial cells which contain DNA sequences encoding portions of the tick protective antigen have been identified. The DNA sequence of the tick gene encoding that antigen has been determined, the resulting DNA sequence has been used to identify further bacterial cells containing related genes from other species of ticks. Expression of the antigen or portions of the antigen by bacteria or other microorganisms or by eukaryotic cells such as yeast, insect, tick, plant and mammalian cells grown in vitro provides a large amount of the antigen effective as an immunogen for the protection of cattle and other domestic animals against infestation by *Boophilis microplus* and other tick species.

The invention also includes within its scope the epitope or the epitopes of immunogens of the invention which are responsible for the protective immune response. These epitopes may be created artificially by the synthetic production of oligopeptides which contain sequences of portions of the protective antigen which can be predicted from the results of immunochemical tests on fragments of the protective antigen produced in bacteria or generated as a result of chemical or enzymatic cleavage of the native or recombinant peptides and includes relevant epitopes from those protective antigens, oligopeptides, idiotypes and anti-idiotypes which resemble or recognise those epitopes which may have protective effects when used to actively or passively immunise animals.

In a further embodiment the invention provides methods for the purification of immunogens according to the invention and particularly protective antigens derived from ticks.

The invention provides a process for the preparation of an immunogen according to the invention which process comprises a chromatographic step performed on wheat germ lectin or on a lectin having the same or similar terminal sugar specificity as wheat germ lectin.

Preferably the invention provides a process for the preparation of an immunogen according to the invention said process comprising extracting membrane enriched fractions obtained from homogenised ticks with detergent and subjecting the solubilised material to wheat germ lectin sepharose chromatography and elution with N-acetylglucosamine or chromatography using a lectin having the same or similar terminal sugar specificity to wheat germ lectin.

Preferably said detergent is selected from NP40, an NP40 derivative, Zwittergent 3–14 or SDS.

The process may further comprise Concanavalin-A sepharose chromatography and elution with methyl-α-D-mannopyranoside, a preparative isoelectrofocussing step or size exclusion chromatography.

In a preferred form said methods include preparation of an homogenate of ticks, centrifugation to produce membrane enriched fractions, treatment of those membranes with detergents such as Zwittergent 3–14, chromatography of the detergent soluble material on lectin affinity columns such as wheat germ lectin-Sepharose 6B columns, separation of the lectin binding antigens by isoelectric focusing in buffers containing detergent such as Zwittergent 3–14, chromatography of these antigens by size exclusion HPLC on columns such as Bio-Sil TSK 4,000 and PP 300 SW columns in series in buffers containing detergents and analysis of various fractions produced by SDS-polyacrylamide gel electrophoresis.

The invention also provides an immunogen produced by a process according to the invention. Included within the scope of an immunogen produced by a process according to the invention are those immunogens produced as a result of purification schemes performed on native materials and recombinant or synthetic immunogens produced as a result of recombinant DNA or chemical synthetic methods respectively.

In a further embodiment, the invention provides examples of methods for the treatment of the purified antigens with proteolytic enzymes such as endo lys-C, the purification of oligopeptide fragments produced as a result of proteinase digestion by HPLC chromatography on columns such as Aquapore RP-300 C-8 or Aquapore RP-318 columns and determination of the amino acid sequence of some of the oligopeptides so produced and purified.

The invention further provides the peptide sequence information for such peptide fragments including:

| FRAGMENT NUMBER |
| --- |
| F1 (SEQ ID NO: 1) |
| (K) D P D P G K |
| F2 (SEQ ID NO: 2) |
| (K) W Y E D (G) V L E A I (X) T S I G K |
| F3 (SEQ ID NO: 3) |
| (K) (X) Q A C E (H) P I G E (W) C M M Y P K |
| F4 (SEQ ID NO: 4) |
|         (C) |
| (K) E A G F V Q K |
| F5 (SEQ ID NO: 5) |
|     (S)     (V)     (V) (I) |
| (K) G (P) (D) G Q (C) I N (A) (C) K |
| F6 (SEQ ID NO: 6) |
|     (G) |
| (K) A (D) V S T N E N E Q L E Q A D K |
| F7 (SEQ ID NO: 7) |
|     (G) |
| (K) S (D) T Q (X) I D H I S K |
| F8 (SEQ ID NO: 8) |
|   N    (A) (A) |
| (K) D Q E (Y) (Y) Y |
| F9 (SEQ ID NO: 10) |
| [(K) C P C D N M Y F N A A E E I G C I E] |
|     A N Q C P P D T R R G E I G C I E |
| F10 (SEQ ID NOS: 11 and 12) |
| [(K) A P R Q N M Y F N A A E E I G C I E] |
| [C N C D C P P D T R P G E I G C I E] |
| F11 (SEQ ID NO: 13) |
| (K) W Y E D R V L E A I R T S I G K |
| F12 (SEQ ID NO: 14) |
| (K) E S S I C X D F G N E F C R N A E C E V V P |
| F13 (SEQ ID NO: 15) |
| (K) T R E C S Y G R C V E S N P S K |
| F14 (SEQ ID NO: 16) |
| (K) A Y E C T C P R A F T V A E D G I S/H C K |
| F15 (SEQ ID NOS: 17–19) |
| [(K) D E V D N A S/HL V C Q N A ] |
| [(K) N V L Q S D G     C G P   Y ] |
| [(K) C L N P R P/L R     L K   H/S] |
| F16 (SEQ ID NO: 20) |
|     S |
| (K) A X V L C E X P |
|     C |
|     G |
| F17 (SEQ ID NO: 21) |
| (K) — Q A C E H P I |

NOTE:
Amino acids which were ascribed with low confidence are bracketed.
X indicates no amino acid could be ascribed to this position;
[ ] denotes mixed sequences.

In a preferred embodiment of the invention, these peptide sequences are:

| | |
|---|---|
| F1 (SEQ ID NO: 1) | K D P D G K |
| F2, F11 (SEQ ID NO: 13) | K W Y E D R V L E A I R T S I G K |
| F3, F17 (SEQ ID NO: 22) | K L Q A C E H P I G E W C M M Y P K |
| F4 (SEQ ID NO: 23) | K E A G F V C K |
| F5 (SEQ ID NO: 24) | K G P D G O C I N A C K |
| F6 (SEQ ID NO: 25) | K A G V S C N E N E Q S E C A D K |
| F8 (SEQ ID NO: 26) | K D Q E A A Y K |
| F9, F10 (SEQ ID NOS: 27–29) | K C P R D N M Y F N A A E K |
| | K A N C Q C P P D T K P G E I G C I E |
| | K A N C Q C P P D T R P G E I G C I E |
| F12 (SEQ ID NO: 30) | A E S S I C S D F G N E F C R N A E C E V V P G |
| F13 (SEQ ID NO: 15) | K T R E C S Y G R C V E S N P S K |
| F14 (SEQ ID NOS: 31 and 32) | K A Y E C T C P S G S T V A E D G I T C K |
| | K A Y E C T C P R A F T V A E D G I T C K |
| F15 (SEQ ID NO: 33) | K N L L Q R D S R C C Q |
| F16 (SEQ ID NO: 34) | K G T V L C E C P |

The invention also provides examples of methods which can be used to design from the amino acid sequence data oligonucleotide sequences which are suitable for use as hybridization probes to identify nucleic acids sequences (DNA or RNA) coding for the polypeptide containing those amino acid sequences, methods for the construction of bacterial cells containing complementary DNA and genomic DNA fragments from ticks, the use of the oligonucleotides to identify bacterial cells containing complementary and genomic DNA fragments coding for that antigen, the DNA sequence of one such cDNA fragment, methods by which recombinant DNA technology can be used to produce bacterial or eukaryote cells which synthesize the protein or parts of that protein and methods for culturing those cells and for purification of the tick antigen or parts thereof to be incorporated into effective vaccines against ticks.

In a preferred model, the mechanism of action of the vaccine is one in which an immune response is generated in vaccinated animals which results in ticks feeding on those animals ingesting components of the host immune system such as antibodies which interact with the surface of tick gut cells and either alone, or together with other factors in the host blood such as components of complement result in damage occuring such as lysis of the tick gut cells which in turn results in the ticks becoming unable to effectively digest blood, the tick gut becoming permeable to host blood components, to such an extent that host blood components such as albumin, haemoglobin, immunoglobulin and blood cells can be identified in the haemoloymph of the ticks and the ticks appear red in colour. This gut damage in turn results in the death of the majority of the ticks feeding on vaccinated animals before they reach engorgement stage and those few which may survive are so badly damaged that their engorgement weight is decreased and/or reproductive capacity is impaired (6,7,8).

The invention also relates to antibodies generated against epitopes on the antigens according to the invention (so called idiotype antibodies) and to antibodies generated against the variable region of those first antibodies, (so called anti-idiotype antibodies) which mimic the protective epitopes on the antigen and may be used as effective vaccines in either passive protection of animals (idiotypes) or active immunization of animals (anti-idiotypes) and thereby result in effective protection.

BRIEF DESCRIPTION OF THE DRAWINGS

FIGS. 6–6(2) show the DNA sequence for the WGL+ gene (bases 1–2012 of SEQ ID NO:55 and SEQ ID NO:56).

FIG. 8 shows the translated amino acid sequence (residues 11–688 of SEQ ID NO:57) for the WGL+ antigen deduced from the DNA sequence.

FIGS. 8A–8B show a restriction enzyme map for part of the WGL+ gene showing an example of the expression strategy.

FIGS. 11–11(2) show the DNA sequence (SEQ ID NO:58) for the YBm017 gene and the translated amino acid sequence deduced from the DNA sequence (SEQ ID NO:59). YBm017 is an Australian isolate (Yeerongpilly, Queensland) of *Boophilus microplus*.

FIGS. 12–12(2) show the DNA sequence (SEQ ID NO:60) for the YBm22M8 gene and the translated amino acid sequence (SEQ ID NO:61) deduced from the DNA sequence. YBm22M8 is an Australian isolate (Yeerongpilly, Queensland) of *Boophilus microplus*.

FIGS. 13–13(2) show the DNA sequence (SEQ ID NO:62) for the Bm023 gene and the translated amino acid sequence deduced from the DNA sequence (SEQ ID NO:63). Bm023 is another Australian isolate of *Boophilus microplus*.

FIGS. 14–14(2) show the DNA sequence (SEQ ID NO:64) for the Vbm021 gene and the translated amino acid sequence deduced from the DNA sequence (SEQ ID NO:65). VBm021 is a Venezuelan isolate of *Boophilus microplus*.

FIGS. 15–15(2) show the DNA sequence (SEQ ID NO:66) for the MexBm86 gene and the translated amino acid sequence deduced from the DNA sequence (SEQ ID NO:67). MexBm86 is a Mexican isolate of *Boophilus microplus*.

FIG. 17 shows a partial DNA sequence (SEQ ID NO:68) for the Ra442 gene and the translated amino acid sequence deduced from the DNA sequence (SEQ ID NO:69). Ra442 is a *Rhipicephalus appendiculatus* isolate.

BEST MODE OF CARRYING OUR THE INVENTION

Figure 1:
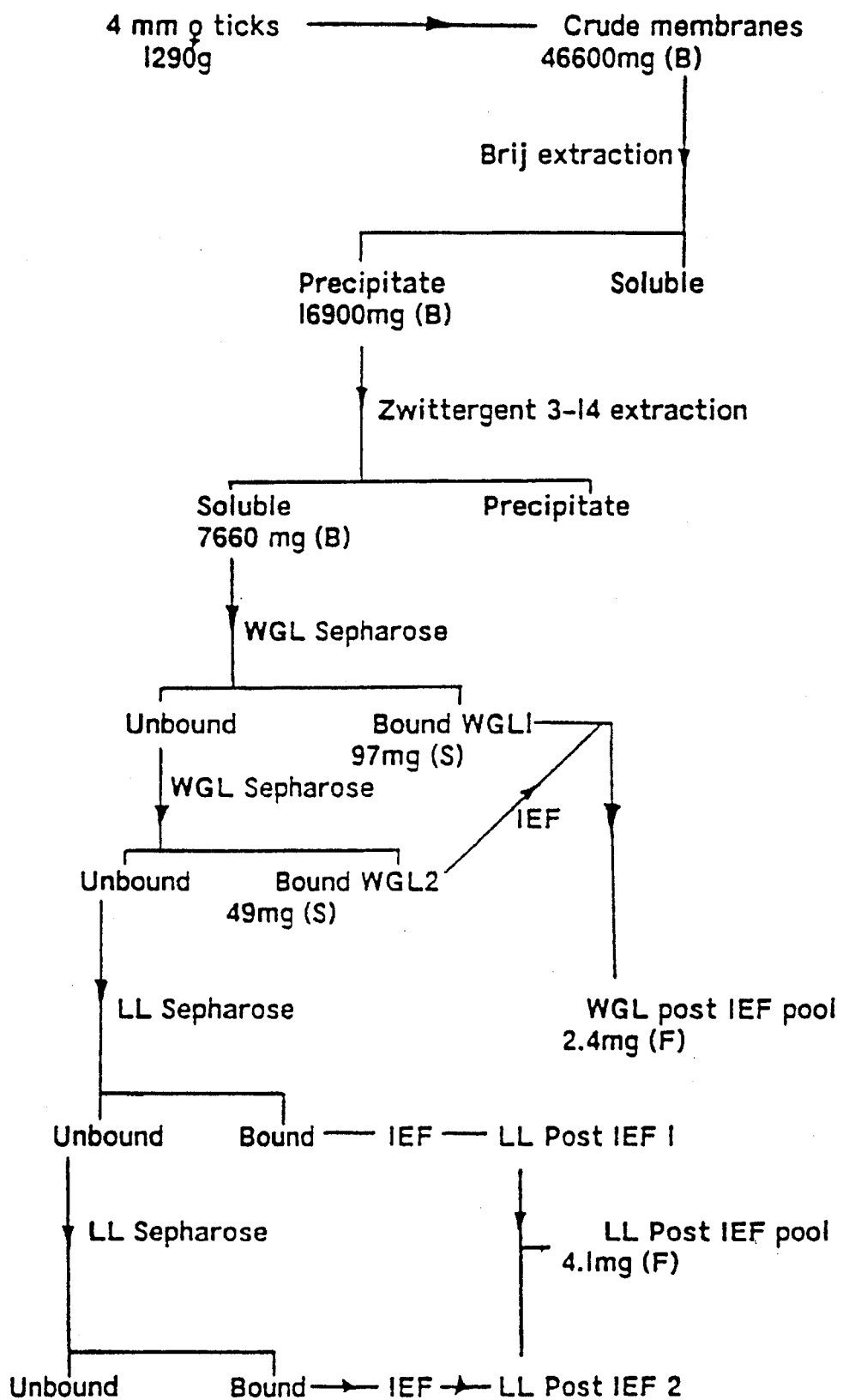
FIG. 1 is a schematic representation of the method for the isolation of the "WGL post IEF pool" and "LL Post IEF pool".

The invention is further described in the following examples which are illustrative of the invention but in no way limiting on its scope.

| SOURCE OF REAGENTS | |
|---|---|
| Sephacryl | Pharmacia |
| Sepharose 6 MB | Pharmacia |
| Zwittergent 3–14 | Calbiochem |
| Sephadex | Pharmacia |
| Brij 35 | Sigma |
| Bio-gel | Bio Rad |
| Cyanogen Bromide | Sigma or Ajax |
| Sarkosyl | Sigma |
| Endoproteinase lys-c | Boehringer |
| Triflouroacetic acid | Pierce |
| HFBA | Pierce |
| Acetonitrile | Mallinckrodt |
| Columns for HPLC | Waters, BioRad, Beckman |
| Poly U Sepharose | Collaborative research |
| Oligo dT cellulose | Collaborative research |
| dATP, dCTP, dGTP and dTTP | Boehringer |
| $^{32}$P-labelled deoxynucleic acid triphosphates | Amersham |
| Spermidine | Calbiochem |
| PEI cellulose | Merck |
| Concanavalin A-Sepharose | Pharmacia |
| CNBr-Sepharose | Pharmacia |
| Other chemicals used were of reagent grade. | |

| ABBREVIATIONS | |
|---|---|
| HPLC | High performance liquid chromatography |
| SDS | Sodium dodecylsulfate |
| EDTA | Ethylenediaminetetraacetic acid |
| WGL | Wheat germ lectin |
| WGL 1 | Wheat germ lectin bound antigen pool 1 |
| WGL 2 | Wheat germ lectin bound antigen pool 2 |
| WGL$^+$ | Wheat germ lectin bound antigen |
| WGL$^-$ | Wheat germ lectin unbound |
| IEF | Iso electric focussing |
| LL | Lentil lectin |
| LL$^+$ | Lentil lectin bound antigen |
| LL$^-$ | Lentil lectin unbound |
| HEPES | N-2-Hydroxyethylpiperazine-N$^1$-2-ethane-sulfonic acid |
| Endo lys C | Endoproteinase lys C |
| DTT | dithiothreitol |
| pI | isoelectric point |
| HFBA | heptafluorobutytic acid |
| BSA | bovine serum albumin |
| MMLV | murine maloney leukemia virus |
| dNTP | deoxy nucleotide triphosphate |
| dATP | deoxy adenosine triphosphate |
| dCTP | deoxy cytidine triphosphate |
| dGTP | deoxy guanidine triphosphate |
| dTTP | deoxy thymidine triphosphate |
| d(GCT)TP | a mixture of dGTP, dCTP, and dTTP |
| NAD | nicatinamide adenine dinucleotide |
| ATP | adenosine triphosphate |
| PEI | polyethyleneimine |
| BRL | Bethesda Research Laboratories |
| IBI | International Biotechnologies Inc. |
| A260, A280 | Absorbance at 260 or 280 nm |
| cDNA | Complementary DNA |
| ds | double stranded |
| g | gram |
| $g_{av}$ | average gravity units |
| m,μ,n,p (prefixes) | milli, micro, nano, pico |
| M | Molar |
| l | liter |
| U | Units of activity (restriction enzymes) |
| bp | base pairs |

-continued

| | |
|---|---|
| Kb | Kilobase pairs (thousand base pairs) |
| TLC | Thin layer chromatograph |
| ELISA | enzyme linked immunoabsorbent assay |

| BUFFERS | |
|---|---|
| 10 × 1st strand | 0.5M Tris pH 7.5<br>0.75M KCl<br>0.03M $MgCl_2$ |
| 5 × 2nd strand (RNase H) | 0.2M Tris pH 7.5<br>0.05M $MgCl_2$<br>0.1M $(NH_4)_2SO_4$<br>1M KCl<br>1.5 mm B-NAD |
| 10 × Methylase Buffer | 0.5M Tris pH 7.5<br>0.01M EDTA |
| 10 × TA Buffer | 0.33M Tris-Acetate pH 7.9<br>0.66M K-Acetate<br>0.1M Mg-Acetate |
| 5 × Kinase Buffer | 0.05M Tris pH 7.5<br>0.05M Mg $Cl_2$<br>0.05M DTT<br>0.5 mM Spermidine |
| 10 × Ligation Buffer | 0.3M Tris pH 8<br>17 mM EDTA<br>70 mM $MgCl_2$<br>10 mM ATP<br>0.1M DTT<br>20 ug/ml BSA<br>1 mM Spermidine |
| 10 × High Salt Buffer | 1M NaCl<br>0.5M Tris pH 7.5<br>0.1M $MgCl_2$<br>10 mM DTT |
| 10 × S1 Buffer | 0.3M NaAcetate pH 4.4<br>2.5M NaCl<br>10 mM $ZnCl_2$ |
| TE | 10 mM Tris pH 7.5<br>1 mM EDTA |
| PEI cellulose buffer | 0.75M $KH_2$ $PO_4$ pH 3.5 |
| Buffer A | 0.05M Tris<br>0.03M acetic acid<br>0.1M NaCl |

TEAB buffer

TEAB is a solution of triethylamine equilibrated to pH 7 by bubbling $CO_2$ through the solution. It is prepared as a 1M stock solution which is stored at 4° C. The pH is checked before use, the solution being re-equilibrated with a $CO_2$ pellet if required.

EXAMPLE 1

(a) Demonstration that at least some of the protective antigens are glycoproteins.

Since the majority of plasma membrane proteins are glycoproteins, initial attempts at further characterization of the protective antigen(s) focussed on lectin affinity.

It was found that wheat germ lectin and Concanavalin A bound to several components of tick antigen preparation B4/B5. Thus it appeared that a number of antigens in the tick preparation bear terminal N-acetylglucosamine residues and it is recognised that wheat germ lectin could be replaced in the purification scheme by other lectins with the same or similar terminal sugar specificity.

Approximately 2.1 mg of antigen B4/B5 purified by the narrow range isoelectric focussing procedure (described in Australian Patent Application No. 45936/85) was applied to a column of WGL-Sepharose 6 MB (14) in 0.05M Tris chloride buffer, 1% Zwittergent 3–14, pH 8 and washed with the same buffer. Bound glycoproteins were then eluted with 100 mg/ml N-acetylglucosamine in the same buffer. Bound and unbound material was used to immunize sheep (Two vaccinations in Freunds incomplete adjuvant using five sheep per group). Induced immunity was estimated by applying freshly moulted adult ticks to the sheep and measuring the success of engorgement by the proportion of female ticks which finally engorged, relative to the number attached to the sheep skin three days after initial application of the young adults (Table 1).

TABLE 1

Immunization of Sheep with Glycoprotein Preparations

| Group | Percentage of Ticks Engorging | | | | |
|---|---|---|---|---|---|
| Controls | 100, | 100, | 100, | 100, | 100 |
| Material not binding to WGL | 100, | 6, | 93, | 100, | 100 |
| Material binding to WGL | 0, | 93, | 0, | 83, | 28 |

It is clear that some animals in each vaccinated group were highly protected from tick challenge. Serum was obtained from each sheep in this experiment after vaccination but before tick challenge and the antibody titres of each serum sample against the antigens used in the vaccine were measured by radioimmunoassays. The animals in each group which showed tick damage had high antibody titres against the antigen preparation injected whereas those which had low titres allowed large numbers of ticks to engorge without any visible signs of damage (data not shown). It appears that protective antigens were present in both fractions used in this experiment but failure to observe tick damage with some animals was due to the failure of those animals to respond vigorously to vaccination for reasons which are currently unclear.

(b) In a subsequent experiment with sheep, fraction GF5 and 6, the more highly purified gel filtration fractions (Australian Patent Application No. 45936/85) were chromatographed on a WGL-sepharose affinity column and the specifically bound and the unbound material was used to vaccinate sheep in a similar way to that described above. Again, for some animals in each group, the immune response generated by vaccination with either fraction was capable of producing damage to ticks feeding on those animals as demonstrated by the lower numbers of viable ticks recovered from the sheep (% surviving), the percentage of those ticks where were red in colour (% damage) and the lower weight of those ticks which survived or engorged (Table 2).

(c) An experiment similar to that described above was performed in which cattle were vaccinated with material which had specifically bound and material which failed to bind to a WGL-Sepharose column (Table 3). Again, the immune response generated by both fractions following vaccination gave indications of damage to ticks feeding on vaccinated cattle. The material which failed to bind to the WGL-Sepharose column was particularly effective in this experiment.

TABLE 3

| Group | Animal No. | Tick No. | % Damage | Weight (mg) |
|---|---|---|---|---|
| Controls | 943 | 239 | 2 | 226 |
| | 944 | 190 | 7 | 216 |
| | 957 | 282 | 1 | 245 |
| WGL bound | 945 | 214 | 22 | 202 |
| | 960 | 125 | 64 | 183 |
| | 962 | 188 | 5 | 218 |
| WGL unbound | 938 | 19 | 84 | 148 |
| | 950 | 10 | 97 | 164 |
| | 959 | 25 | 92 | 140 |

NOTE: Tick no. in this and subsequent experiment refers to the average number of engorged female ticks dropping from each animal per day. Three weeks after vaccination, cattle are challenged with approximately 1000 larvae per day for a period of at least 16 days. When the ticks mature and engorged female ticks are observed, the engorged female ticks are collected each day and counted for a period of at least 16 days. This number is averaged over that period and presented in the Tick no. column. On each day during this period, the number of ticks which are visibly damaged are scored (red ticks) and that proportion listed in the % damage column. The average weight of the engorged females is also determined.

(d) Concurrently with this experiment, the material which had specifically bound to the WGL-sepharose column was fractionated on SDS polyacrylamide gels. Silver stains of these gels showed two major staining components which were excised (fractions S2 and S4) and these, as well as the intermediate portions of the gels (fractions S1, S3, S5 and S6) were used to vaccinate cattle. The most highly protective fraction was S2 (Table 4) which corresponds to one of the bands observed in stained gels which has an apparent molecular weight of approximately 80–90 kilodaltons in this gel system compared with Pharmacia and BRL molecular weight markers.

In this experiment, the number of ticks surviving on the cattle vaccinated with S2 was reduced compared with the other groups (Tick No column—the average number of engorged adult female ticks dropping from each animal per day over the 21 day period studied). In addition, the majority of the surviving ticks were red or appeared to be otherwise

TABLE 2

| Group | Animal No. | Number of Ticks Surviving/Number Applied | % Surviving Ticks | % Damage | Mean Weight |
|---|---|---|---|---|---|
| Controls | 181 | 36/40 | 90% | 0 | 254 |
| | 182 | 45/50 | 90% | 4 | 224 |
| | 183 | 32/40 | 80% | 3 | 214 |
| WGL unbound | 121 | 27/40 | 67.5% | 19 | 182 |
| | 122 | 27/40 | 67.5% | 41 | 179 |
| | 123 | 30/40 | 75% | 3 | 223 |
| WGL bound | 124 | 27/40 | 67.5% | 52 | 156 |
| | 125 | 7/40 | 17.5% | 100 | 11 |
| | 180 | 9/40 | 22.5% | 100 | 11 |

In particular the material which was specifically bound to the affinity column is to be characterized herein but the protective antigens in the unbound fraction are also clearly capable of giving protection.

abnormal when examined visually (% damage) and the weight of those surviving ticks in the S2 group was reduced compared to the ticks from the animals in the other groups (Table 4).

TABLE 4

| Group | Animal No. | Tick No. | % Damage | Weight |
|---|---|---|---|---|
| S1 | 947 | 196 | 10 | 215 |
|  | 951 | 194 | 1 | 230 |
|  | 963 | 243 | 30 | 198 |
| S2 | 941 | 115 | 66 | 147 |
|  | 942 | 86 | 87 | 150 |
|  | 953 | 173 | 32 | 192 |
| S3 | 961 | 166 | 3 | 212 |
|  | 967 | 240 | 4 | 243 |
|  | 968 | 193 | 4 | 233 |
| S4 | 939 | 163 | 1 | 229 |
|  | 940 | 155 | 4 | 229 |
|  | 952 | 149 | 9 | 258 |
| S5 | 937 | 276 | 3 | 248 |
|  | 955 | 232 | 2 | 225 |
|  | 956 | 160 | 5 | 221 |
| S6 | 946 | 269 | 12 | 222 |
|  | 954 | 157 | 19 | 297 |
|  | 958 | 281 | 1 | 245 |

(e) In vitro experiments were conducted in which a range of lectins were tested to determine which were capable of reacting with the material not retained on the WGL-sepharose column. Lentil lectin was found to be reactive and therefore the material not bound to the WGL-Sepharose was fractionated on a lentil lectin column (15). Cattle were vaccinated with these fractions, and the immune response generated against the material not bound to WGL-sepharose but bound to the LL-sepharose was found to result in some small indication of damage to ticks feeding on vaccinated cattle (Table 5). SDS gel analysis of this fraction shows a band which has a molecular weight which is in the same range as the S2 antigen identified in the previous experiment.

TABLE 5

| Group | Animal No. | Tick No. | % Damage | Weight |
|---|---|---|---|---|
| Controls | 990 | 195 | 0.7 | 252 |
|  | 980 | 220 | 0.7 | 243 |
|  | 979 | 248 | 0.6 | 252 |
| WGL unbound | 1006 | 183 | 6.2 | 196 |
| LL unbound | 1002 | 188 | 0.3 | 233 |
|  | 988 | 185 | 30.8 | 197 |
| WGL unbound | 1001 | 270 | 3.9 | 244 |
| LL bound | 996 | 267 | 1.1 | 252 |
|  | 994 | 249 | 16.1 | 206 |

Both fractions used in this experiment were capable of generating an immune response which was capable of giving some indication of protection in this experiment.

The lentil lectin chromatography step produced a far greater yield of material having a similar molecular weight to the S2 antigen than was produced by the wheat germ lectin chromatography step.

This similarity in molecular weight and difference in lectin affinity suggested that the molecules may have been related by a common peptide backbone but differed in glycosylation.

This was later disproved (Example 2g).

Due to the presumed similarity to S2 and greater abundance of the LL bound material it was proposed that this material be used as a starting material for further purification.

However, subsequent poor vaccination results with this material in the light of good vaccination results with WGL bound material (Example 3) and demonstrated differences in amino acid composition have led to further purification schemes and cloning schemes being developed for the S2 or WGL[+] material.

EXAMPLE 2

Knowing from the above results the iso-electric point, molecular weight and lectin binding characteristics of the major protective antigen (referred to above as S2), a number of experiments were performed in order to improve the efficiency of the isolation procedure. The following method has been devised which yields at least 10 times more of the S2 antigen (later referred to as the wheat germ lectin bound antigen, WGL[+] antigen or WGL[+]) and lentil lectin bound antigen (later referred to as the LL[+] antigen or LL[+]) than the methods described in Australian Patent Application No. 45936/85.

The procedure is outlined in the flow charts (FIGS. 1, 2, 3, and 4).

Improvement of the Procedures for Isolation of the Major Protective Antigen (a) Isolation and Extraction of Tick Membrane and Particulate Material 1290 grams of semi-engorged adult female *Boophilus microplus* were picked from cattle on the day prior to the completion of engorgement. They were homogenised in 0.05M Tris, 0.025M acetic acid, 0.1M sodium chloride, 1 mM EDTA, the homogenate strained through fine gauze and the retained material, which was mostly cuticle fragments, was rinsed with buffer. A total of 3 ml of buffer per gram of ticks was used in the extraction. The suspension of tick material was then mixed with 350 mg phenylmethanesulfonyl fluoride per liter and centrifuged at $600\times g_{av}$ for 15 min. The supernatant was then centrifuged at $20,000\times g_{av}$ for 30 min and the supernatant from that, centrifuged for $100,000\times g_{av}$ for 1 h. Precipitates were collected from each of these centrifugation steps and frozen at $-20°$ C. until used.

The $600\times$ g, $20,000\times$ g and $100,000\times$ g precipitates were thawed, suspended in buffer A (0.05M Tris, 0.03M acetic acid) and the protein concentration was measured. The suspension was diluted in buffer A containing Brij 35 to final protein and detergent concentrations of 5 and 10 mg/ml respectively. The tick material was extracted at $37°$ C. for 1 h then centrifuged at $3,300\times g_{av}$ for 30 min at $20°$ C. The precipitate was resuspended in buffer A and the protein concentration re-assayed. Extraction was repeated at the protein and detergent concentrations used before, substituting Zwittergent 3–14 for Brij 35, while the extraction time was lengthened to 90 min. The suspension was centrifuged as before and the supernatant was retained.

(b) Lectin Affinity Chromatography and Isoelectric Focussing (FIG. 1)

The supernatant from the Zwittergent 3–14 extraction, (3255 ml), was stirred with 90 ml of WGL Sepharose for 16 h at $20°$ C., filtered and the WGL-Sepharose conjugate was poured into an $18\times2.5$ cm column, washed with buffer A containing 1% Zwittergent 3–14 then eluted in buffer A containing 1% Zwittergent 3–14 and 100 mg/ml N-acetylglucosamine. Fractions were pooled on the basis of the A280 absorption of specifically eluted material to give wheat germ lectin bound pool 1 (WGL1).

The adsorption of the detergent supernatant with WGL-Sepharose and subsequent elution of bound material was repeated as described above to give WGL2. The two eluates were then pooled (WGL pool).

The WGL pool was dialysed against 2×2.5 liters of water, then against 0.05M Tris-chloride buffer pH 7.5 containing 0.1M ammonium thiocyanate. Concanavalin A-Sepharose (Pharmacia) was poured as a 2.5×11 cm column and washed in buffer containing 0.05M Tris, 1% Zwittergent 3–14, 0.1 mM calcium chloride, 0.1 mM manganese chloride, 0.1M ammonium thiocyanate, adjusted to pH 7.5 with hydrochloric acid. The WGL pool was loaded on this column, washed and the specifically bound material was eluted in the same buffer to which had been added 50 mg/ml methyl-α-D-mannopyranoside. Fractions were pooled, dialysed against water then subjected to preparative isoelectricfocussing.

Isoelectricfocussing was carried out in a flat bed of IEF Sephadex containing 1% (w/v) Zwittergent 3–14 and Pharmalyte 4–6.5 diluted 1 to 15 (v/v) for 10,000 Vhr. Individual fractions were analysed by SDS gel electrophoresis. The required protein appeared to be present in fractions with pI's of 5.3 to 5.7 though, for the sake of better purification, only those fractions with pI's of 5.4 to 5.6 were pooled to give "WGL post IEF pool".

The Zwittergent 3–14 soluble material left after the second extraction with WGL-Sepharose was mixed with 70 ml of LL-Sepharose and stirred for 24 h at 20° C., the suspension was filtered and the collected Sepharose conjugate was poured as a 2.5×14 cm column. This was then washed with Tris-acetate, 1% Zwittergent 3–14 buffer and eluted in the same buffer containing 50 mg/ml methyl-α-D-manno-pyranoside. Fractions were pooled on the basis of their A280 and dialysed against water. Further fractionation was carried out by preparative isoelectric focussing using the conditions already described for material which bound to WGL. Fractions were analysed by SDS polyacrylamide gel electrophoresis. The protein being isolated focussed over a pI range of 4.8 to 5.2 though the fractions which were pooled for further purification covered the range of 4.8 to 5.0.

The LL unbound material from the first affinity chromatography was readsorbed to LL-Sepharose and the material specifically eluted with methyl-α-D-mannopyranoside was separated by IEF. Material with the same pI range of 4.8 to 5.0 was pooled, then the products of the two experiments mixed to give "LL post IEF pool".

The method for the isolation of "WGL post IEF pool" and "LL post IEF pool" is shown schematically in FIG. 1.

Figure 2:
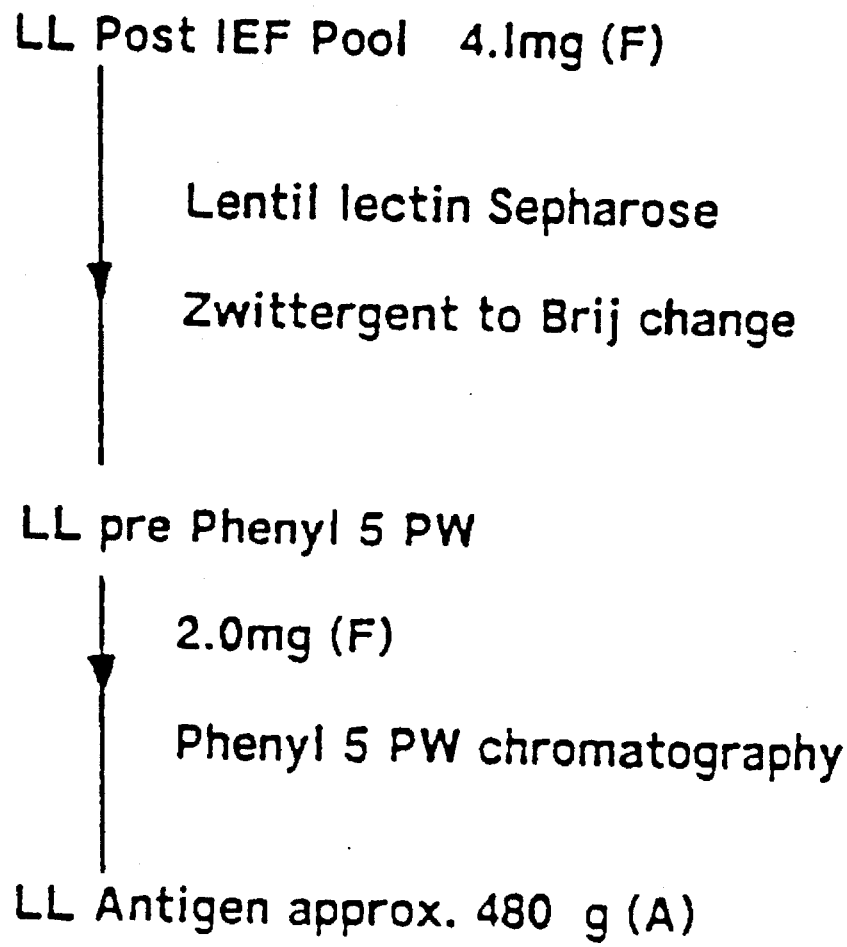
FIG. 2 is a schematic representation of the fractionation procedure for the isolation of "LL+ antigen".

(c) Hydrophobic Chromatography of LL Post IEF Pool (FIG. 2)

A 1.6×6.5 cm column of LL-Sepharose was equilibrated in 0.1M Tris-acetate buffer, 1% Zwittergent 3–14 pH 8.0. The "LL post IEF pool" was adjusted to pH 7.1 and applied to this column which was subsequently washed with buffer, then with 0.1M Tris-acetate buffer, 0.1% Brij pH 7.5. Bound material was then eluted with 0.1M Tris-acetate-Brij buffer containing 50 mg/ml methyl-α-D-mannopyranoside.

Eluted material was dialysed against 0.1M Tris-acetate-Brij buffer then ammonium sulfate was added to a final concentration of 0.5M. The sample was applied to a 7.5×75 mm TSK phenyl-5-PW column which had been equilibrated in 0.1M Tris-acetate, 0.5M ammonium sulfate, 0.1% Brij, pH 7.5 and, after washing, the column was resolved with a linear gradient from this starting buffer to a buffer containing 0.1M Tris-acetate, 0.1% Brij pH 7.5. Fractions were analysed by SDS gel electrophoresis and those containing the required protein pooled to give "LL$^+$ antigen" or LL$^+$.

This procedure is shown schematically in FIG. 2.

Figure 3:
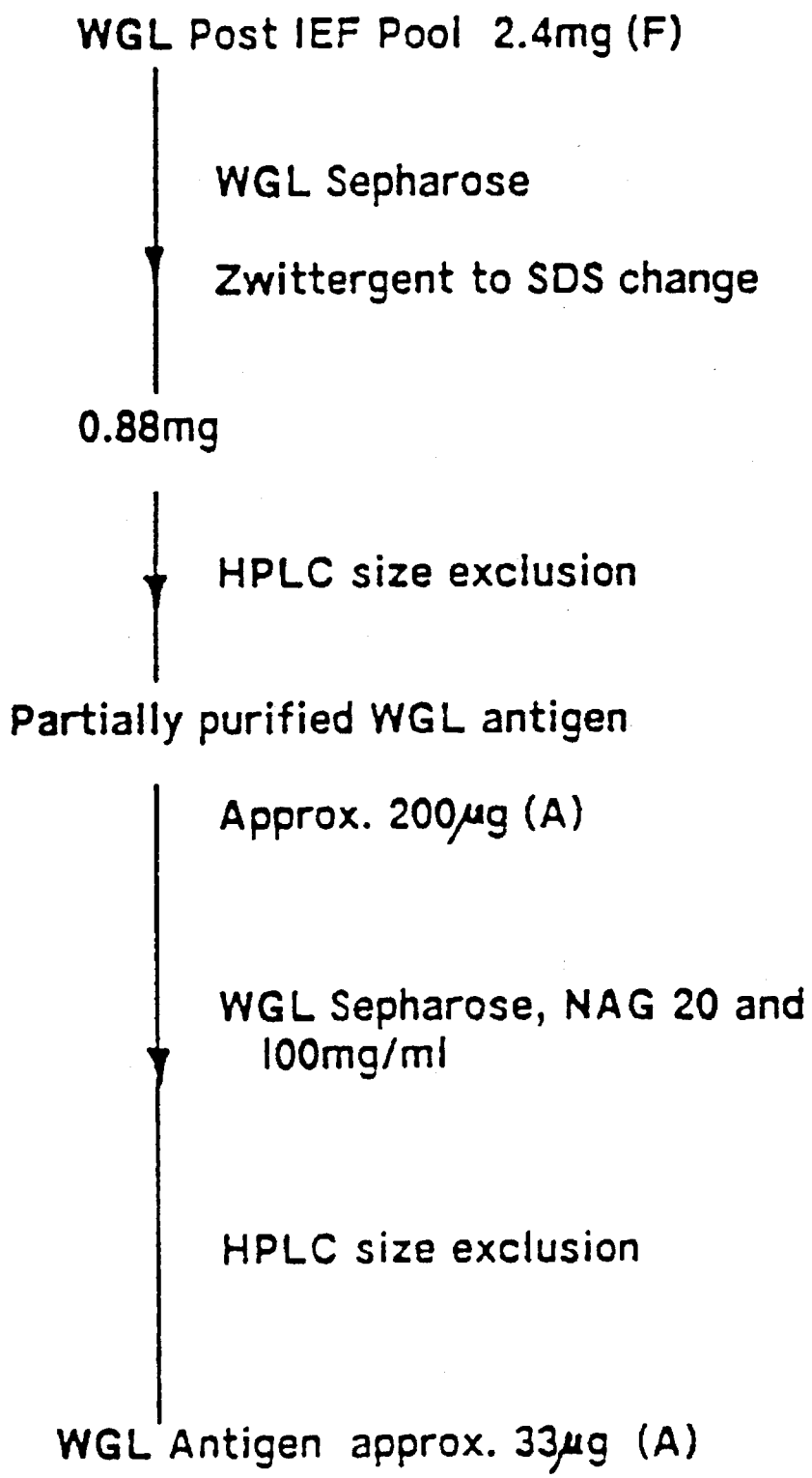
FIG. 3 is a schematic representation of the fractionation procedure for the isolation of "WGL+ antigen".
Figure 4:
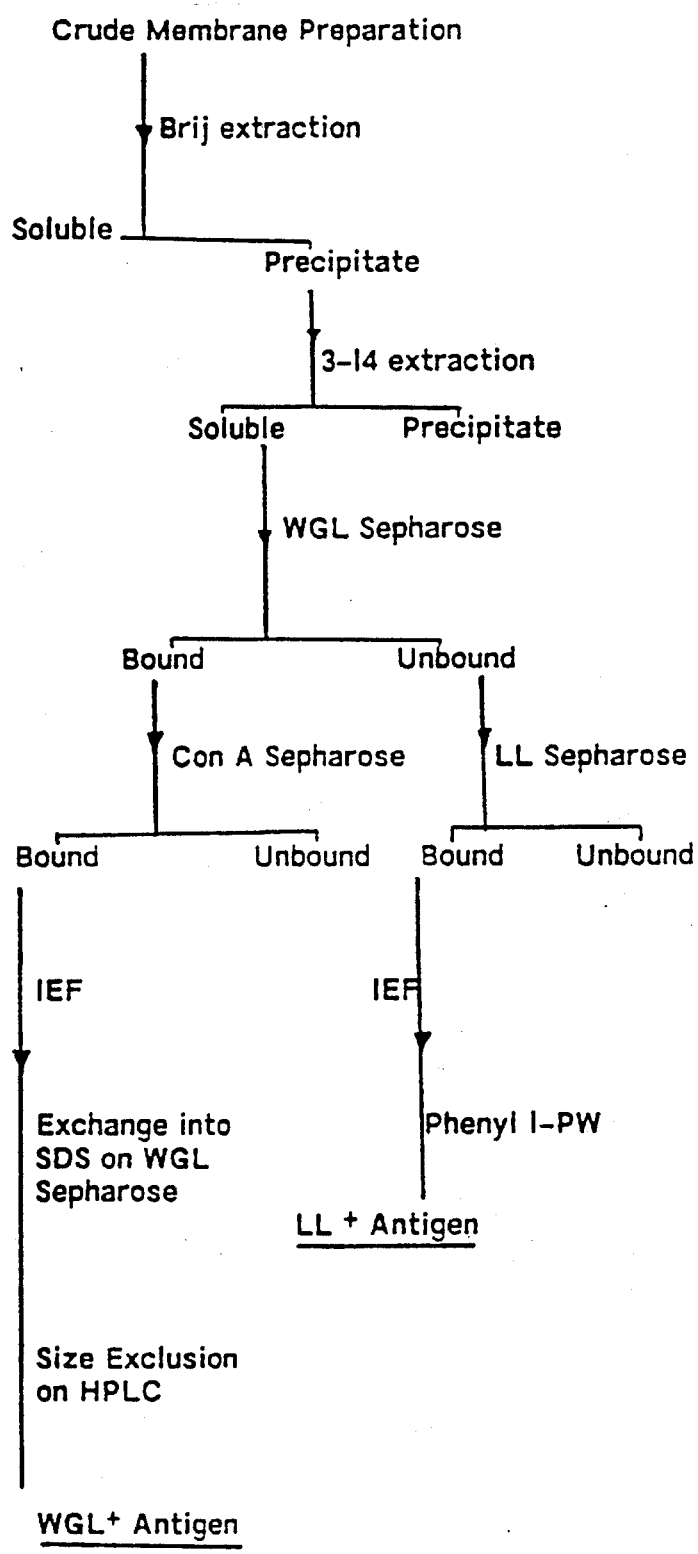
FIG. 4 is a simplified schematic representation of the purification procedure for the isolation of WGL+ and LL+ antigens.

(d) Size Exclusion Chromatography of WGL Post IEF Pool (FIG. 3)

The pH of the "WGL post IEF pool" was increased to 7.3 and the material then loaded on a column of WGL-Sepharose equilibrated in 0.05M Tris-chloride, 0.2% Zwittergent 3–14 pH 7.5. The column was washed with 0.05M Tris-chloride, 0.1% SDS, then bound material eluted in Tris-chloride-SDS buffer containing 100 mg/ml N-acetylglucosamine. Fractions were analysed by SDS electrophoresis and those containing the required protein pooled, dialysed against 0.05M Tris-chloride buffer pH 7.5 and concentrated on a Savant Speedvac.

Size exclusion chromatography was carried out using a Waters HPLC system and, in sequence, an Si200 Polyol guard column (Serva, Heidelberg), a 7.5×30 cm Bio-Sil TSK 4000 and a 7.5 mm×30 cm PP 300 SW (Waters). Chromatography was carried out in a buffer containing 0.05M HEPES, 0.1M sodium thiocyanate, 0.1% SDS, the pH adjusted to 7.0 with sodium hydroxide, at a flow rate of 1 ml/min and a column temperature of 37° C. In this system, bovine serum albumin had an elution time of 13.8 min and ribonuclease A of 17.7 min. Fractions were analysed by SDS gel electrophoresis. The material of interest was found to elute from the HPLC column at between 14.0 and 15.0 min and these fractions were pooled.

The product of this step still contained some impurity of lower molecular weight. It was therefore loaded on a 0.6×10 cm column of WGL-Sepharose in 0.05M Tris-chloride, 0.1% SDS pH 7.5, washed in this buffer, then the bound material was eluted in the same buffer containing firstly 20 mg/ml then 100 mg/ml N-acetylglucosamine. Fractions were analysed by SDS gel electrophoresis and pooled on a basis of the amount and purity of the desired protein in each. They were concentrated and re-chromatographed on HPLC size exclusion chromatography as described above. The final pool of fractions containing the desired antigen ("WGL$^+$ antigen") was made after analysis by SDS gel electrophoresis as described above.

This procedure is shown schematically in FIG. 3.

(e) Protein Determination

Four methods of protein determination were used during antigen isolation, the methods being chosen on a basis of sensitivity required and the nature of expected interfering substances. These methods, and the abbreviations used for them in FIGS. 1, 2 and 3 were:

1. Biuret method; abbreviated (B)
2. Spectrophotometric method, from A280 and A260 measurements; abbreviated (S).
3. Fluorescence method, from the integrated fluorescence of high molecular weight material after derivatization with o-phthalaldehyde; abbreviated (F).
4. Absorbance method, based on the integrated A280 from HPLC chromatographic runs, assuming that a 1 mg/ml solution of the protein in a 1 cm light path had an absorbance at 280 nm of 1; abbreviated (A).

(f) Comments on the Isolation Procedure

The major residual problem with the procedure described above is that in some preparations of the WGL$^+$ antigen, a contaminant of lower molecular weight was observed as judged by SDS polyacrylamide gel electrophoresis. This contaminant could be partially, though not entirely, removed by repeating the affinity chromatography on WGL-Sepharose in SDS buffer and elution at two concentrations of N-acetylglucosamine.

The amounts of this impurity are variable from preparation to preparation. In a subsequent antigen isolation it was present in minor amounts and good antigen purity was obtained after pooling fractions with pI's in the range 5.30 to 5.67 on preparative isoelectricfocussing, followed by a single HPLC size exclusion chromatography. The yield of WGL$^+$ antigen was thus higher (approximately 300 μg from 1.3 kg of ticks).

Figure 5A:
FIGS. 5A and 5B show purity of the WGL+ antigen.
Figure 5B:
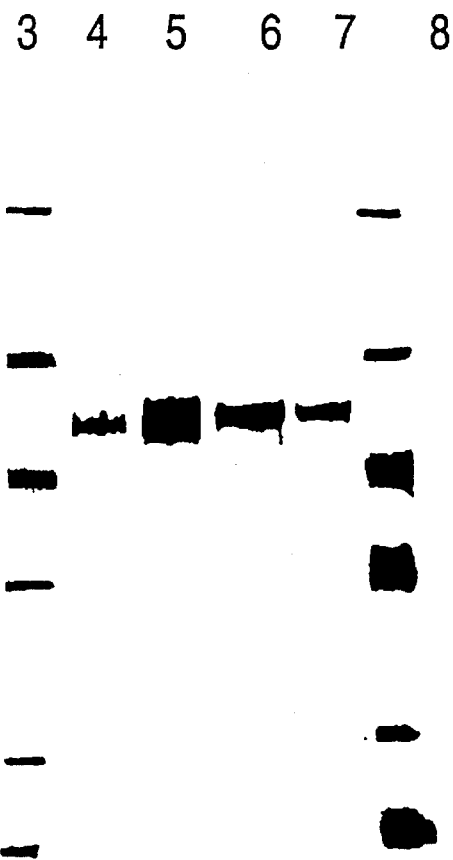

FIG. 5 shows SDS-polyacrylamide gel profiles of fraction GF5/6, the starting material in this work, (lane 2) and of the purified WGL$^+$ antigen (lanes 4 & 5) and LL$^+$ antigen (lanes 6 & 7) together with appropriate molecular weight markers (lanes 1, 3 & 8). It is clear from these gels that the GF 5/6 fraction is very impure and contains a large number of components in addition to the WGL$^+$ antigen which is in fact such a minor component that it can not be distinguished from the other components in the fraction. The WGL$^+$ and LL$^+$ antigens are highly purified. In lane 5 which is an overloaded sample of WGL$^+$ antigen, a small amount of the contaminating material at lower molecular weight can just be seen.

(g) Amino Acid Composition of WGL$^+$, and LL$^+$ Antigens

Samples of the WGL$^+$ and LL$^+$ antigens isolated by the new purification procedure were analysed by amino acid analysis. The HPLC plots and calculated amino acid compositions derived from the HPLC printout by integration of the areas under each peak (Table 6) indicate that the antigens have different amino acid compositions. In addition the antigens clearly have different terminal sugar residues accounting for the different lectin binding characteristics.

TABLE 6

Amino Acid Compositions of Tick Antigens (mole %)

|     | WGL$^+$ Antigen | LL$^+$ Antigen |
| --- | --- | --- |
| Asp | 7.4 | 11.0 |
| Glu | 6.8 | 10.3 |
| Ser | 9.7 | 7.4 |
| Gly | 7.4 | 10.5 |
| His | 2.9 | 2.9 |
| Arg | 5.0 | 5.2 |
| Thr | 9.0 | 5.6 |
| Ala | 9.1 | 6.8 |
| Pro | 5.9 | 5.2 |
| Tyr | 4.8 | 3.9 |
| Val | 7.9 | 6.5 |
| Met | 1.9 | 2.9 |
| Cys | 1.4 | 0.5 |
| Ile | 4.7 | 4.5 |
| Leu | 6.6 | 8.8 |
| Phe | 4.1 | 4.0 |
| Lys | 5.4 | 3.8 |

NOTES:
Trp is destroyed in this assay. The results presented are obtained from samples taken after 24, 48 and 72 hours of acid hydrolysis.

EXAMPLE 3

Vaccinal Activities of WGL$^+$ and LL$^+$ Antigens

Samples of WGL$^+$ antigen (21 µg) and LL$^+$ antigen (400 µg) were homogenised in Freunds Complete adjuvant and used to vaccinate cattle (1/10 of each preparation per animal per vaccination) as described in Australian Patent Application No. 45936/85. Vaccinated animals, together with control cattle were challenged with ticks and the numbers of engorged female ticks dropping from the experimental animals was monitored over a 16 day period (Table 7). It is clear that cattle vaccinated with very small amounts of WGL$^+$ antigen were strongly protected from infestation in that the number of ticks dropping from each animal per day was reduced, the weight of the surviving ticks was lower and a high proportion of the surviving ticks were visibly damaged as a result of gut damage allowing cattle blood components to pass into the haemolymph of the ticks (% Red column). In addition, the ticks which survived on the cattle vaccinated with the WGL$^+$ antigen had a greatly reduced capacity to produce eggs compared to the control animals.

TABLE 7

| Animal No. | Wt. eggs/ Wt. Ticks | Antigen | Tick No. | Tick Wt. | % Red |
| --- | --- | --- | --- | --- | --- |
| 26 | 0.49 | Controls | 199 | 224 | 6 |
| 29 | 0.52 |  | 237 | 231 | 3 |
| 31 | 0.47 |  | 227 | 220 | 1 |
| 28 |  |  | 269 | 223 | 9 |
| 36 |  | WGL$^-$ | 186 | 228 | 3 |
| 40 |  | LL$^-$ | 170 | 199 | 4 |
| 27 |  |  | 272 | 224 | 2 |
| 35 |  | LL$^+$ antigen | 338 | 262 | 0 |
| 37 |  | (130 µg) | 238 | 233 | 1 |
| 30 | 0.16 |  | 25 | 152 | 86 |
| 32 | 0.25 | WGL$^+$ antigen | 135 | 175 | 79 |
| 34 | 0.22 | (7 µg) | 38 | 152 | 70 |

The LL$^+$ antigen at a higher dose failed to give significant protection to the cattle despite the fact that the cattle had mounted a strong immune response to the vaccine as determined by ELISA [data not shown].

Both WGL$^+$ and LL$^+$ antigens appeared to be largely pure by SDS gel electrophoresis (FIG. 5) and both have similar molecular weights of approximately 89 kd in the gel system used compared to the BRL molecular weight standards used.

The new purification procedure outlined above is an improvement over that used previously giving a yield of 33–300 µg WGL$^+$ antigen compared with approximately 3 µg of "S2" antigen per 1.29 kg tick starting material. It is asserted that these two antigens (WGL$^+$ and S2) are the same glycoprotein based on similar molecular weight, isoelectric point, lectin binding properties, amino acid composition and vaccinal efficacy.

EXAMPLE 4

Digestion of WGL$^+$ antigen with endoproteinase lys-C, separation of oligopeptides, determination of the amino acid sequence of oligopeptides and design of oligonucleotide sequences suitable as hybridization probes to detect recombinant organisms containing DNA sequences coding for the WGL$^+$ peptide.

Approximately 40 µg of WGL$^+$ antigen purified as described in Example 2 was mixed with 100 µl of 0.1M Tris-chloride buffer pH 8.3 containing 20 mM dithiothreitol and 2% ($^w$/v) SDS, then incubated at 56° C. for 30 min. The solution was then cooled to room temperature and sodium iodoacetate added to a final concentration of 0.14M. After 45 min. in the dark, cold methanol was added in a ratio 9:1 methanol:sample ($^v$/v). The sample was stored at −20° C. overnight, centrifuged, the supernatant removed and the precipitate dried.

The precipitate was then dissolved in 76 µl of 0.1M Tris-chloride buffer containing 4M urea, pH 8.5, then 4 µl of endo lys C (6 units per ml) was added. After 2 hrs at 37° C., another 4 µl of enzyme was added and the digestion was continued for a further 17 hrs.

The digest was applied directly to an Aquapore RP-300 C-8 column in 0.1% trifluoroacetic acid and peptides were eluted in a linear gradient from 0–60% $^v$/v acetonitrile/water in 0.1% trifluoroacetic acid. If necessary, peptides were rechromatographed in the same solvent system using an Aquapore 318 column. Peptides were collected, concentrated to 50–100 µl by rotary dessication in a rotary evaporator. The amino acid sequences of the oligopeptides were determined using an Applied Biosystems amino acid sequencer. The following peptide sequences were obtained. The one letter and 3 letter codes used for amino acids are shown in Table 8.

Fragment Number

F1(SEQ ID NO:1) (K)[1] D P D P G K (20-mer oligonucleotide)

F2(SEQ ID NO:2) (K)[1] W Y E D (G)[2] V L E A I (X)[3] T S I G K (50-mer oligonucleotide)

F3(SEQ ID NO:3) (K)[1] (X)[4]Q A C E (H)[2] P I G E (W)[2] C M M Y P K (53-mer oligonucleotide) (C)[5]

F4(SEQ ID NO:4) (K)[1] E A G F V Q K (23-mer oligonucleotide)

In addition, the following peptide sequences were deduced from mixed sequences which may assist in the characterization of the clones although there is a great deal of uncertainty in some of these sequences (especially F7).

TABLE 8

| amino acid | three letter code | one letter code |
| --- | --- | --- |
| alanine | ala | A |
| arginine | arg | R |
| asparagine | asn | N |
| aspartic acid | asp | D |
| cysteine | cys | C |
| glutamic acid | glu | E |
| glutamine | gln | Q |
| glycine | gly | G |
| histidine | his | H |
| isoleucine | ile | I |
| leucine | leu | L |
| lysine | lys | K |
| methionine | met | M |
| phenylalanine | phe | F |
| proline | pro | P |
| serine | ser | S |
| thrionine | thr | T |
| tryptophan | trp | W |

```
                  (S)    (V)  (V) (I)
F5 (SEQ ID NO: 5) (K) G (P) (D) G Q (C) I N (A) (C) K (G)
F6 (SEQ ID NO: 6) A (D) V S T N E N E Q L E Q A D K (G)
F7 (SEQ ID NO: 7) S (D) T Q (X)5 I D H I S K (N)     (A) (A)
F8 (SEQ ID NO: 8) (D) Q E (Y) (Y) Y

F9 (SEQ ID NOS: 35 and 36) [(K)1 C P C D N M Y F N A A E K          ]6
                           [(K)1 A N R Q C P P D T R R G E I G C I E]6
```

Oligonucleotides may be prepared using these amino acid sequences.
For example the following could be used.[7]

20-mer (SEQ ID NO: 37) 5'T T A C C T G G A T C T G G A T C C T T3'

50-mer (SEQ ID NO: 38) TTA CCA ATG GAT GTA CAA ATA GCT TCA AGG ACA CCA TCT TCG TAC CAC TT

```
                                                                                    T
53-mer (SEQ ID NO: 39) TTTGGGTACATCATACACCATTCACCAATTGGGTGTTCACAAGCCTGAGGCTT
                                                                                    AC
```

NOTES:
The following assumptions were made in interpreting the peptide sequences and in designing oligonucleotides probes:
Numbers 1–6 refer to superscripts in the peptide sequence listed above.
1. It was assumed that a lysine (K) preceded the first amino acid which was determined for each peptide based on the specificity of the endo lys-C.
2. These amino acids were assumed to be correct although they were detected at lower molar ratios than expected.
3. No amino acid could be confidently ascribed to the positions shown as X.
4. This position contained a number of amino acids. For the design of oligonucleotides, the correct amino acid was assumed to be either D, A or L but may be another.
5. More than one amino acid was detected in some sequences. The uncertainty is denoted by brackets.
6. These sequences were mixed (square brackets) and the relative molar abundance of the amino acids detected was approximately the same in each cycle.
7. A number of approaches known in the art can be used to design oligonucleotides suitable for use as hybridization probes. For example inosine base can be incorporated in positions where a number of deoxyribonucleotides are used in the third positions of redundant codons. The reverse complementary sequences to those presented can also be used equally well as hybridization probes. In the examples shown the codon usage was based on the sequence for the mRNA coding for the brine shrimp elongation factor (12).

TABLE 8-continued

| amino acid | three letter code | one letter code |
|---|---|---|
| tyrosine | tyr | Y |
| valine | val | V |

EXAMPLE 5

Approximately 40 μg of WGL$^+$ antigen was digested with endo lys-C as described in Example 4. The digest products were applied to an Aquapore RP-300 C-8 column in 0.1% heptafluorobutyric acid (HFBA) and peptides were eluted in a linear gradient from 0–60% acetonitrile/water in 0.1% HFBA. Selected fractions were then re-chromatographed on Aquapore RP-300 C-8 or C-18 columns using trifluoroacetic acid in place of HFBA. The most symmetrical fractions were analysed for the presence of amino acids by hydrolysis of one tenth of the sample in hydrochloric acid vapour, derivatization with O-phthalaldehyde followed by reverse phase separation on HPLC and detection by fluorescence. The remaining portions of the samples were dessicated to 50–100 μl volumes in a rotary evaporator and the amino acid sequence was determined using an Applied Biosystems amino acid sequencer.

The following peptide sequences were obtained.

F10 is the sequence of the same mixture of two peptides as analysed for F9. It is surprising that these two oligopeptides co-purified on both occasions as the peptide fractionation procedure was different in the two examples.

F11 and F2 are likely to be the same fragment as the only differences are that the two uncertain amino acids in the F2 sequence are both R in the F11 sequence. A larger amount of material was present in F11 so this sequence is likely to be correct.

F17 and F3 appear to be sequences of the same peptide. F3 could be read further as more material was present but F17 contained less impurities so the first residue could be identified.

From these amino acid sequences, oligonucleotides can be prepared which would be suitable for screening cDNA and genomic DNA banks to identify the gene coding for the WGL$^+$ antigen. The following examples could be used (see note 7 in Example 4. In the following examples, the third position in the codons was chosen to minimise secondary structure, not on brine shrimp usage as used in Example 4).

```
                              FRAGMENT NUMBER

F10 (SEQ ID NOS: 40 and 41) [(K) A P R Q N M Y F N A A E K         ]
                            [(K) C N C D C P P D T R P G E I G C I E]

F11 (SEQ ID NO: 13) (K) W Y E D R V L E A I R T S I G K

F12 (SEQ ID NO: 42) (K) E S S I C X D F G N E F C R N A E C E V V P (K) 72-mer
                                    64 × 17-mers F13 (SEQ ID NO: 15) (K) T R E C S Y G R C V E S N P S K              51-mer F14 (SEQ ID NO: 16) (K) A Y E C T C P R A F T V A E D G I S/H C K    63-mer
                    64 × 17-mers

[(K) D E V D N A  S/H L V C Q N — A ]
F15 (SEQ ID NOS: 17–19) [(K) N V L Q S D   G         C G P     Y ]
                            [(K) C L N P R P/L R      L K      H/S]

S
F16 (SEQ ID NO: 20) (K) A X V L C E X P
                        C
                        G

F17 (SEQ ID NO: 21) (K) L Q A C E H P I
```

NOTES:
It was assumed that a lysine precedes each fragment (K). X indicates that no amino acid could be confidently ascribed to the position during the peptide sequencing. F10 and F15 were mixtures of two and three peptide fragments repectively (denoted by [ ]).

72-mer (SEQ ID NO: 43)
5' TTT AGG TAC AAC CTC ACA TTC AGC ATT CCT ACA AAA TTC ATT ACC GAA ATC
AAA ACA AAT ACT ACT CTC CTT 3'

51-mer (SEQ ID NO: 44)
CTT CGA CGG ATT GGA TTC GAC GCA TCT GCC ATA GCT ACA TTC CCT CGT
CTT 3'

63-mer (SEQ ID NO: 45)
CTT GCA ATG GAT TCC ATC CTC GGC GAC AGT GAA AGC TCT AGG GCA AGT GCA
CTC ATA AGC CTT 3'

In addition, degenerate shorter oligonucleotides could be synthesized. For example 64 fold degenerate 17-mer oligonucleotides could be designed using the sequence DFGNEF from the F12 sequence and from the sequences KAYECT and YECTCP from the F14 sequence. 16 fold degenerate 17-mer oligonucleotide mixtures could also be designed using the sequence CMMYPK from the amino acid sequence of F3 shown in Example 4. These short degenerate sequences may be useful to confirm that clones isolated using long oligonucleotides contain the desired DNA sequences coding for the $WGL^+$ antigen.

EXAMPLE 6

Genetic Engineering of the $WGL^+$ (S2) Antigen

The major limitation to the development of commercial vaccines using the $WGL^+$ antigen is the limited availability of $WGL^+$ material which can be obtained from natural sources. Means by which this limitation can be overcome include the construction by genetic engineering techniques of bacteria, yeast or other readily cultivated cells including mammalian or insect cell lines which synthesize large amounts of all or part of the $WGL^+$ antigen. There are several means by which this goal can be achieved but they basically fall into a small number of steps which, by means of example only, are set out below.

In order to identify the recombinant organisms which contain the tick genetic information coding for the protein backbone of the $WGL^+$ antigen, appropriate reagents must first be generated. These may be antibodies from animals vaccinated with the purified protective antigen or with partially purified preparations containing that antigen preferably following denaturation of the antigen with a suitable detergent such as SDS. Bacterial yeast or other cells which synthesize part or all of the $WGL^+$ antigen must then be constructed and screened with the antiserum.

Preferably the $WGL^+$ antigen is isolated in sufficient quantities in order to determine the amino acid sequence of the protein portion of the antigen or of fragments of the antigen produced as a result of endoproteolytic enzyme digestion using enzymes such as trypsin, endo lys C or pepsin or by chemical cleavage of the peptide using reagents such as cyanogen bromide. Fragments produced as a result of these treatments are separated and isolated using methods known in the art such as fractionation by HPLC reverse phase liquid chromatography or HPLC on columns containing hydrophobic resins, ion exchange resins or size fractionation resins. Preferably reverse phase resins such as C1, C8 or C18 are used singly or consecutively depending on the characteristics of the fragments produced as a result of the enzymatic or chemical treatment chosen.

Fragments of the $WGL^+$ peptide produced as a result of these treatments are then analysed on a gas phase amino acid sequenator using methods known in the art. From the amino acid sequence and the known DNA sequences which encode each amino acid, oligonucleotide sequences can be prepared which are complementary to the DNA sequence coding for the antigen and these can be used in hybridisation experiments to identify recombinant organisms containing the DNA coding for the antigen. The DNA sequence of these reacting clones can then be determined to confirm that the sequence is the one of interest. The DNA sequence can then be used to design the best means by which the microorganisms can be engineered to manufacture large amounts of the polypeptide.

(a) Construction of Gene Libraries

Readily cultivated microorganisms which contain the genetic information coding for the $WGL^+$ protective antigen can be constructed using synthesised DNA which is complementary to the RNA isolated from the appropriate developmental stage of ticks or using DNA fragments isolated from any stage of ticks, preferably eggs or larvae as they will not contain bovine blood.

If antibody probes are the only reagents available for detection of the clones containing the $WGL^+$ antigen, cDNA or genomic DNA libraries must be constructed in a phage, viral or plasmid system which would result in the expression of the tick antigen or parts thereof. Such vectors include lambda gt11, bacterial plasmids such as pUR290, pUR291, pUR282, pUK270, pUC8, pUC9 or eukaryotic viral vectors such as the baculovirus, pZipNeo, or SV40-based vectors.

If oligonucleotide probes are available, clone libraries can be constructed using cDNA or genomic DNA fragments in a larger range of phage, plasmid and viral systems including, for example, lambda gt10, EMBL vectors, or plasmid vectors such as pBR327, pBR329 or pBR322.

Preferably cDNA libraries are generated since smaller numbers of clones have to be screened and any problems with expression through introns are avoided. Ideally the developmental stage of ticks which synthesis maximum levels of the $WGL^+$ antigen are first identified. If antibodies are the only means available to do this, in vitro translation of RNA isolated from ticks of various ages followed by immunoprecipitation of the translation products with antibodies and analysis by SDS gel electrophoresis and fluorography enables the identification of the most suitable stage of ticks for extraction of RNA for construction of cDNA banks. The apparently low abundance of the $WGL^+$ protein makes this approach very difficult. If oligonucleotides are available, hybridisation to the RNA isolated from ticks of various ages should enable the identification of the RNA source containing the highest abundance of mRNA coding for the $WGL^+$ antigen.

RNA can be isolated from ticks and cDNA synthesized and cloned a number of methods known in the art can be used. The following methods are outlined by means of example only.

(b) Ethanol Precipitation

In the following methods, ethanol precipitation involves adding to the solution of nucleic acid, one tenth of the solution volume of 3M sodium acetate and three to four volumes of absolute ethanol. The mixture is then stored at −20° C. for at least 2 hrs or at −70° C. or in an ethanol/dry ice bath until the solution becomes viscous. The mixture is then centifuged usually at 12,000× $g_{av}$ for at least 10 minutes. The supernatant is carefully removed and the pellet containing the nucleic acid material (as well as other macromolecules) is used in further manipulations.

(c) Ethanol Precipitation from 2M Ammonium Acetate

In high salt solutions (e.g. 2M ammonium acetate), the majority of unincorporated deoxynucleotide triphosphates (and other small molecular weight material) will remain in the supernatant after an ethanol precipitation. The procedure is as described above except an equal volume of 4M ammonium acetate is added to the solution instead of the sodium acetate followed by 3–4 volumes of ethanol before cooling as described above.

(d) Phenol or Phenol/chloroform Extraction

Phenol or phenol/chloroform extraction involves the addition to the nucleic acid solution of an equal volume of redistilled phenol or a 1:1 (v/v) mixture of phenol and chloroform equilibrated with 0.1M Tris pH 8. The contents of the tube are mixed and the phases separated by centrifugation. The upper (aqueous) phase is removed to a fresh tube and the phenol or phenol/chloroform is discarded. Usually the aqueous phase is re-extracted and then extracted with ether to remove remaining phenol. Optionally the phenol or phenol chloroform phase from the first extraction may be re-extracted by addition of TE, mixing and centrifugation. In this case, the two aqueous phases would be combined before ether extraction and further processing.

(e) PEI Cellulose TLC

To monitor incorporation of radioactive dATP into nucleic acids during the various reactions in this procedure, thin layer chromatography on PEI cellulose was performed in 0.75M phosphate buffer pH 3.5. An aliquot of material to be monitored is applied toward one end of a strip of PEI cellulose and, after the chromatogram is resolved, the strip is exposed to an X-ray film. Following development of the autoradiograph, the areas of the PEI cellulose strip containing radioactivity are cut, placed in vials and the radioactivity in each determined by Cherenkov counting in a scintillation counter. The proportion of the radioactive material at the origin of the chromatograph can be used to determine the success of the reaction. This procedure is referred to as PEI cellulose chromatography.

(f) Extraction of DNA and RNA

High molecular weight DNA and RNA are isolated from ticks picked from the host at different developmental stages. Ticks are homogenised at room temperature in an Omni-mixer for 2–3 minutes in a buffer containing guanidine isothiocyanate (4.7M), Sarkosyl (7.4%), Tris (5 mM) and β-mercaptoethanol (70 mM). The homogenate is centrifuged at 4° C. at 14,000× $g_{av}$ for 10 minutes. Solid CsCl is added to the homogenate (1 g/2.5 ml) which is layered onto a CsCl cushion (2.5 g/ml) and centrifuged for 48 hours at 25,000 rpm in a SW28 rotor (Beckman). The upper layer is aspirated, the DNA band recovered and the RNA pellet recovered, precipitated with ethanol, washed several times with 70% ethanol and stored in TE at −70° C. until used.

Polyadenylated mRNA can be isolated by passage over oligo dT cellulose columns or poly U Sepharose columns using methods described by the manufacturers (Collaborative Research).

(g) cDNA Synthesis

Several methods can be used for the construction of cDNA banks in phage or plasmid vectors. The following method by means of example only is a modification of the "RNase H" method for construction of cDNA banks in lambda gt11. The method is outlined schematically in FIG. 6.

(h) First Strand Synthesis

2 μg of poly A⁺RNA is dissolved in TE. Water is added to give a final volume of 25 μl. The solution is heated at 70° C. for 3 minutes then rapidly cooled on ice. To the cooled solution is added 5 μl 10×1st Strand Buffer, 5 μl 0.1M DTT, 5 μl Oligo-dT [Boehringer 100 ng/1 μl], 1.25 μl RNasin [Promega 40 U/μl], 2 μl BSA (5 mg/ml), 5 μl 10 mM d(GCT)TP, 0.5 μl 10 mM dATP and 3 μl M-MLV Reverse transcriptase [BRL 200 U/μl].

2.5 μl of the mixture is transferred to tube A (analytical reaction for monitoring synthesis) and 0.2 μl [$^{32}$P]dATP is added (0.2 μCi).

To the remaining bulk reaction 0.5 μl 50 mM dATP is added. The tubes are incubated for 30 minutes at 42° C. 0.25 μl 10 mM dATP is then added to tube A and the incubations continued for a further 30 minutes. A 0.5 μl sample is taken from tube A and ethanol precipitated for gel analysis. A further 0.2 μl sample is taken from the tube to be monitored by TLC on PEI cellulose.

If all of the 2 μg of RNA added to the reaction was poly A-adenylated, it can be calculated that approximately 30% incorporation of [$^{32}$P]dATP into nucleic acids is equivalent to 100% efficiency in first strand synthesis. Commonly RNA passaged over Oligo-dT cellulose once yields 6–10% incorporation.

To prepare a sample to monitor the second strand reaction, 2.5 μl of the bulk reaction is removed and precipitated with ethanol from 2M ammonium acetate. The sample is washed twice with 70% ethanol then resuspended in 2.5 μl 1×1st Strand Buffer in tube B.

(i) Second Strand (RNase H)

A solution of; 28 μl of water, 10 μl 10× RNase H Buffer; 1 μl 5 mg/μl BSA, 1.25 μl 10 mM d(GCT)TP, 0.5 μl 10 mM dATP, 1.6 μl RNase H [BRL 20 U/μl], 5 μl DNA Polymerase 1 [holoenzyme (Biolabs) 100 U/μl] and 2 μl *E. coli* DNA ligase, is prepared.

The solution is mixed, then 2.5 μl is dispensed into Tube B with 0.2 μl [$^{32}$P]dATP, 1.8 μl is dispensed into Tube A and the remainder is dispensed into the bulk reaction tube. 0.75 μl of 10 mM dATP is added to the bulk reaction tube. The three tubes are incubated at 15° C. for 60 minutes, then at 22° C. for a further 60 minutes.

A 0.2 μl sample from tube B is chromatographed on PEI cellulose to monitor the reaction. A further sample from tube B is ethanol precipitated from 2M ammonium acetate for gel analysis. The tube A sample from the first strand synthesis and the tube B second strand synthesis sample are run on a 1.5% agarose gel to determine the size of the cDNA which has been synthesized.

To prepare a sample to monitor the T₄ polymerase reaction, 0.5 μl is taken from the bulk reaction tube and placed in Tube C.

The remaining contents of Tubes A and B are pooled with the bulk reaction. The contents of both the bulk reaction, and Tube C are extracted with phenol/chloroform (1:1), precipitated with ethanol from 2M ammonium acetate and the precipitates are washed twice with 70% ethanol.

(j) EcoR1 Methylation

A solution of 29.5 μl of water, 4 μl 0.1M DTT, 2 μl 10× EcoR1 Methylase buffer, 4 μl 1 mM S-adenosyl methionine [Biolabs] and 0.5 μl EcoR1 Methylase [Biolabs 20 U/μl] is prepared in a fresh tube. 2 μl of the mix is dispensed into Tube C and the remainder into the bulk reaction tube. The two tubes are incubated at 37° C. for 30 minutes then at 70° C. for a further 15 minutes then cooled in ice.

In a fresh tube, the following buffer is prepared: 4 μl 10× TA buffer, 2 μl 5 mg/ml BSA, 1.4 μl 0.1M DTT, 2 μl $T_4$ DNA polymerase [Biolabs 1 U/μl] and 29.5 μl of water. 2 μl is added to tube C which is then incubated at 37° C. for 10 minutes. 0.5 μl of a solution containing 10 mM d(GCTA)TP is added to the remainder of the solution and this is added to the bulk reaction tube which is then incubated at 37° C. for 50 minutes, 70° C. for 15 minutes then ice quenched.

To Tube C 0.2 μl of each of 50 μM d(GTC)TP, [$^{32}$P]dATP [0.2 μCi] and 5 μM dATP are added and incubation is continued at 37° C. for a further 50 minutes, after which time 0.2 μl of the sample is spotted and chromatographed on PEI cellulose.

0.2 μl of 0.2 mM dATP represents approximately three times the amount of dATP required to add 2 adenosine residues to the 5' ends of each molecule, assuming that there was a total of 2 μg of dscDNA of average size of 1 kb synthesized after 2nd strand synthesis.

(k) Kinase

There is some indication that the kinase step is not necessary and can probably be omitted. To the bulk reaction 20 μl 5× Kinase buffer, 0.2 μl 0.1M ATP, and 0.5 μl polynucleotide kinase [Biolabs 4 U/μl] is added. The mixture is incubated at 37° C. for 60 minutes. The reaction is extracted with an equal volume of a phenol/chloroform mixture (1:1), the aqueous phases are pooled, precipitated by ethanol from 2M ammonium acetate then washed twice with 70% ethanol.

(l) Linker Ligation

To monitor the linker ligation reaction, samples are prepared for agarose and polyacrylamide gel analysis.

| Agarose gel: | Samples from bulk reaction ($^{32}$P cDNA) |
| --- | --- |
| Sample 1 | cDNA before ligation to cold linkers |
| Sample 2 | cDNA after ligation to cold linkers |
| Sample 3 | cDNA after ligation to cold linkers and digestion with Eco R1 |
| Polyacrylamide gel: | $^{32}$P linker samples |
| Sample 4 | Tube D $^{32}$P linkers + cDNA before digestion with Eco R1 |
| Sample 5 | Tube D $^{32}$P linkers + cDNA after digestion with Eco R1 |
| Sample 6 | Tube E $^{32}$P linkers alone before digestion with Eco R1 |
| Sample 7 | Tube E $^{32}$P linkers alone after digestion with Eco R1 |

The ligation mixture is prepared by adding to a fresh tube 9 μl EcoR1 linkers [Biolabs 200 ng/μl], and 1.7 μl of DNA ligase [IBI 3 U/μl]. 15 μl of ligation mixture is dispensed into the bulk reaction tube mixed quickly, then a 0.25 μl sample is removed and frozen on dry ice immediately for agarose gel analysis (Sample 1).

A 1 μl sample is taken from the bulk reaction tube and 0.2 μl $^{32}$P labelled EcoR1 linkers is added (Tube D: cDNA+ linkers).

A 1 μl sample is taken from the remainder of the ligation mixture and 0.2 μl $^{32}$P labelled EcoR1 linkers are added (Tube E: linkers alone).

The bulk reaction and tubes D and E are incubated at 25° C. for 4 hours. Samples of 0.25 μl from the bulk reaction tube and 0.6 μl from tubes D and E are removed for agarose or polyacrylamide gel analysis respectively (Samples 2, 4 and 6).

The remainder of the bulk reaction and tubes D and E are heated for 5 hours at 70° C. then cooled on ice.

(m) EcoR1 Digestion

To a fresh tube 11 μl EcoR1 digestion buffer, 2 μl EcoR1 [IBI 18 U/μl] and 82 μl of water are added. 4 μl of the mixture is dispensed into the bulk reaction tube. The three tubes are incubated at 37° C. for 60 minutes. A further 2 μl aliquot of EcoR1 [36 U] is added to the bulk reaction tube and incubation is continued for a further 60 minutes. The remaining samples in tubes D and E are electrophoresed on agarose and acrylamide gels together with the samples taken from tubes D and E above. Autoradiographs of those gels demonstrate whether the reactions have worked.

A 1.4 μl sample is removed from the bulk reaction tube (Sample 3). The remainder of the bulk reaction is extracted with phenol/chloroform.

A 1% agarose gel is run loaded with 0.25 μl each of samples 1, 2 and 3. Samples 4, 5, 6 and 7 are run on a 12% polyacrylamide gel. Both gels are autoradiographed to determine whether all reactions have succeeded.

(n) Separation of Linkers from cDNA

A 1.2×21 cm Sepharose 4B column is equilibrated with 0.1M TEAB. 150 μl samples of EcoR1 digested linkered cDNA are loaded on to the column and fractions collected in TEAB buffer (250–500 μl). Fractions containing cDNA fragments with sizes greater than 600 bp as determined by mobility on agarose or polyacrylamide gels are pooled, evaporated to dryness in a rotary evaporator suspended in TE and ligated to EcoR1 digested and phosphatased lambda gt11 or gt10, packaged in vitro and infected onto suitable host strains such as Y1090 or Y1089 in accordance with suppliers instructions (Promega or Integrated Sciences).

(o) Screening Clones with Oligonucleotides

From the amino acid sequence of the WGL$^+$ protein, peptide fragments derived from chemical cleavage of the WGL$^+$ protein or endoproteolytic digestion peptides derived from the WGL$^+$ protein, oligonucleotides coding for specific portions of the DNA coding for the protein can be designed and used in hybridisation experiments using procedures known in the art. The DNA sequence of hybridising fragments isolated from the library can then be determined and used to design strategies for engineering the gene for expression of the WGL$^+$ protein or portions thereof for incorporation into an effective vaccine.

A cDNA library was constructed in lambda gt 11 using RNA isolated from young adult *B. microplus* which had been feeding on cattle for approximately 16 days. The phage were plated on *E. coli* strain RY1090 and grown at 37° C. for 16 hours. Nitrocellulose filters were placed on the plates and triplicate filters were taken from each plate. The DNA on the filters was denatured and fixed by baking at 80° C. under vacuum. The filters were incubated in prehybridization solution for 2–4 hours and then in hybridization solution for 16 hours essentially as described (10). The hybridization solution contained oligonucleotides which had been labelled with $^{32}$P using polynucleotide kinase (10) and ψ $^{32}$P-ATP (approximately $10^5$ cpm/ml of each oligonucleotide used).

For each set of three filters, two were hybridized to the 63-mer oligonucleotide and the remaining replicate filter was hybridized to a mixture of 51-mer, 72-mer, 50-mer, and 53-mer oligonucleotides. Following washing and autoradiography, plaques which gave rise to signals on all three filters were identified, picked and purified to single plaques.

EXAMPLE 7

Analysis of DNA Sequence of Gene Coding for WGL$^+$ Antigen

The DNA isolated from one clone will be described in detail. This lambda gt11 clone contained three Eco R1 fragments of approximately 4 Kb, 1.5 Kb and 0.3 Kb. Southern hybridization (10) experiments showed that the 4 Kb fragment hybridized to the probes used. This fragment was therefore subcloned into a modified pUC 18 plasmid (giving pBTA 707) in host strain JM101 (recombinant host/plasmid referred to as BTA 1751 ATCC 67548). The 4 Kb fragment was then sonicated and subcloned into M13 mp18 for DNA sequence analysis.

M13 sub-clones were sequenced at random and the complete DNA sequence of the 4 kb inset compiled by assembly of the sequences of the sub-clones by use of an alignment computer program.

FIGS. 6–6(2) show the DNA sequence (bases 1–2012 of SEQ ID NO:55) for the 4 kb DNA fragment and the amino acid sequence (residues 11–688 of SEQ ID NO:56) which can be translated from one region of that DNA sequence into a protein sequence which is identified as the protein backbone of the WGL$^+$ antigen. FIG. 8 shows that amino acid sequence using the one letter abbreviation code for amino acids (Table 8).

The peptide fragments identified during the peptide sequence analysis of endo lys-C digest products from the WGL$^+$ antigen isolated from ticks are identified in FIGS. 6–6(2) (SEQ ID NO:56) and 8 (residues 11–688 of SEQ ID NO:57) by underlines and are tabulated in a summary in Table 9. References to aa numbers correspond to the numbering of amino acid residues shown in FIG. 7 and SEQ ID NO:56.

TABLE 9

| | |
|---|---|
| F1 (SEQ ID NO: 1) | (K) D P D P G K |
| aa 619–625 | K  D P D P G K |
| | |
| F2 (SEQ ID NO: 2) | (K) W Y E D (G) V L E A I X T S I G K |
| aa 357–373 | K  W Y E D  R  V L E A I R T S I G K |
| F11 (SEQ ID NO: 13) | (K) W Y E D  R  V L E A I R T S I G K |
| | |
| F3 (SEQ ID NO: 3) | (K) X Q A C E (H) P I G E (W) C M M Y P K |
| aa 404–421 | K  L Q A C E  H  P I G E  W  C M M Y P K |
| F17 (SEQ ID NO: 21) | (K) L Q A C E  H  P I |
| | |
| F4 (SEQ ID NO: 4) | (K) E A G F V C/Q K |
| aa 212–219 | K  E A G F V  C K |
| | |
| F5 (SEQ ID NO: 5) | (K) G (P) (S/D) G Q (V/C) I N (V/A) (I/C) K |
| aa 199–210 | K  G  P   D G Q  C   I N A    C  K |
| | |
| F6 (SEQ ID NO: 6) | (K) A (D/G) V S (T) N E N E Q (L) E (Q) A D K |
| aa 487–503 | K  A  G V  S   C N E N E Q  S  E C  A D K |
| | |
| F8 (SEQ ID NO: 8) | (K) D Q E ($^A$/Y) $^{N}$ $^A$/Y Y |
| aa 443–450 | K  D Q E  A    A  Y K |
| | |
| F9 a (SEQ ID NO: 27) | (K) C P R D N M Y F N A A E K |
| aa 50–63 | K  C P R D N M Y F N A A E K |
| F10 a (SEQ ID NO: 27) | (K) C P R D N M Y F N A A E K |
| | |
| F9 b (SEQ ID NO: 46) | (K) A N C Q C P P D T R R G E I G C I E |
| aa 513–531 | K  A N C Q C P P D T K P  G E I G C I E |
| F10 b (SEQ ID NO: 29) | (K) A N C Q C P P D T R P  G E I G C I E |
| | |
| F12 (SEQ ID NO: 42) | (K) E S S I C X D F G N E F C R N A E C E V V P (K) |
| aa 19–42 | A  E S S I C S D F G N E F C R N A E C E V V P  G |
| | |
| F13 (SEQ ID NO: 15) | (K) T R E C S Y G R C V E S N P S K |
| aa 72–88 | K  T R E C S Y G R C V E S N P S K |
| | |
| F14 (SEQ ID NO: 16) | (K) A Y E C T C T C P R A F T V A E D G I S/H C K |
| aa 227–247 | K  A Y E C T C T C P S  G S T V A E D G I T  C K |
| | |
| F15 a (SEQ ID NO: 33) | (K) N L L Q R D S — C C Q |
| aa 165–176 | K  N L L Q R D S R  C C Q |
| | |
| F16 (SEQ ID NO: 47) | K X X V L C E X P |
| aa 273–281 | K G T V L C E C P |

From the DNA sequence and the amino acid sequence deduced from that DNA sequence, it can be seen that the pre-pro-polypeptide of the WGL$^+$ antigen consists of 650 amino acids (SEQ ID NO:56).

The DNA sequence coding for peptide F12 (SEQ ID NO:42) can be identified at the region 90–152 bp (FIGS. 6–6(2) (SEQ ID NO:55)) of the DNA sequence and corresponds to amino acids 20–40 in the amino acid sequence (FIG. 8, residues 30–50 of SEQ ID NO:57) of the protein. The amino acid preceding the N-terminal glu residue identified in F12 is not a lysine (K) as would be expected if F12 was generated as a result of digestion by endo lys-C. Therefore it is assumed that the F12 peptide fragment was generated by the action of a proteinase other than endo lys-C. The 19 amino acid sequence preceding the F12 N-terminal glu residue begins with a methionine and has hydrophobicity properties which are very similar to leader sequences which precede other secreted and membrane-bound proteins in eukaryote cells (see 9 for review). In addition, the majority of peptide leader sequences are cleaved at positions following A residues (9). It appears therefore that the F12 sequence is the N-terminus of the mature WGL$^+$ polypeptide. This then indicates that the protein portion of the mature WGL⁺ polypeptide is 631 amino acids long and which would have a molecular weight of 69 729 daltons.

Assuming that the consensus sequence for N-linked glycosylation is Asn X (Ser or Thr) in ticks as has been reported to be the case in other eukaryotic cells (10) 5 potential sites for N-linked glycosylation can be identified in the mature polypeptide sequence (FIGS. 6–6(2). Carbohydrate residues added to these residues or to other amino acids in the WGL⁺ antigen produced by ticks would account for the differences in the observed molecular weight for the native antigen compared with that predicted from the DNA sequence.

By comparison of the amino acid sequence (Table 9) with the peptide sequences derived from the fractions from endo lys-C digestion, all of the peptides (F1–17) with the exception of F7 can be identified. In most cases, the amino acids which could not be confidently ascribed during the peptide sequence analysis can be shown to be correct following comparison with the sequence deduced from the DNA sequence.

The amino acid sequence for peptide fragments F1, F11, F13 and F17 (SEQ ID NOS:1,173,15 and 21, respectively) all match precisely with the amino acid sequences deduced from the DNA sequence from the corresponding region of DNA (Table 9).

Peptide F2 (SEQ ID NO:2) can be seen to be coded for by the DNA segment 1104–1152 bp. Table 9 shows that the G and the X tentatively ascribed to positions 5 and 11 in the F2 peptide sequence are both N. N is very difficult to detect during gas phase sequencing and there was very little material in the sample. Otherwise the match is precise. F2 is the same peptide as F11 and all amino acids were ascribed correctly during the sequence analysis of the F11 peptide fragment.

Peptides F3 (SEQ ID NO:3) and F17 show sequences of the same peptide obtained from two different endo lys-C digests of WGL⁺ (Examples 3 and 4). The amino acid sequence for F17 matches precisely with the translated sequence from amino acids 405 to 412 of the WGL⁺ peptide. When sequencing F3, no amino acid could be ascribed to the first position (L from the DNA sequence) as there was a large amount of background but the rest of the amino acids match precisely with the amino acid sequence derived from the DNA sequence (amino acids 405–421 FIG. 8, residues 415–431 of SEQ ID NO:57).

F4 (SEQ ID NO:4) is found at amino acids 213–219 of the WGL⁺ protein (FIG. 8, residues 223–229 of SEQ ID NO:57). The sequence matches perfectly and the uncertain $^C/Q$ is shown from the DNA sequence to be C. Carboxymethylated C migrates with a similar retention time to Q in the HPLC system used to separate the derivatized amino acids following the sequencing reactions.

Very small amounts of material were sequencable in fragment F5 (SEQ ID NO:5) so there were several uncertainties. But it is clear that the sequence obtained corresponds to amino acids 200–210 in FIG. 8 (residues 210–220 of SEQ ID NO:57). One of the two amino acids tentatively ascribed to each peptide is present in the amino acid sequence derived from the DNA sequence and those ascribed with confidence appear in the expected order.

F6 (SEQ ID NO:6) sequence corresponds to amino acids 488–503 in the WGL⁺ protein sequence. The residues in the sequence derived for the F6 fragment differ from that derived from the DNA sequence. The F6 sequence presented was derived from a mixed sequence in which the amino acids shown to be correct from the DNA sequence were in fact present.

F7 (SEQ ID NO:7) has not been identified with confidence in the amino acid sequence derived from the DNA sequence. As with F6, the F7 sequence was derived from a mixed sequence and very little confidence can be placed in it.

Small amounts of material were present in F8 (SEQ ID NO:8) sample so there were several uncertainties in the sequence. However, the F8 amino acid sequence appears to correspond to amino acids 444–450 in FIG. 8 (residues 454–469 of SEQ ID NO:57). Again all uncertain residues can be identified in the translated DNA sequence.

F9 (SEQ ID NOS:27 and 46) and F10 (SEQ ID NOS:27 and 29) were both mixtures of two amino acid sequences. It is apparent that one of those sequences corresponds to amino acids 51–63 in FIG. 8 (residues 61–72 of SEQ ID NO:57). In both cases, one of the two amino acids identified during the peptide sequence analysis can be ascribed to the amino acid sequence derived from the DNA sequence in the expected order.

The remaining peptide sequence from F9 and F10 corresponds to amino acids 514–531 in FIG. 8 (residues 524–541 of SEQ ID NO:57). The R recorded for position 11 in the F9 sequence is P from the DNA sequence which is in agreement with the sequence obtained for F10. The DNA sequence shows K at what would be position 10 of this peptide. The DNA sequence shown is that coding for one molecule of the WGL⁺ antigen and it is likely that different ticks have some variants of the sequence. This point will be expanded when discussing the F14 sequence.

The fragment sequenced as F12 (SEQ ID NO:42) clearly corresponds to amino acids 20–41 in FIG. 8 (residues 30–51 of SEQ ID NO:57) and, as discussed previously is assumed to be the N-terminal fragment of the mature WGL⁺ peptide so the presumption that lysine preceded the first amino acids sequenced was incorrect in this case. The uncertain residue at position 6 of the peptide fragment is S from the DNA sequence. S is very difficult to detect during gas phase sequencing particularly as in this case, when the preceding amino acid is C and carboxy-methylated-C has a similar retention time to S in the HPLC system used to resolve the derivatized amino acids. Otherwise the F12 peptide sequence matches the sequence derived for WGL⁺ exactly.

F14 (SEQ ID NO:16) is very interesting (amino acids 228–247). The peptide sequence showed RAF for amino acids 8–10 in the peptide, whereas the DNA sequence, when translated, shows SGS in these positions. Both sequences appear to be correct retrospectively so there is a clear discrepancy between the two sequences. The most likely explanation is that both sequences are correct for the molecule (in the case of the cDNA) and the mixture of molecules (in the case of F12) which have been sequenced.

The tick population world wide is genetically diverse as is the case for all organisms which reproduce sexually. Each individual of a population differs subtly from the others in the population and these differences are a consequence of differences in the sequence of the DNA which each individual inherits from its parents. Thus for each gene coding for a particular protein, there are likely to be differences in the sequence among the population of individuals, referred to herein as homologues. In the particular example discussed here, the WGL⁺ protein which was digested in Example 4 to give rise to F12 was extracted from a large number of ticks (60,000–70,000). The peptide sequence determined for F12 (SEQ ID NO:42) (and the rest of the peptide fragments sequenced) is that of the majority of the population of WGL⁺ molecules. Among that population of WGL⁺ molecules, it is likely that minor variance (homologues) will exist at a level too low to be detected during the peptide sequence analysis. The cDNA sequence shown in FIG. 7 (bases 1–2012 of SEQ ID NO:55 and SEQ ID NO:56) and the amino acid sequence in FIG. 8 are derived from one cDNA molecule from one individual in the population. This individual may have contained a DNA sequence coding for a minor variant of the WGL$^+$ molecule. It is of course understood that other cDNA molecules may be derived from other individuals of the tick population world wide which will similarly vary in some small way from the sequence shown in FIGS. 6–6(2) but still code for a protein which is essentially the same as that for the WGL$^+$ antigen molecule. These homologues are included within the scope of this invention.

If the differences such as the one above are found in regions of the WGL$^+$ molecule which are important epitopes for the protective immune response generated against the WGL$^+$ molecule following vaccination, it is possible that the ticks with a WGL$^+$ product which is a homologues of the sequence shown in FIG. 6–6(2) may survive feeding on vaccinated hosts. In this instance it is to be understood that cDNA can be synthesised or DNA isolated from these individuals as described above or by other methods known in the art. In hybridization experiments the 4 kb DNA fragment (or parts thereof) can be used as hybridization probes to identify clones containing DNA coding for the WGL$^+$ protein from those variants which can then be used to construct bacteria or other micro-organisms which synthesize the variant WGL$^+$ antigen to be incorporated into effective vaccine against the variant tick population. This principal extends to isolates of *Boophilus microplus* and to other species of ticks from anywhere in the world.

The other difference in the sequence of F14 (SEQ ID NO:16) compared with the sequence for WGL$^+$ polypeptide derived from the DNA sequence is that the residue at position 18 (S or H in F12 which was ascribed with low confidence) is T from the DNA sequence.

F15 (SEQ ID NOS:17–19) was a mixture of at least three oligopeptides. Among those, one seems to be represented in the polypeptide at amino acids 166–176.

The F16 (SEQ ID NO:20) sequence can be seen in the WGL$^+$ amino acid segment 274–281 (FIG. 8, residues 284–291 of SEQ ID NO:57). The two uncertain residues in the peptide sequences are X=T in the second position and X=C in the seventh position of F16, both of which were due to the very small amounts of material which were present in this peptide sample.

In summary, it is clear that the DNA sequence shown in Table 9 codes for one homologue of the tick WGL$^+$ polypeptide as 16 of the 17 endo lys-C peptide fragments shown which were generated from the antigen isolated from ticks can be coded for by that DNA sequence. Evidence has been obtained that homologues of that gene may exist in the tick population and these are included within the scope of this invention whether the homologues originate from *Boophilus microplus* or other species of ticks found world wide.

The procedures outlined above refer to the WGL$^+$ antigen derived from *Boophilus microplus*. It is clear that this antigen or the equivalent antigen isolated from other tick species may well be effective against other species of Boophilus such as *B. annulatus*, other tick species such as Haemaphysalis spp, Otobius spp, Rhiphicephalus spp, Ambylomma spp. Dermacentor spp, Ixodes spp and Hyalomma spp, and particular species thereof including *Otobius megnini, Rhiphicephalus appendiculatus, Amblyomma variegatum, Haemaphysalis longicornis, Dermacentor andersoni, D. variabilis* and *Ixodes holocyclus* each of which causes significant economic loss throughout the world either as a result of infestation or as vectors of diseases such as *Babesia bovis, Babesia bigemina, Anaplasma marginale, Cowdria ruminatum, Theileria parva parva, T. parva lawrencii, T. annulata* and *T. hirci*. The WGL$^+$ gene product or the equivalent gene product from the related and other acarines would be expected to provide effective vaccines against the parasites as an extension of the work presented herein.

Comments on Hybridization Probes Used

The oligonucleotide probes which were chosen had several shortcomings which can be identified retrospectively. Some of these were due to incorrect choice of bases in the third codon positions and, of course to the uncertainties in the peptide sequence analysis. The oligonucleotide which was relied upon most heavily was the 63-mer as it was based on the most reliable amino acid sequence obtained at that time. When isolating the clones it was surprising that the hybridization signal with this probe was weaker than expected from theoretical considerations and at one stage there was doubt that the clone isolated coded for the WGL$^+$ peptide. This uncertainty was alleviated to some extent by the use of the degenerate oligonucleotide sequences mentioned above as probes. These probes hybridized strongly to the DNA in the clone. The reason for the weaker than expected signal with the 63-mer can now be explained by the variation in the DNA sequence from that expected in this region. A large number of other clones were purified based on the hybridization signal obtained with one or two probes but these all turned out to be unrelated to the WGL$^+$ gene by DNA sequence analysis. Therefore the strategy for isolating the clone by using triplicate filters and the use of the highly degenerate oligonucleotide sequences as hybridization probes to confirm the interest in the clone has been vindicated.

EXAMPLE 8

Construction of Recombinant Organisms Synthesizing WGL$^+$ Antigen

The major limitation to the development of a commercial vaccine based on the WGL$^+$ antigen or homologues thereof is the limited amount of the antigen which can be obtained from ticks. The means by which this shortage can be overcome include the use of recombinant DNA techniques to engineer bacteria or eukaryote cells to synthesize large amounts of the antigen. The following by means of example only outline some approaches which could be taken.

Figure 8A:
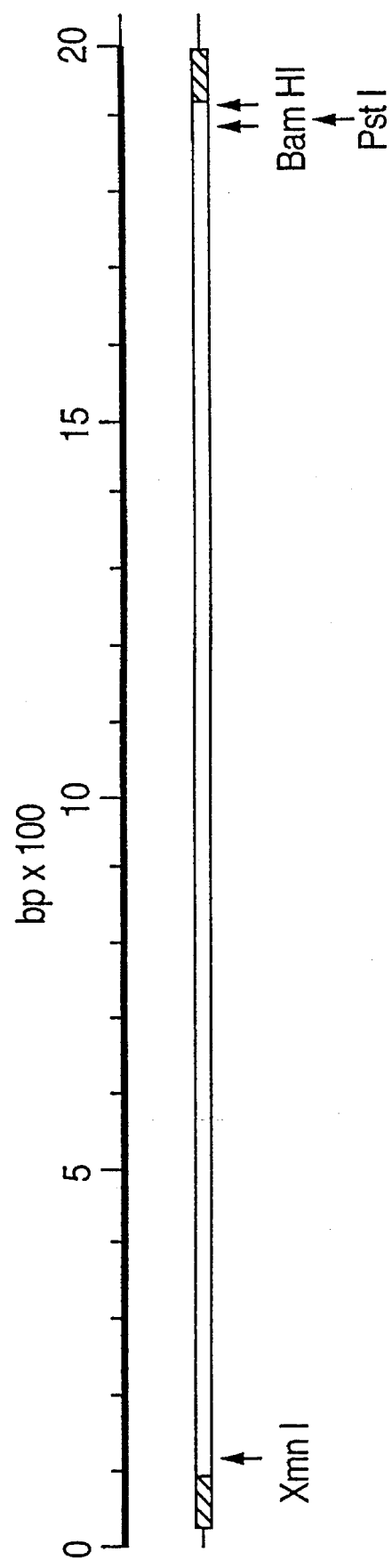

FIGS. 8A–8B show a restriction enzyme map of the gene coding for the WGL$^+$ antigen isolated from *B. microplus*. In order to engineer bacteria which express the gene product at high levels, it would probably be desirable to remove the parts of the molecule which are hydrophobic. These include the hydrophobic leader sequence (amino acids 1–19) which is not found in the mature polypeptide, and the hydrophobic C-terminal sequence (amino acids 630–650) which is likely to be an anchor sequence involved in attaching the antigen to the outer surface of the tick cells. In FIGS. 8A–8B, cleavage sites for the restriction enzymes XmnI (116 bases), PstI (1915 bases) and BamHI (1889 bases) are highlighted. DNA fragments produced by digestion of the WGL$^+$ gene with XmnI in addition to BamHI or PstI will contain the coding region for the majority of the gene without the N-terminal hydrophobic sequence or the C-terminal hydrophobic sequences. These 1773 bp and 1799 bp fragments can be subcloned into a number of plasmids including plasmids pBTA603 and pBTA224 to yield recombinant plasmids which will direct the synthesis of fused proteins containing the majority of the WGL+ peptide.

Biotechnologies, Inc.). By cutting the new construct with SacI and PstI, a fragment encoding most of the WGL+ and having SacI and PstI cohesive ends could be obtained. The sequences for the SacI end are also shown in SEQ ID NOS:51 and 52.

```
                   121 of WGL+ sequence        1911
 SacI    5'              >              >         PstI
 end     CGGT ACCC AG TTC TGT           AGT GCT GCA end
         TCGAGCCATGGG TC AAG ACA        TCA CG
 3'  From M13um31             From WGL+ gene
```

This fragment ligated to the large pBTA224 SacI PstI fragment described above gives (SEQ ID NOS: 53 and 54).

```
                                             WGL+
 2/3rds lacZ gene AAC GAG CT    CGGT ACCCAG TCC ----
                  TTGC TC  GA   GCCATGGGTC AAG ----
```

Plasmid pBTA603 has the PL promoter followed by a sequence from the N-terminus for the MS2 polymerase gene containing a multiple clone site vis

ATG TCG AAG ACA ACA AAG AAG TTC AAC TCT TTA TCG ATG/GAT CCC

Restriction endonuclease BamHI cuts the DNA where indicated (/) to give a 4 base 5' single stranded overhang. When this is filled in with DNA polymerase 1, the sequence (bases 34-43 of SEQ ID NO:48) MS2 —TCG ATG GAT C is generated. When this is ligated to XmnI cut WGL+ DNA (XmnI cuts at the sequence (SEQ ID NO:49) GAANNNNTTC i.e. following base 120) the sequence (SEQ ID NO:50) MS2—TCG ATG GAT CAG TTC TGT— WGL+ is generated. The plasmid so constructed encodes a protein which contains 15N terminal amino acids from the MS2 polymerase and the cloning site sequences in place of the N-terminal 11 amino acids of the mature WGL+ sequence followed by the WGL+ amino acid sequence from amino acids 31 to 620 for the BamHI fragment or 31 to 628 for the PstI fragment. When transformed into a suitable host such as N4830(10) which contains a mutation (cI$^{ts}$) in the gene coding for the cI repressor, expression of the fused polypeptide is repressed at temperatures such as 30° C. but is active at temperatures such as 42° C. This temperature dependence of expression is advantageous in instances where the fused product is deleterious to the cells. Cells are grown at 30° C. to the desired cell density and the temperature is then increased to 42° C. to induce the synthesis of the fused protein.

The expression vector pBTA224 was used to generate a strain capable of producing a β-galactosidase-WGL+ fusion protein. pBTA224 was derived from pUR292 (EMBO J. 2, 1791–1794 (1983)) by eliminating the EcoR1 site that lies outside of the β-galactosidase-coding region. pBTA224 DNA was cut with the restriction endonucleases SacI and PstI, and the resulting 4221 bp fragment was purified by agarose gel electrophoresis. SacI cuts within the lac Z gene, 1181 bps from the 3' end. PstI cuts pBTA224 at the 3' end of lacZ. A WGL+ gene fragment suitable for expression in this vector was prepared by first inserting an XmnI restriction fragment of about 2 Kb (position 116 to past 3' end of WGL+ gene) into the vector M13um31 (obtained from International The fusion protein expected to be produced after induction with IPTG consists of the first 651 amino acids of β galactosidase, 599 amino acids of WGL+ and 19 amino acids that are encoded by other parts of the expression vector, such as the multiple cloning sites. The calculated molecular weight is 143,054 daltons.

The plasmid described above has been designated pBTA708. A suitable E. coli host containing the lacI$^q$ gene is JM101. BTA1752 is JM101 transformed with pBTA708.

Figures 9A, 9B:
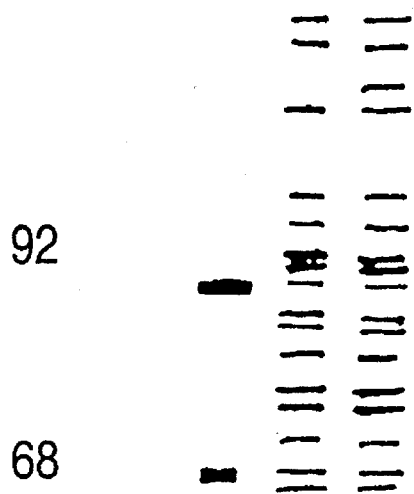
FIGS. 9A and 9B show a SDS polyacrylamide gel and immunoblot demonstrating expression of WGL+ by bacteria.

Cell lysates prepared from IPTG induced and control cultures, were analysed by electrophoresis in SDS-polyacrylamide gels. One gel was stained with Coomassie brilliant blue and a band of about the expected size could be visualised (FIGS. 9A–9B). The band was absent in the non-induced control. A duplicate SDS-polyacrylamide gel was also run and the proteins in the gel were transferred to nitrocellulose paper. The nitrocellulose paper was incubated in BLOTTO (a solution of 5% powdered milk in Tris-saline) for 2 hours, then in BLOTTO containing a 1/500 dilution of serum from a rabbit vaccinated with the fractions GF5 and 6 (see above) for 13 hrs at 4° C., then washed three times with BLOTTO, then incubated in a solution containing goat-anti-rabbit immunoglobulin conjugated to alkaline phosphatase (Promega Biotec). Following incubation for 1 hr, the nitrocellulose was removed, washed twice in BLOTTO and incubated in buffer containing Nitro blue tetrazolium and 5-bromo-4-chloro-3-indolyl phosphate. A band appeared where the rabbit antibodies had bound to the β galactosidase-WGL+ fused polypeptide synthesized by the bacteria (FIG. 10). The position of the band corresponds to the position of the band seen in the coomassie stained gel.

EXAMPLE 9

Fermentation Purification and Formulation of Vaccines Based on the WGL+ Antigen Produced by rDNA Techniques Strains expressing the WGL+ antigen or portions thereof are maintained as freeze-dried vials in the production culture collection. Cells from the storage vial are reconstituted and plated out on a selective medium, and the cells from this medium are used to prepare fermentor inocula. The inocula are used to seed fermentors containing a suitable growth medium and the fermentation proceeds under conditions appropriate for the production of the WGL+ proteins. At the completion of the fermentation the cells are harvested and the product is released from the cells and undergoes purification. The product is subjected to analyses and quality control, and is stored under conditions appropriate for good stability. The product is formulated for use by combination with other ingredients under conditions of strict hygiene.

The strains produce the WGL$^+$ fusion proteins in vivo as insoluble agglomerates termed inclusion bodies and can be produced and purified by the following procedure which is presented by means of example only.

Overnight cultures of BTA1752 is diluted 1:50 into 2×1 liter fresh LB (10 g tryptone/5 g yeast extract/5 g NaCl per liter pH 7.5) in 2 liter baffled flasks and shaken at 30° C. until the culture density reached OD 0.3–0.4. IPTG is added to a final concentration of 10 mM and incubation continued for a further 10 hours. The cells are harvested and resuspended in 20 ml of water per liter of original culture and broken by use of a French Press. The suspension is made 0.1 mM in phenylmethylsulfonyl fluoride (PMSF) and 5% Triton X-100 then centrifuged at 12,000× gav for 10 minutes. The supernatant is discarded and the pellet resuspended by ultrasound in 50 ml 1M NaCl/5% Triton X-100 and recentrifuged. This washing stage is repeated and the pellet finally resuspended using ultrasound in 2.5 ml 1M NaCl/5% Triton X-100 per liter original culture.

Purified inclusion bodies are dissolved at 2 mg/ml in 8M urea/0.1M DTT/0.1M Tris HCl pH 8.0 under nitrogen at 37° C. for 2 hrs. The solution is centrifuged at 20,000× gav for 20 min and the supernatant passed through a 0.1 µm filter. The flow through is passed through a filter with a molecular weight cut-off of 30 kilodaltons and the retained material is applied to a DEAE resin which is poured into a column and washed with 0.1M tris buffer pH 8. The column is then resolved with a linear gradient of from 0–5M NaCl in 8M urea 0.1M Tris pH 8.0 and the fractions analysed by SDS-Polyacrylamide gel electrophores. Those containing the desired protein are pooled, concentrated and desalted on a XM30 filter. The partially purified protein is emulsified in an adjuvant such as Marcol 52:Montanide 888 (9:1) or Freunds complete or incomplete adjuvant and administered to animals.

EXAMPLE 10

Identification of DNA Sequences Coding for the WGL$^+$ Antigen in Species of Tick Other than *Boophilus microplus*

In various countries throughout the world, tick species other than *Boophilus microplus* are responsible for extensive productivity losses either due to the tick infestation or due to the other parasites which the ticks transmit or a combination of both. It would be highly desirable to develop vaccines against these tick species. This may be achieved by vaccinating animals with the WGL$^+$ antigen derived from *Boophilus microplus* or the other immunogenic protective fractions described in this and Australian patent application No. 45936/85. It may also be possible to vaccinate animals with the WGL$^+$ antigen produced by recombinant organisms described herein and elicit an immune response which protects against infestation of animals by other species of tick.

As discussed above, the other species of tick probably contain a molecule which is functionally related to the *Boophilus microplus* WGL$^+$ antigen but which differs in sequence from that shown in FIG. 8. If those differences occur in areas eliciting protective immune responses, then the *Boophilus microplus* WGL$^+$ antigen may not be protective. However, the related gene product from the other species of tick is likely to be protective against those tick species, when incorporated into a vaccine.

One means by which this proposal can be tested is to conduct a series of vaccination/challenge experiments using fractions derived from homogenates of other ticks and purify the WGL$^+$ homologues from the other tick species. These can then be cleaved with proteinases, peptide fragments sequenced, oligonucleotides designed and used to identify recombinant organisms containing the genes in a similar way to that in which the *Boophilus microplus* WGL$^+$ gene has been identified in the present work.

A preferable approach is to construct cDNA or genomic DNA libraries from nucleic acids extracted from other tick species and to use the DNA fragment shown in FIGS. 6–6(2) (bases 1–2012 of SEQ ID NO:55) or portions thereof as hybridization probes to identify clones containing the homologous gene from the other tick species. Then, engineered recombinant microorganisms synthesizing the homologous gene product could be incorporated into an effective vaccine against the other species of ticks.

In order to demonstrate that this latter approach is feasible and to generate information concerning the conditions under which the hybridization to the clone libraries should be carried out, preliminary "Southern blot" hybridization experiments can be conducted. Briefly by way of example only DNA isolated from a number of species of tick is purified and digested with restriction endonucleases. The DNA fragments so produced are size fractionated by electrophoresis on agarose gels, denatured and transferred to nylon or nitrocellulose filters by capillary action. The filter is, incubated in a prehybridization solution and then in a hybridization solution containing radioactively labelled DNA fragments derived from the WGL$^+$ gene coding region. Following hybridization and washing of the filters, they are exposed to X-ray film and the resulting autoradiograph shows exposed areas which correspond to the DNA fragments from the various tick species which have hybridized to the WGL$^+$ DNA fragments. There are many variations of protocols for carrying out this procedure which will be known to individuals skilled in the art and the following is detailed by means of example only.

Eggs were obtained from female ticks of the species *Rhiphicepalus appendiculatus*, *Amblyomma variegatim*, *Boophilus decoloratus* and *Boophilus microplus*. They were incubated in a humidified incubator for 2–4 days then suspended in cold TE buffer and washed. They were then suspended in TE buffer containing 0.5% SDS in a loose fitting glass-homogeniser and gently homogenised to disrupt the eggs. Proteinase K was added to a final concentration of 50 µg/ml and the mixture was incubated at 37° C. for 1–2 h with gentle shaking. The viscous solution was gently extracted three times with phenol saturated with 0.1M Tris-HCl pH 8.0 and then twice with ether (centrifugation at 5,000× gav for 10 minutes was used to resolve the phases during the phenol extractions). Sodium acetate was added to 0.3M and 2 volumes of ethanol was slowly added with stirring. The DNA which came out of solution as a fibrous precipitate was removed with a pasteur pipette, washed in ethanol, and gently redissolved in TE.

Aliquots (generally containing 10 µg) of these DNA samples were digested with restriction endonucleases according to the manufacturers instructions. Aliquots of the digest products were fractionated by electrophoresis on a 1.6% agarose gel in SEB buffer (10). The DNA was depurinated with 2 volumes of 0.25M HCl for 15 minutes. The DNA was transferred by capillary action to a nylon membrane (Zetaprobe, Biorad). The filters were incubated in prehybridization in a solution (10) containing herring sperm DNA for 2–4 hours at 55° C. Hybridization was carried out in the same solution containing heat denatured [$^{32}$P] labelled DNA fragments from the WGL$^+$ gene (approximately $10^5$ counts per minute/ml) for 20 hours at 68° C. The filters were washed at 55° C. for 30 minutes each in 2× SSC, 0.1% SDS then three times at 60° C. for 15 minutes. After exposure to X-ray film for at least 24 hours the size of the hybridizing fragments could be determined by comparison with marker DNA fragments of known size.

Figure 10A:
FIGS. 10A–10C show hybridization of the *Boophilus microplus* DNA coding for WGL+ to DNA from other tick species.
Figure 10B:
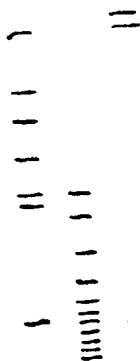
Figure 10C:
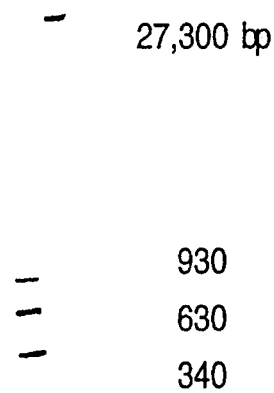

FIGS. 10A–10C show an autoradiogram of one such experiment. DNA was digested with restriction endonuclease Sau 3A. The WGL$^+$ DNA clearly hybridizes to the DNA from all four species of ticks. In this experiment, the DNA was not intact so a smear is observed in all cases but hybridization is specific as no hybridization to control DNA on the same gel could be detected.

EXAMPLE 11

Isolation of Clones Coding for WGL$^+$ Homologous from Other Tick Species

The DNA from each of the species tested possesses sequences which are similar to and homologous with the DNA coding for the WGL$^+$ antigen from *Boophilus microplus*. Clones containing those DNA sequences from other tick species can be isolated by constructing cDNA or genomic DNA libraries for the other tick species and hybridizing *Boophilus microplus* DNA fragments to those libraries, and purifying recombinant organisms containing the DNA sequences hybridizing to the homologous genes.

More specifically, the genomic DNA isolated from the tick species listed was subjected to partial digestion with the restriction enzyme Sau 3A to give fragments with an average size of 15–20 Kb as judged by gel analysis. These were ligated into the Bam HI site of lambda EMBL 3 arms essentially as described by the suppliers (Promega Biotech). The libraries were plated on a restrictive host K62 and incubated overnight at 37° C. The plaques were transferred to triplicate nitrocellulose filters, and the DNA denatured with 1.5M NaCl/0.5M NaOH, neutralised with 3M NaCl/ 0.5M Tris HCl pH 7.0. Then the filters were vacuum baked at 80° C. for 2 hours and hybridized to *Boophilus microplus* DNA probes labelled with $^{32}$P. Following autoradiography, plaques which hybridized to the probes on both filters were identified, picked and purified to single plaques by repeated rounds of re hybridization.

DNA was isolated from one plaque from a *B. decoloratus* genomic library and digested with restriction endonucleases HacIII and Apa 1. The fragments so produced were separated by electrophoresis on 1.6% agarose gels. One gel was stained with an ethidium bromide solution and the bands visualised under ultraviolet light (FIGS. 10A–10C). A replicate gel was transferred to nylon membrane and hybridized to *Boophilus microplus* DNA coding for the WGL$^+$ antigen. FIGS. 10A–10C show that fragments from the *Boophilus decoloratus, Amblyomma variegatum* genomic clone hybridize to the WGL$^+$ gene.

The bands hybridising in the HaeIII digest are approximately 980, 630, and 340 bp and in the Apa 1 digest 27,300 bp when compared with fragments of DNA from bacteriophage lambda digested with Hind III.

The regions of the DNA in each plaque which codes for portions of the homologous gene for the WGL$^+$ antigen from each species of tick are sequenced and engineered for expression in recombinant organisms essentially as described above for the *Boophilus microplus* WGL$^+$ antigen. The same approach can also be taken to isolate cDNA clones from these and other tick species.

The homologous WGL$^+$ antigen proteins expressed by the microorganisms are then grown in fermenters, the expression of the recombinant antigen induced and the antigen is purified formulated with an adjuvant or carrier and used to vaccinate animals.

It is understood that this procedure can be equally well applied to any species of tick to isolate clones coding for WGL$^+$ related antigens and the WGL$^+$ related proteins expressed by the so constructed genetically engineered microorganisms can be used as effective vaccines against a range of tick species which are responsible for productivity losses, morbidity and mortality to domestic animals and man.

EXAMPLE 12

RNA was extracted from ticks collected from different regions of the world and cDNA libraries were constructed using lambda vectors essentially as described in Example 6. Replicas of these cDNA libraries were hybridised with radioactively labelled restriction fragments derived from the DNA coding for the WGL+ antigen using hybridisation conditions designed to detect nucleic acid sequences having a minimum of 70% homology to the hybridising sequence. The resulting plaques that reacted with the DNA hybridisation probes were then purified to single plaques. The DNA sequences of the genes were determined using standard sequencing techniques. FIGS. 12–17 illustrate the DNA sequences and deduced amino acid sequences (SEQ ID NOS:58–69).

The DNA sequence YBm017 (FIG. 12 (SEQ ID NO:58)), was derived from an Australian isolate of *Boophilus microplus* (Yeerongpilly, Queensland). The WGL+ antigen described in the preceding examples was also obtained from the same isolate. A comparison of the DNA sequences reveals:

(i) The DNA sequences are not identical. There is approximately 95% homology at the DNA level but it is clear that the two sequences code for the same antigen.

(ii) The translated amino acid sequence (SEQ ID NO:59) has 8 differences between the two antigens. For example, the WGL+ sequence encodes a phenylalanine at position 1551 while YBm017 encodes a cysteine at the corresponding position (nucleotide 1570 in FIG. 12 (SEQ ID NO:58)). In addition, the sequence serine glycine serine (encoded by nucleotides 735 through 743 in the WGL+ sequence) is arginine alanine phenylalanine in the corresponding position of YBm017 (nucleotides 754 to 762 in FIG. 12 (SEQ ID NO:58)).

A partial cDNA clone encoding a protein fragment with an amino acid sequence homologous to that of WGL+ is presented as YBm22M8 (FIG. 13 (SEQ ID NO:60)). This sequence extends from nucleotide position 276 to nucleotide position 1922 of the WGL+ sequence. There are 13 differences between the deduced amino acid sequences of YBm22M8 (SEQ ID NO:61) and WGL+ (SEQ ID NO:56).

These observations further illustrate that the tick population, even within one isolate of ticks is genetically diverse and that homologues of the antigen are found within that population.

A second form of the antigen consisting essentially of the sequence described for YBm22M8 but including the amino terminus of the original WGL+ clone has been expressed in recombinant bacteria and used to vaccinate cattle which were subsequently challenged with ticks. This recombinant antigen protects cattle as well as that encoded by the WGL+ antigen.

The cDNA clone, Bm023 (FIG. 14 (SEQ ID NO:62)) was obtained from another Australian isolate of *Boophilus microplus*. The nucleotide sequence of this cDNA codes for a protein (SEQ ID NO:63) that has 13 amino acids that are different from those encoded by the WGL+ cDNA. This demonstrates that the major form of the WGL+ antigen is similar for the two populations of ticks.

The VBm021 and MexBm86 cDNA molecules (FIGS. 15 (SEQ ID NO:64) and 16 (SEQ ID NO:66) respectively) were obtained from *Boophilus microplus* isolates form Venezuela and Mexico respectively. The VBm021 sequence is a partial cDNA clone in that the sequence does not extend to the start codon of the gene. The sequence begins at a position corresponding to amino acid 31 of the deduced WGL+ amino acid sequence (nucleotide position 123 in FIG. 7 bases 1–2012 of SEQ ID NO:55). The MexBm86 cDNA sequence extends through the start codon and into the 5' untranslated region of the WGL+ sequence (FIG. 7 bases 1–2012 of SEQ ID NO:55). These sequences differ from the WGL+ deduced amino acid sequence by 28 (VBm021 SEQ ID NO:65) and 22 (MexBm86 SEQ ID NO:66) amino acids.

These results confirm that it is possible to isolate related genes from a diverse range of *Boophilus microplus* isolates using the WGL+ gene (or fragments derived from this gene) as hybridisation probes. The DNA sequences of the variants will enable the gene to be clearly identified as related to the WGL+ gene but the homology at the DNA sequence level may be no more than 50% over some regions. In addition the translated amino acid sequences of these genes clearly indicate that the genes code for proteins which are closely related to the WGL+ protein but may differ in amino acid sequence by as much as 30% over some stretches of the protein.

The Ra442 sequence (FIG. 17, SEQ ID NO:68) was obtained from *Rhipicephalus appendiculatus*. Comparison of this cDNA with WGL+ demonstrates that the Ra442 sequence codes for a protein fragment (SEQ ID NO:69) which is homologous to the WGL+ sequence corresponding to nucleotides 1113 to 1553 (FIG. 7 bases 1–2012 of SEQ ID NO:58). It contains structural elements which are characteristic of these molecules. The homology over this region is approximately 85% at the DNA level and approximately 70% at the amino acid level, with particular regions having higher homology than others. This is clearly a molecule which is closely related in structure (and presumably in function) to the WGL+ antigen from *Boophilus microplus*.

The nucleotide sequences presented in both YBm017 (SEQ ID NO:58) and VBm021 (SEQ ID NO:64) contain two nucleotides each that could not be determined unambiguously when reading the sequencing gels. These are represented using the IUPAC ambiguity code and result in the translated amino acid, Xaa. These were not included when describing the number of amino acid differences between these clones and the WGL+ sequence.

DEPOSITION OF MICROORGANISMS

Strain BTA 1751 referred to herein has been deposited with the American Type Culture Collection of 12301 Parklawn Drive Rockville, Md. 20852 USA in accordance with the provisions of the Budapest Treaty on 26 Oct. 1987 under accession number ATCC 67548.

Strain BTA 1751 has also been deposited with the China Centre for Type Culture Collection under import licence IL-87044 and designated CTCC.

INDUSTRIAL APPLICATION

The current invention provides a means of vaccinating cattle against infestation with ticks such as *Boophilus microplus, Boophilus annulatus*; other species such as Haemaphysalis spp, Otobius spp, Rhiphicephalus spp, Ambylomma spp, Dermacentor spp, Ixodes spp and Hyalomma spp; and particular examples thereof including *Otobius megnini, Rhiphicephalus appendiculatus, Dermacentor andersoni, D. variabilis* and *Ixodes holocyclus*. Further it provides a means of protecting cattle against diseases such as those caused by *Babesia bovis, Cowdria ruminatum, Theleria parva parva, T. parva lawrencil, T. annulata* and *T. hirci*. Further it provides diagnostic tools for the identification and quantification of tick antigens.

REFERENCES

1. Brown, S. J., Shapiro, S. Z. and Askenase, P. W. J. Immunol. 133, 1984, 3319–3325.

2. Ackerman, S., Floyd, M. and Sonenshine, D. E. J. Med. Entomol. 17, 1980, 391–397.

3. McGowan, M. J., Barker, M. J., Homer, J. T., McNew, R. W. and Holscher, K. M. 1971, J. Med. Entomol. 18, 1981, 328.

4. Wikel, S. K., Am. J. Trop. Med. Hyg. 30, 1981, 284.

5. Allen, J. R. and Humphries, S. J. Nature, 280, 1979, 481–493.

6. Johnson, L. A. Y., Kemp, D. H. and Pearson, R. D. Int. J. Parasitol. 16, 27–34, 1986.

7. Kemp, D. H., Agbede, R. I. S., Johnston, L. A. Y. and Gough, J. M. Int. J. Parasitol. 16, 121–130, 1986.

8. Agbede, R. I. S. and Kemp, D. H. Int. J. Parasitol. 16, 35–42, 1986.

9. Briggs M. S. and Gierasch, L. M. (1986), Molecular Mechanisms of Protein Secretion: The Role of the Signal Sequence, pages 110–180 in Advances in Protein Chemistry, vol. 38, Academic Press.

10. Maniatis, T., Fritsch, E. F. and Sambrook, J. (1982), Molecular cloning: A Laboratory Manual (Cold Spring Harbour Laboratory).

11. Kornfeld, R. and Kornfeld, S., 1985, Ann. Rev. Biochem 54, 631–664

12. Van Hemert, F. J., Amons, R., Pluijms, W. J. M., Van Ormondt, H. and Moeller, W. EMBO 3, 1109–1113 1984

13. Willadsen, P., Int. J. Parasitol, 17, 671–677 (1987)

14. Vretblad, P., Biochemica and Biophysica Acta, 434, 169–176 (1976).

15. Sage, H. J. and Green, R. W., in Methods in Enzymology, 28, Guinsburg, V., ed., 332–339 (1972), London Academic Press.

We claim:

1. An isolated and purified DNA molecule, free of homologous chromosomal DNA, comprising SEQ ID NO:55.

2. An isolated and purified polynucleotide sequence, free of homologous chromosomal DNA, encoding amino acids 1–650 of the polypeptide of SEQ ID NO:56.

3. An isolated and purified polynucleotide sequence free of homologous chromosomal DNA, which hybridizes to an isolated polynucleotide sequence encoding amino acids 1–650 of the polypeptide of SEQ ID NO:56 under conditions consisting of hybridization at 68° C. for 20 hours, followed by washing, wherein said washing comprises washing in 2X SSC, 0.1% SDS, twice for 30 minutes at 55° C. and three times for 15 minutes at 60° C.

4. An isolated polynucleotide sequence according to claim 3, wherein said polynucleotide sequence encodes a polypeptide that produces an immune response against tick infestation in a mammalian host when said polypeptide is administered to said mammalian host.

5. An isolated polynucleotide free of homologous chromosomal DNA, encoding a fragment of a polypeptide having the sequence of amino acids 1–650 of (SEQ ID NO:56), wherein said fragment is at least 193 amino acids in length.

6. An isolated polynucleotide according to claim 5, wherein said fragment encodes a polypeptide selected from the group consisting of amino acids 31 to 629, amino acids 31 to 406, amino acids 31 to 223, or amino acids 351 to 576 of the polypeptide having the sequence (SEQ ID NO:56).

7. A recombinant cloning vector comprising the DNA sequence according to claim 1.

8. A vector according to claim 7 wherein said vector further comprises phage, viral or plasmid DNA.

9. A vector according to claim 8 wherein said phage, viral, or plasmid DNA comprises lambda gt11, pUR290, pUR291, pUR282, pUK270, pUC8, pUC9, baculovirus, pZipNeo, an SV40 based vector, λgt10, an EMBL vector, pB327, pB329 or pBR329 containing a par locus.

10. Plasmid pBTA 707.

11. A vector according to claim 7 additionally comprising an expression control sequence operatively linked to said DNA sequence.

12. A vector according to claim 11 wherein said expression control sequence comprises a promoter and a translation start signal.

13. A transformed cell comprising a vector according to claim 7.

14. A transformed cell according to claim 13 wherein said cell is a bacterial, yeast, mammalian or insect cell.

15. A transformed cell according to claim 14 wherein said cell is Y 1090, Y 1089, or JM 101.

16. A transformed host cell accorded accession number ATCC 67548.

* * * * *

SEQUENCE LISTING ( 1 ) GENERAL INFORMATION:

( i i i ) NUMBER OF SEQUENCES: 71

( 2 ) INFORMATION FOR SEQ ID NO:1:

( i ) SEQUENCE CHARACTERISTICS:
        ( A ) LENGTH: 7 amino acids
        ( B ) TYPE: amino acid
        ( D ) TOPOLOGY: linear ( v i i ) IMMEDIATE SOURCE:
        ( B ) CLONE: F1

( x i ) SEQUENCE DESCRIPTION: SEQ ID NO:1:

Lys Asp Pro Asp Pro Gly Lys
    1                5

( 2 ) INFORMATION FOR SEQ ID NO:2:

( i ) SEQUENCE CHARACTERISTICS:
        ( A ) LENGTH: 17 amino acids
        ( B ) TYPE: amino acid
        ( D ) TOPOLOGY: linear ( v i i ) IMMEDIATE SOURCE:
        ( B ) CLONE: F2

( x i ) SEQUENCE DESCRIPTION: SEQ ID NO:2:

Lys Trp Tyr Glu Asp Gly Val Leu Glu Ala Ile Xaa Thr Ser Ile Gly
    1                5                          10                      15

Lys ( 2 ) INFORMATION FOR SEQ ID NO:3:

( i ) SEQUENCE CHARACTERISTICS:
        ( A ) LENGTH: 18 amino acids
        ( B ) TYPE: amino acid
        ( D ) TOPOLOGY: linear ( v i i ) IMMEDIATE SOURCE:
        ( B ) CLONE: F3

( x i ) SEQUENCE DESCRIPTION: SEQ ID NO:3:

Lys Xaa Gln Ala Cys Glu His Pro Ile Gly Glu Trp Cys Met Met Tyr
    1                5                          10                      15

Pro Lys ( 2 ) INFORMATION FOR SEQ ID NO:4:

( i ) SEQUENCE CHARACTERISTICS:
        ( A ) LENGTH: 8 amino acids
        ( B ) TYPE: amino acid
        ( D ) TOPOLOGY: linear ( v i i ) IMMEDIATE SOURCE:
        ( B ) CLONE: F4

( i x ) FEATURE:
        ( A ) NAME/KEY: Modified-site
        ( B ) LOCATION: 7
        ( D ) OTHER INFORMATION: /note= "Xaa at position 7
            represents Cys or Gln"

( x i ) SEQUENCE DESCRIPTION: SEQ ID NO:4:

Lys Glu Ala Gly Phe Val Xaa Lys
    1                5

( 2 ) INFORMATION FOR SEQ ID NO:5:

( i ) SEQUENCE CHARACTERISTICS:
      ( A ) LENGTH: 12 amino acids
      ( B ) TYPE: amino acid
      ( D ) TOPOLOGY: linear ( v i i ) IMMEDIATE SOURCE:
      ( B ) CLONE: F5

( i x ) FEATURE:
      ( A ) NAME/KEY: Modified-site
      ( B ) LOCATION: 4
      ( D ) OTHER INFORMATION: /note= "Xaa at position 4
          represents Ser or Asp"

( i x ) FEATURE:
      ( A ) NAME/KEY: Modified-site
      ( B ) LOCATION: 7
      ( D ) OTHER INFORMATION: /note= "Xaa at position 7
          represents Val or Cys"

( i x ) FEATURE:
      ( A ) NAME/KEY: Modified-site
      ( B ) LOCATION: 10
      ( D ) OTHER INFORMATION: /note= "Xaa at position 10
          represents Val or Ala"

( i x ) FEATURE:
      ( A ) NAME/KEY: Modified-site
      ( B ) LOCATION: 11
      ( D ) OTHER INFORMATION: /note= "Xaa at position 11
          represents Ile or Cys"

( x i ) SEQUENCE DESCRIPTION: SEQ ID NO:5:

Lys  Gly  Pro  Xaa  Gly  Gln  Xaa  Ile  Asn  Xaa  Xaa  Lys
   1                   5                        10

( 2 ) INFORMATION FOR SEQ ID NO:6:

( i ) SEQUENCE CHARACTERISTICS:
      ( A ) LENGTH: 17 amino acids
      ( B ) TYPE: amino acid
      ( D ) TOPOLOGY: linear ( v i i ) IMMEDIATE SOURCE:
      ( B ) CLONE: F6

( i x ) FEATURE:
      ( A ) NAME/KEY: Modified-site
      ( B ) LOCATION: 3
      ( D ) OTHER INFORMATION: /note= "Xaa at position 3
          represents Gly or Asp"

( x i ) SEQUENCE DESCRIPTION: SEQ ID NO:6:

Lys  Ala  Xaa  Val  Ser  Thr  Asn  Glu  Asn  Glu  Gln  Leu  Glu  Gln  Ala  Asp
   1                   5                        10                       15

Lys ( 2 ) INFORMATION FOR SEQ ID NO:7:

( i ) SEQUENCE CHARACTERISTICS:
      ( A ) LENGTH: 12 amino acids
      ( B ) TYPE: amino acid
      ( D ) TOPOLOGY: linear ( v i i ) IMMEDIATE SOURCE:
      ( B ) CLONE: F7

( i x ) FEATURE:
      ( A ) NAME/KEY: Modified-site
      ( B ) LOCATION: 3
      ( D ) OTHER INFORMATION: /note= "Xaa at position 3 represents Gly or Asp"

( x i ) SEQUENCE DESCRIPTION: SEQ ID NO:7:

```
Lys  Ser  Xaa  Thr  Gln  Xaa  Ile  Asp  His  Ile  Ser  Lys
1                  5                       10
```

( 2 ) INFORMATION FOR SEQ ID NO:8:

( i ) SEQUENCE CHARACTERISTICS:
        ( A ) LENGTH: 7 amino acids
        ( B ) TYPE: amino acid
        ( D ) TOPOLOGY: linear ( v i i ) IMMEDIATE SOURCE:
        ( B ) CLONE: F8

( i x ) FEATURE:
        ( A ) NAME/KEY: Modified-site
        ( B ) LOCATION: 2
        ( D ) OTHER INFORMATION: /note= "Xaa at position 2
        represents Asn or Asp"

( i x ) FEATURE:
        ( A ) NAME/KEY: Modified-site
        ( B ) LOCATION: 5
        ( D ) OTHER INFORMATION: /note= "Xaa at position 5
        represents Ala or Tyr"

( i x ) FEATURE:
        ( A ) NAME/KEY: Modified-site
        ( B ) LOCATION: 6
        ( D ) OTHER INFORMATION: /note= "Xaa at position 6
        represents Ala or Tyr"

( x i ) SEQUENCE DESCRIPTION: SEQ ID NO:8:

```
Lys  Xaa  Gln  Glu  Xaa  Xaa  Tyr
1                  5
```

( 2 ) INFORMATION FOR SEQ ID NO:9:

( i ) SEQUENCE CHARACTERISTICS:
        ( A ) LENGTH: 19 amino acids
        ( B ) TYPE: amino acid
        ( D ) TOPOLOGY: linear ( v i i ) IMMEDIATE SOURCE:
        ( B ) CLONE: F9

( x i ) SEQUENCE DESCRIPTION: SEQ ID NO:9:

```
Lys  Cys  Pro  Cys  Asp  Asn  Met  Tyr  Phe  Asn  Ala  Ala  Glu  Glu  Ile  Gly
1                  5                       10                      15
Cys  Ile  Glu
```

( 2 ) INFORMATION FOR SEQ ID NO:10:

( i ) SEQUENCE CHARACTERISTICS:
        ( A ) LENGTH: 17 amino acids
        ( B ) TYPE: amino acid
        ( D ) TOPOLOGY: linear ( v i i ) IMMEDIATE SOURCE:
        ( B ) CLONE: F9

( x i ) SEQUENCE DESCRIPTION: SEQ ID NO:10:

```
Ala  Asn  Gln  Cys  Pro  Pro  Asp  Thr  Arg  Arg  Gly  Glu  Ile  Gly  Cys  Ile
1                  5                       10                      15
Glu
```

( 2 ) INFORMATION FOR SEQ ID NO:11:

( i ) SEQUENCE CHARACTERISTICS:
  ( A ) LENGTH: 19 amino acids
  ( B ) TYPE: amino acid
  ( D ) TOPOLOGY: linear ( v i i ) IMMEDIATE SOURCE:
  ( B ) CLONE: F10

( x i ) SEQUENCE DESCRIPTION: SEQ ID NO:11:

Lys Ala Pro Arg Gln Asn Met Tyr Phe Asn Ala Ala Glu Glu Ile Gly
1               5                   10                  15

Cys Ile Glu ( 2 ) INFORMATION FOR SEQ ID NO:12:

( i ) SEQUENCE CHARACTERISTICS:
  ( A ) LENGTH: 18 amino acids
  ( B ) TYPE: amino acid
  ( D ) TOPOLOGY: linear ( v i i ) IMMEDIATE SOURCE:
  ( B ) CLONE: F10

( x i ) SEQUENCE DESCRIPTION: SEQ ID NO:12:

Cys Asn Cys Asp Cys Pro Pro Asp Thr Arg Pro Gly Glu Ile Gly Cys
1               5                   10                  15

Ile Glu ( 2 ) INFORMATION FOR SEQ ID NO:13:

( i ) SEQUENCE CHARACTERISTICS:
  ( A ) LENGTH: 17 amino acids
  ( B ) TYPE: amino acid
  ( D ) TOPOLOGY: linear ( v i i ) IMMEDIATE SOURCE:
  ( B ) CLONE: F11

( x i ) SEQUENCE DESCRIPTION: SEQ ID NO:13:

Lys Trp Tyr Glu Asp Arg Val Leu Glu Ala Ile Arg Thr Ser Ile Gly
1               5                   10                  15

Lys ( 2 ) INFORMATION FOR SEQ ID NO:14:

( i ) SEQUENCE CHARACTERISTICS:
  ( A ) LENGTH: 23 amino acids
  ( B ) TYPE: amino acid
  ( D ) TOPOLOGY: linear ( v i i ) IMMEDIATE SOURCE:
  ( B ) CLONE: F12

( x i ) SEQUENCE DESCRIPTION: SEQ ID NO:14:

Lys Glu Ser Ser Ile Cys Xaa Asp Phe Gly Asn Glu Phe Cys Arg Asn
1               5                   10                  15

Ala Glu Cys Glu Val Val Pro
                20

( 2 ) INFORMATION FOR SEQ ID NO:15:

( i ) SEQUENCE CHARACTERISTICS:
  ( A ) LENGTH: 17 amino acids
  ( B ) TYPE: amino acid
  ( D ) TOPOLOGY: linear ( v i i ) IMMEDIATE SOURCE:
  ( B ) CLONE: F13

( x i ) SEQUENCE DESCRIPTION: SEQ ID NO:15:

Lys Thr Arg Glu Cys Ser Tyr Gly Arg Cys Val Glu Ser Asn Pro Ser
1               5                   10                  15

Lys ( 2 ) INFORMATION FOR SEQ ID NO:16:

( i ) SEQUENCE CHARACTERISTICS:
         ( A ) LENGTH: 21 amino acids
         ( B ) TYPE: amino acid
         ( D ) TOPOLOGY: linear ( v i i ) IMMEDIATE SOURCE:
         ( B ) CLONE: F14

( i x ) FEATURE:
         ( A ) NAME/KEY: Modified-site
         ( B ) LOCATION: 19
         ( D ) OTHER INFORMATION: /note= "Xaa at position 19
               represents Ser or His"

( x i ) SEQUENCE DESCRIPTION: SEQ ID NO:16:

Lys Ala Tyr Glu Cys Thr Cys Pro Arg Ala Phe Thr Val Ala Glu Asp
1               5                   10                  15

Gly Ile Xaa Cys Lys
            20

( 2 ) INFORMATION FOR SEQ ID NO:17:

( i ) SEQUENCE CHARACTERISTICS:
         ( A ) LENGTH: 14 amino acids
         ( B ) TYPE: amino acid
         ( D ) TOPOLOGY: linear ( v i i ) IMMEDIATE SOURCE:
         ( B ) CLONE: F15

( i x ) FEATURE:
         ( A ) NAME/KEY: Modified-site
         ( B ) LOCATION: 8
         ( D ) OTHER INFORMATION: /note= "Xaa at position 8
               represents Ser or His"

( x i ) SEQUENCE DESCRIPTION: SEQ ID NO:17:

Lys Asp Glu Val Asp Asn Ala Xaa Leu Val Cys Gln Asn Ala
1               5                   10

( 2 ) INFORMATION FOR SEQ ID NO:18:

( i ) SEQUENCE CHARACTERISTICS:
         ( A ) LENGTH: 12 amino acids
         ( B ) TYPE: amino acid
         ( D ) TOPOLOGY: linear ( v i i ) IMMEDIATE SOURCE:
         ( B ) CLONE: F15

( x i ) SEQUENCE DESCRIPTION: SEQ ID NO:18:

Lys Asn Val Leu Gln Ser Asp Gly Cys Gly Pro Tyr
1               5                   10

( 2 ) INFORMATION FOR SEQ ID NO:19:

( i ) SEQUENCE CHARACTERISTICS:
         ( A ) LENGTH: 11 amino acids
         ( B ) TYPE: amino acid
         ( D ) TOPOLOGY: linear ( v i i ) IMMEDIATE SOURCE:

( B ) CLONE: F15

( i x ) FEATURE:
( A ) NAME/KEY: Modified-site
( B ) LOCATION: 7
( D ) OTHER INFORMATION: /note= "Xaa at position 7
represents Pro or Leu"

( i x ) FEATURE:
( A ) NAME/KEY: Modified-site
( B ) LOCATION: 11
( D ) OTHER INFORMATION: /note= "Xaa at position 11
represents His or Ser"

( x i ) SEQUENCE DESCRIPTION: SEQ ID NO:19:

```
Lys Cys Leu Asn Pro Arg Xaa Arg Leu Lys Xaa
1               5                   10
```

( 2 ) INFORMATION FOR SEQ ID NO:20:

( i ) SEQUENCE CHARACTERISTICS:
( A ) LENGTH: 9 amino acids
( B ) TYPE: amino acid
( D ) TOPOLOGY: linear ( v i i ) IMMEDIATE SOURCE:
( B ) CLONE: F16

( i x ) FEATURE:
( A ) NAME/KEY: Modified-site
( B ) LOCATION: 2
( D ) OTHER INFORMATION: /note= "Xaa at position 2
represents Ser, Ala, Cys or Gly"

( x i ) SEQUENCE DESCRIPTION: SEQ ID NO:20:

```
Lys Xaa Xaa Val Leu Cys Glu Xaa Pro
1               5
```

( 2 ) INFORMATION FOR SEQ ID NO:21:

( i ) SEQUENCE CHARACTERISTICS:
( A ) LENGTH: 9 amino acids
( B ) TYPE: amino acid
( D ) TOPOLOGY: linear ( v i i ) IMMEDIATE SOURCE:
( B ) CLONE: F17

( x i ) SEQUENCE DESCRIPTION: SEQ ID NO:21:

```
Lys Leu Gln Ala Cys Glu His Pro Ile
1               5
```

( 2 ) INFORMATION FOR SEQ ID NO:22:

( i ) SEQUENCE CHARACTERISTICS:
( A ) LENGTH: 18 amino acids
( B ) TYPE: amino acid
( D ) TOPOLOGY: linear ( v i i ) IMMEDIATE SOURCE:
( B ) CLONE: F3, F17

( x i ) SEQUENCE DESCRIPTION: SEQ ID NO:22:

```
Lys Leu Gln Ala Cys Glu His Pro Ile Gly Glu Trp Cys Met Met Tyr
1               5                   10                  15
Pro Lys
```

( 2 ) INFORMATION FOR SEQ ID NO:23:

( i ) SEQUENCE CHARACTERISTICS:
( A ) LENGTH: 8 amino acids (B) TYPE: amino acid
(D) TOPOLOGY: linear (vii) IMMEDIATE SOURCE:
(B) CLONE: F4

(xi) SEQUENCE DESCRIPTION: SEQ ID NO:23:

Lys Glu Ala Gly Phe Val Cys Lys
1               5

(2) INFORMATION FOR SEQ ID NO:24:

(i) SEQUENCE CHARACTERISTICS:
(A) LENGTH: 12 amino acids
(B) TYPE: amino acid
(D) TOPOLOGY: linear (vii) IMMEDIATE SOURCE:
(B) CLONE: F5

(xi) SEQUENCE DESCRIPTION: SEQ ID NO:24:

Lys Gly Pro Asp Gly Gln Cys Ile Asn Ala Cys Lys
1               5                   10

(2) INFORMATION FOR SEQ ID NO:25:

(i) SEQUENCE CHARACTERISTICS:
(A) LENGTH: 17 amino acids
(B) TYPE: amino acid
(D) TOPOLOGY: linear (vii) IMMEDIATE SOURCE:
(B) CLONE: F6

(xi) SEQUENCE DESCRIPTION: SEQ ID NO:25:

Lys Ala Gly Val Ser Cys Asn Glu Asn Glu Gln Ser Glu Cys Ala Asp
1               5                   10                  15

Lys (2) INFORMATION FOR SEQ ID NO:26:

(i) SEQUENCE CHARACTERISTICS:
(A) LENGTH: 8 amino acids
(B) TYPE: amino acid
(D) TOPOLOGY: linear (vii) IMMEDIATE SOURCE:
(B) CLONE: F8

(xi) SEQUENCE DESCRIPTION: SEQ ID NO:26:

Lys Asp Gln Glu Ala Ala Tyr Lys
1               5

(2) INFORMATION FOR SEQ ID NO:27:

(i) SEQUENCE CHARACTERISTICS:
(A) LENGTH: 14 amino acids
(B) TYPE: amino acid
(D) TOPOLOGY: linear (xi) SEQUENCE DESCRIPTION: SEQ ID NO:27:

Lys Cys Pro Arg Asp Asn Met Tyr Phe Asn Ala Ala Glu Lys
1               5                   10

(2) INFORMATION FOR SEQ ID NO:28:

(i) SEQUENCE CHARACTERISTICS:
(A) LENGTH: 19 amino acids
(B) TYPE: amino acid ( D ) TOPOLOGY: linear ( v i i ) IMMEDIATE SOURCE:
  ( B ) CLONE: F9, F10

( x i ) SEQUENCE DESCRIPTION: SEQ ID NO:28:

```
Lys Ala Asn Cys Gln Cys Pro Pro Asp Thr Lys Pro Gly Glu Ile Gly
1               5                   10                  15
Cys Ile Glu
```

( 2 ) INFORMATION FOR SEQ ID NO:29:

( i ) SEQUENCE CHARACTERISTICS:
    ( A ) LENGTH: 19 amino acids
    ( B ) TYPE: amino acid
    ( D ) TOPOLOGY: linear ( v i i ) IMMEDIATE SOURCE:
    ( B ) CLONE: F9, F10

( x i ) SEQUENCE DESCRIPTION: SEQ ID NO:29:

```
Lys Ala Asn Cys Gln Cys Pro Pro Asp Thr Arg Pro Gly Glu Ile Gly
1               5                   10                  15
Cys Ile Glu
```

( 2 ) INFORMATION FOR SEQ ID NO:30:

( i ) SEQUENCE CHARACTERISTICS:
    ( A ) LENGTH: 24 amino acids
    ( B ) TYPE: amino acid
    ( D ) TOPOLOGY: linear ( v i i ) IMMEDIATE SOURCE:
    ( B ) CLONE: F12

( x i ) SEQUENCE DESCRIPTION: SEQ ID NO:30:

```
Ala Glu Ser Ser Ile Cys Ser Asp Phe Gly Asn Glu Phe Cys Arg Asn
1               5                   10                  15
Ala Glu Cys Glu Val Val Pro Gly
                20
```

( 2 ) INFORMATION FOR SEQ ID NO:31:

( i ) SEQUENCE CHARACTERISTICS:
    ( A ) LENGTH: 21 amino acids
    ( B ) TYPE: amino acid
    ( D ) TOPOLOGY: linear ( v i i ) IMMEDIATE SOURCE:
    ( B ) CLONE: F14

( x i ) SEQUENCE DESCRIPTION: SEQ ID NO:31:

```
Lys Ala Tyr Glu Cys Thr Cys Pro Ser Gly Ser Thr Val Ala Glu Asp
1               5                   10                  15
Gly Ile Thr Cys Lys
                20
```

( 2 ) INFORMATION FOR SEQ ID NO:32:

( i ) SEQUENCE CHARACTERISTICS:
    ( A ) LENGTH: 21 amino acids
    ( B ) TYPE: amino acid
    ( D ) TOPOLOGY: linear ( v i i ) IMMEDIATE SOURCE:
    ( B ) CLONE: F14

( x i ) SEQUENCE DESCRIPTION: SEQ ID NO:32:

```
Lys  Ala  Tyr  Glu  Cys  Thr  Cys  Pro  Arg  Ala  Phe  Thr  Val  Ala  Glu  Asp
1                  5                        10                       15

Gly  Ile  Thr  Cys  Lys
                20
```

( 2 ) INFORMATION FOR SEQ ID NO:33:

( i ) SEQUENCE CHARACTERISTICS:
        ( A ) LENGTH: 12 amino acids
        ( B ) TYPE: amino acid
        ( D ) TOPOLOGY: linear ( v i i ) IMMEDIATE SOURCE:
        ( B ) CLONE: F15

( x i ) SEQUENCE DESCRIPTION: SEQ ID NO:33:

```
Lys  Asn  Leu  Leu  Gln  Arg  Asp  Ser  Arg  Cys  Cys  Gln
1                  5                        10
```

( 2 ) INFORMATION FOR SEQ ID NO:34:

( i ) SEQUENCE CHARACTERISTICS:
        ( A ) LENGTH: 9 amino acids
        ( B ) TYPE: amino acid
        ( D ) TOPOLOGY: linear ( v i i ) IMMEDIATE SOURCE:
        ( B ) CLONE: F16

( x i ) SEQUENCE DESCRIPTION: SEQ ID NO:34:

```
Lys  Gly  Thr  Val  Leu  Cys  Glu  Cys  Pro
1                  5
```

( 2 ) INFORMATION FOR SEQ ID NO:35:

( i ) SEQUENCE CHARACTERISTICS:
        ( A ) LENGTH: 14 amino acids
        ( B ) TYPE: amino acid
        ( D ) TOPOLOGY: linear ( v i i ) IMMEDIATE SOURCE:
        ( B ) CLONE: F9

( x i ) SEQUENCE DESCRIPTION: SEQ ID NO:35:

```
Lys  Cys  Pro  Cys  Asp  Asn  Met  Tyr  Phe  Asn  Ala  Ala  Glu  Lys
1                  5                        10
```

( 2 ) INFORMATION FOR SEQ ID NO:36:

( i ) SEQUENCE CHARACTERISTICS:
        ( A ) LENGTH: 19 amino acids
        ( B ) TYPE: amino acid
        ( D ) TOPOLOGY: linear ( v i i ) IMMEDIATE SOURCE:
        ( B ) CLONE: F9

( x i ) SEQUENCE DESCRIPTION: SEQ ID NO:36:

```
Lys  Ala  Asn  Arg  Gln  Cys  Pro  Pro  Asp  Thr  Arg  Arg  Gly  Glu  Ile  Gly
1                  5                        10                       15

Cys  Ile  Glu
```

( 2 ) INFORMATION FOR SEQ ID NO:37:

( i ) SEQUENCE CHARACTERISTICS:
        ( A ) LENGTH: 20 base pairs
        ( B ) TYPE: nucleic acid
        ( C ) STRANDEDNESS: single ( D ) TOPOLOGY: linear ( x i ) SEQUENCE DESCRIPTION: SEQ ID NO:37:

TTACCTGGAT CTGGATCCTT                                                                                          20

( 2 ) INFORMATION FOR SEQ ID NO:38:

( i ) SEQUENCE CHARACTERISTICS:
            ( A ) LENGTH: 50 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:38:

TTACCAATGG ATGTACAAAT AGCTTCAAGG ACACCATCTT CGTACCACTT                                                          50

( 2 ) INFORMATION FOR SEQ ID NO:39:

( i ) SEQUENCE CHARACTERISTICS:
            ( A ) LENGTH: 53 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:39:

TTTGGGTACA TCATACACCA TTCACCAATT GGGTGTTCAC AAGCCTGADS CTT                                                      53

( 2 ) INFORMATION FOR SEQ ID NO:40:

( i ) SEQUENCE CHARACTERISTICS:
            ( A ) LENGTH: 14 amino acids
            ( B ) TYPE: amino acid
            ( D ) TOPOLOGY: linear ( v i i ) IMMEDIATE SOURCE:
            ( B ) CLONE: F10

( x i ) SEQUENCE DESCRIPTION: SEQ ID NO:40:

Lys Ala Pro Arg Gln Asn Met Tyr Phe Asn Ala Ala Glu Lys
        1               5                   10

( 2 ) INFORMATION FOR SEQ ID NO:41:

( i ) SEQUENCE CHARACTERISTICS:
            ( A ) LENGTH: 19 amino acids
            ( B ) TYPE: amino acid
            ( D ) TOPOLOGY: linear ( v i i ) IMMEDIATE SOURCE:
            ( B ) CLONE: F10

( x i ) SEQUENCE DESCRIPTION: SEQ ID NO:41:

Lys Cys Asn Cys Asp Cys Pro Pro Asp Thr Arg Pro Gly Glu Ile Gly
        1               5                   10                  15

Cys Ile Glu ( 2 ) INFORMATION FOR SEQ ID NO:42:

( i ) SEQUENCE CHARACTERISTICS:
            ( A ) LENGTH: 24 amino acids
            ( B ) TYPE: amino acid
            ( D ) TOPOLOGY: linear ( v i i ) IMMEDIATE SOURCE:
            ( B ) CLONE: F12

( x i ) SEQUENCE DESCRIPTION: SEQ ID NO:42:

Lys Glu Ser Ser Ile Cys Xaa Asp Phe Gly Asn Glu Phe Cys Arg Asn

```
         1               5               10              15

Ala Glu Cys Glu Val Val Pro Lys
                        20
```

( 2 ) INFORMATION FOR SEQ ID NO:43:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:43:

```
TTTAGGTACA  ACCTCACATT  CAGCATTCCT  ACAAAATTCA  TTACCGAAAT  CAAAACAAAT        60

ACTACTCTCC  TT                                                                72
```

( 2 ) INFORMATION FOR SEQ ID NO:44:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:44:

```
CTTCGACGGA  TTGGATTCGA  CGCATCTGCC  ATAGCTACAT  TCCCTCGTCT  T                 51
```

( 2 ) INFORMATION FOR SEQ ID NO:45:

( i ) SEQUENCE CHARACTERISTICS:
        ( A ) LENGTH: 63 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:45:

```
CTTGCAATGG  ATTCCATCCT  CGGCGACAGT  GAAAGCTCTA  GGGCAAGTGC  ACTCATAAGC        60

CTT                                                                           63
```

( 2 ) INFORMATION FOR SEQ ID NO:46:

( i ) SEQUENCE CHARACTERISTICS:
        ( A ) LENGTH: 19 amino acids
        ( B ) TYPE: amino acid
        ( D ) TOPOLOGY: linear ( v i i ) IMMEDIATE SOURCE:
        ( B ) CLONE: F9 b ( x i ) SEQUENCE DESCRIPTION: SEQ ID NO:46:

```
   Lys Ala Asn Cys Gln Cys Pro Pro Asp Thr Arg Arg Gly Glu Ile Gly
   1               5                   10                  15

Cys Ile Glu
```

( 2 ) INFORMATION FOR SEQ ID NO:47:

( i ) SEQUENCE CHARACTERISTICS:
        ( A ) LENGTH: 9 amino acids
        ( B ) TYPE: amino acid
        ( D ) TOPOLOGY: linear ( v i i ) IMMEDIATE SOURCE:
        ( B ) CLONE: F16

( x i ) SEQUENCE DESCRIPTION: SEQ ID NO:47:

```
   Lys Xaa Xaa Val Leu Cys Glu Xaa Pro
```

( 2 ) INFORMATION FOR SEQ ID NO:48:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:48:

```
ATGTCGAAGA CAACAAAGAA GTTCAACTCT TTATCGATGG ATCCC                    45
```

( 2 ) INFORMATION FOR SEQ ID NO:49:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:49:

```
GAANNNTTC                                                            10
```

( 2 ) INFORMATION FOR SEQ ID NO:50:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:50:

```
TCGATGGATC AGTTCTGT                                                  18
```

( 2 ) INFORMATION FOR SEQ ID NO:51:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:51:

```
CGGTACCCAG TTCTGT                                                    16
```

( 2 ) INFORMATION FOR SEQ ID NO:52:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i v ) ANTI-SENSE: YES ( x i ) SEQUENCE DESCRIPTION: SEQ ID NO:52:

```
ACAGAACTGG GTACCGAGCT                                                20
```

( 2 ) INFORMATION FOR SEQ ID NO:53:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:53:

5,587,311

69 70
-continued

AACGAGCTCG GTACCCAGTC C                                                                              21

(2) INFORMATION FOR SEQ ID NO:54:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (iv) ANTI-SENSE: YES (xi) SEQUENCE DESCRIPTION: SEQ ID NO:54:

GAACTGGGTA CCGAGCTCGT T                                                                              21

(2) INFORMATION FOR SEQ ID NO:55:

(i) SEQUENCE CHARACTERISTICS:
        (A) LENGTH: 2065 base pairs
        (B) TYPE: nucleic acid
        (C) STRANDEDNESS: double
        (D) TOPOLOGY: linear (vii) IMMEDIATE SOURCE:
        (B) CLONE: Figure 7

(ix) FEATURE:
        (A) NAME/KEY: CDS
        (B) LOCATION: 33..1985

(xi) SEQUENCE DESCRIPTION: SEQ ID NO:55:

```
CCGCGACAGC TGCGGTGGTT CGACGCAGTG AG ATG CGT GGC ATC GCT TTG TTC        53
                                    Met Arg Gly Ile Ala Leu Phe
                                     1               5

GTC GCC GCT GTT TCA CTG ATT GTA GAG GGC ACA GCA GAA TCA TCC ATT       101
Val Ala Ala Val Ser Leu Ile Val Glu Gly Thr Ala Glu Ser Ser Ile
         10                  15                  20

TGC TCT GAC TTC GGG AAC GAG TTC TGT CGC AAC GCT GAA TGT GAA GTG       149
Cys Ser Asp Phe Gly Asn Glu Phe Cys Arg Asn Ala Glu Cys Glu Val
     25                  30                  35

GTG CCT GGT GCA GAG GAT GAT TTC GTG TGC AAA TGT CCG CGA GAT AAT       197
Val Pro Gly Ala Glu Asp Asp Phe Val Cys Lys Cys Pro Arg Asp Asn
 40                  45                  50                  55

ATG TAC TTC AAT GCT GCT GAA AAG CAA TGC GAA TAT AAA GAC ACG TGC       245
Met Tyr Phe Asn Ala Ala Glu Lys Gln Cys Glu Tyr Lys Asp Thr Cys
                 60                  65                  70

AAG ACA AGG GAG TGC AGC TAT GGA CGT TGC GTT GAA AGT AAC CCG AGC       293
Lys Thr Arg Glu Cys Ser Tyr Gly Arg Cys Val Glu Ser Asn Pro Ser
             75                  80                  85

AAG GCT AGC TGC GTC TGC GAA GCA TCG GAC GAT CTA ACG CTA CAA TGC       341
Lys Ala Ser Cys Val Cys Glu Ala Ser Asp Asp Leu Thr Leu Gln Cys
         90                  95                 100

AAA ATT AAA AAT GAC TAC GCA ACT GAC TGC CGA AAT CGA GGT GGC ACT       389
Lys Ile Lys Asn Asp Tyr Ala Thr Asp Cys Arg Asn Arg Gly Gly Thr
     105                 110                 115

GCT AAG TTG CGC ACG GAT GGG TTT ATT GGC GCA ACG TGT GAC TGT GGT       437
Ala Lys Leu Arg Thr Asp Gly Phe Ile Gly Ala Thr Cys Asp Cys Gly
120                 125                 130                 135

GAA TGG GGT GCG ATG AAC ATG ACC ACC CGG AAC TGT GTC CCT ACC ACG       485
Glu Trp Gly Ala Met Asn Met Thr Thr Arg Asn Cys Val Pro Thr Thr
                 140                 145                 150

TGT CTT CGT CCC GAC TTG ACC TGC AAA GAC CTC TGC GAG AAA AAC CTG       533
Cys Leu Arg Pro Asp Leu Thr Cys Lys Asp Leu Cys Glu Lys Asn Leu
             155                 160                 165

CTT CAA AGG GAT TCT CGT TGT TGC CAG GGG TGG AAC ACA GCA AAC TGT       581
```

|  |  |  |  |  |  |  |  |  |  |  |  |  |  |  |  |
|---|---|---|---|---|---|---|---|---|---|---|---|---|---|---|---|
| Leu | Gln | Arg 170 | Asp | Ser | Arg | Cys 175 | Cys | Gln | Gly | Trp | Asn | Thr 180 | Ala | Asn | Cys |

| TCA | GCC | GCT | CCT | CCA | GCT | GAC | TCC | TAT | TGC | TCT | CCT | GGG | AGC | CCC | AAA | 629 |
|---|---|---|---|---|---|---|---|---|---|---|---|---|---|---|---|---|
| Ser | Ala | Ala | Pro | Pro | Ala | Asp | Ser | Tyr | Cys | Ser | Pro | Gly | Ser | Pro | Lys | |
| 185 | | | | | 190 | | | | | | 195 | | | | | |

| GGA | CCG | GAC | GGA | CAG | TGT | ATA | AAT | GCT | TGC | AAG | ACG | AAA | GAA | GCT | GGG | 677 |
|---|---|---|---|---|---|---|---|---|---|---|---|---|---|---|---|---|
| Gly | Pro | Asp | Gly | Gln | Cys | Ile | Asn | Ala | Cys | Lys | Thr | Lys | Glu | Ala | Gly | |
| 200 | | | | | 205 | | | | | 210 | | | | | 215 | |

| TTT | GTC | TGC | AAG | CAT | GGA | TGC | AGG | TCG | ACC | GGC | AAG | GCG | TAC | GAG | TGC | 725 |
|---|---|---|---|---|---|---|---|---|---|---|---|---|---|---|---|---|
| Phe | Val | Cys | Lys | His | Gly | Cys | Arg | Ser | Thr | Gly | Lys | Ala | Tyr | Glu | Cys | |
| | | | | 220 | | | | | 225 | | | | | 230 | | |

| ACG | TGC | CCG | AGT | GGC | TCT | ACC | GTC | GCC | GAA | GAT | GGC | ATT | ACC | TGC | AAA | 773 |
|---|---|---|---|---|---|---|---|---|---|---|---|---|---|---|---|---|
| Thr | Cys | Pro | Ser | Gly | Ser | Thr | Val | Ala | Glu | Asp | Gly | Ile | Thr | Cys | Lys | |
| | | | 235 | | | | | 240 | | | | | 245 | | | |

| AGT | ATT | TCG | CAC | ACA | GTC | AGC | TGC | ACT | GCT | GAG | CAA | AAA | CAG | ACC | TGC | 821 |
|---|---|---|---|---|---|---|---|---|---|---|---|---|---|---|---|---|
| Ser | Ile | Ser | His | Thr | Val | Ser | Cys | Thr | Ala | Glu | Gln | Lys | Gln | Thr | Cys | |
| | | 250 | | | | | 255 | | | | | 260 | | | | |

| CGC | CCA | ACC | GAA | GAC | TGT | CGT | GTG | CAC | AAA | GGA | ACT | GTG | TTG | TGT | GAG | 869 |
|---|---|---|---|---|---|---|---|---|---|---|---|---|---|---|---|---|
| Arg | Pro | Thr | Glu | Asp | Cys | Arg | Val | His | Lys | Gly | Thr | Val | Leu | Cys | Glu | |
| 265 | | | | | 270 | | | | | 275 | | | | | | |

| TGC | CCG | TGG | AAT | CAA | CAT | CTA | GTG | GGG | GAC | ACG | TGC | ATA | AGT | GAT | TGC | 917 |
|---|---|---|---|---|---|---|---|---|---|---|---|---|---|---|---|---|
| Cys | Pro | Trp | Asn | Gln | His | Leu | Val | Gly | Asp | Thr | Cys | Ile | Ser | Asp | Cys | |
| 280 | | | | | 285 | | | | | 290 | | | | | 295 | |

| GTC | GAC | AAG | AAA | TGC | CAC | GAA | GAA | TTT | ATG | GAC | TGT | GGC | GTA | TAT | ATG | 965 |
|---|---|---|---|---|---|---|---|---|---|---|---|---|---|---|---|---|
| Val | Asp | Lys | Lys | Cys | His | Glu | Glu | Phe | Met | Asp | Cys | Gly | Val | Tyr | Met | |
| | | | | 300 | | | | | 305 | | | | | 310 | | |

| AAT | CGA | CAA | AGC | TGC | TAT | TGT | CCA | TGG | AAA | TCA | AGG | AAG | CCG | GGC | CCA | 1013 |
|---|---|---|---|---|---|---|---|---|---|---|---|---|---|---|---|---|
| Asn | Arg | Gln | Ser | Cys | Tyr | Cys | Pro | Trp | Lys | Ser | Arg | Lys | Pro | Gly | Pro | |
| | | | 315 | | | | | 320 | | | | | 325 | | | |

| AAT | GTC | AAC | ATC | AAT | GAA | TGC | CTA | CTG | AAT | GAG | TAT | TAC | TAC | ACG | GTG | 1061 |
|---|---|---|---|---|---|---|---|---|---|---|---|---|---|---|---|---|
| Asn | Val | Asn | Ile | Asn | Glu | Cys | Leu | Leu | Asn | Glu | Tyr | Tyr | Tyr | Thr | Val | |
| | | 330 | | | | | 335 | | | | | 340 | | | | |

| TCA | TTC | ACC | CCA | AAC | ATA | TCT | TTT | GAT | TCT | GAC | CAT | TGC | AAA | TGG | TAT | 1109 |
|---|---|---|---|---|---|---|---|---|---|---|---|---|---|---|---|---|
| Ser | Phe | Thr | Pro | Asn | Ile | Ser | Phe | Asp | Ser | Asp | His | Cys | Lys | Trp | Tyr | |
| | | 345 | | | | | 350 | | | | | 355 | | | | |

| GAG | GAT | CGT | GTT | TTG | GAA | GCG | ATA | CGG | ACC | AGT | ATC | GGA | AAA | GAA | GTT | 1157 |
|---|---|---|---|---|---|---|---|---|---|---|---|---|---|---|---|---|
| Glu | Asp | Arg | Val | Leu | Glu | Ala | Ile | Arg | Thr | Ser | Ile | Gly | Lys | Glu | Val | |
| 360 | | | | | 365 | | | | | 370 | | | | | 375 | |

| TTT | AAG | GTT | GAG | ATA | CTT | AAC | TGC | ACG | CAG | GAC | ATT | AAG | GCA | AGA | CTC | 1205 |
|---|---|---|---|---|---|---|---|---|---|---|---|---|---|---|---|---|
| Phe | Lys | Val | Glu | Ile | Leu | Asn | Cys | Thr | Gln | Asp | Ile | Lys | Ala | Arg | Leu | |
| | | | | 380 | | | | | 385 | | | | | 390 | | |

| ATA | GCA | GAG | AAA | CCA | CTG | TCA | AAA | CAC | GTG | CTC | AGG | AAA | CTA | CAA | GCA | 1253 |
|---|---|---|---|---|---|---|---|---|---|---|---|---|---|---|---|---|
| Ile | Ala | Glu | Lys | Pro | Leu | Ser | Lys | His | Val | Leu | Arg | Lys | Leu | Gln | Ala | |
| | | | 395 | | | | | 400 | | | | | 405 | | | |

| TGC | GAG | CAT | CCA | ATC | GGC | GAA | TGG | TGC | ATG | ATG | TAT | CCG | AAG | TTG | CTG | 1301 |
|---|---|---|---|---|---|---|---|---|---|---|---|---|---|---|---|---|
| Cys | Glu | His | Pro | Ile | Gly | Glu | Trp | Cys | Met | Met | Tyr | Pro | Lys | Leu | Leu | |
| | | 410 | | | | | 415 | | | | | 420 | | | | |

| ATC | AAG | AAA | AAC | TCT | GCA | ACA | GAA | ATC | GAA | GAA | GAG | AAC | CTT | TGC | GAC | 1349 |
|---|---|---|---|---|---|---|---|---|---|---|---|---|---|---|---|---|
| Ile | Lys | Lys | Asn | Ser | Ala | Thr | Glu | Ile | Glu | Glu | Glu | Asn | Leu | Cys | Asp | |
| | 425 | | | | | 430 | | | | | 435 | | | | | |

| AGT | CTG | CTC | AAG | GAT | CAG | GAA | GCT | GCC | TAC | AAA | GGT | CAA | AAC | AAA | TGC | 1397 |
|---|---|---|---|---|---|---|---|---|---|---|---|---|---|---|---|---|
| Ser | Leu | Leu | Lys | Asp | Gln | Glu | Ala | Ala | Tyr | Lys | Gly | Gln | Asn | Lys | Cys | |
| 440 | | | | 445 | | | | | 450 | | | | | 455 | | |

| GTC | AAG | GTC | GAC | AAC | CTC | TTC | TGG | TTC | CAG | TGC | GCT | GAT | GGT | TAC | ACA | 1445 |
|---|---|---|---|---|---|---|---|---|---|---|---|---|---|---|---|---|
| Val | Lys | Val | Asp | Asn | Leu | Phe | Trp | Phe | Gln | Cys | Ala | Asp | Gly | Tyr | Thr | |
| | | | | 460 | | | | | 465 | | | | | 470 | | |

| ACA | ACT | TAC | GAG | ATG | ACA | CGA | GGT | CGC | CTA | CGC | CGC | TCC | GTG | TGT | AAA | 1493 |
|---|---|---|---|---|---|---|---|---|---|---|---|---|---|---|---|---|
| Thr | Thr | Tyr | Glu | Met | Thr | Arg | Gly | Arg | Leu | Arg | Arg | Ser | Val | Cys | Lys | |
| | | | 475 | | | | | 480 | | | | | 485 | | | |

| GCT | GGA | GTT | TCT | TGC | AAC | GAA | AAC | GAG | CAG | TCG | GAG | TGT | GCT | GAC | AAA | 1541 |

| | | | | | | | | | | | | | | | |
|---|---|---|---|---|---|---|---|---|---|---|---|---|---|---|---|
| Ala | Gly | Val 490 | Ser | Cys | Asn | Glu 495 | Asn | Glu | Gln | Ser | Glu 500 | Cys | Ala | Asp | Lys |

| | | | | | | | | | | | | | | | |
|---|---|---|---|---|---|---|---|---|---|---|---|---|---|---|---|
| GGG | CAA | ATA | TTT | GTT | TAC | GAA | AAC | GGC | AAA | GCG | AAT | TGC | CAA | TGC | CCA |
| Gly | Gln 505 | Ile | Phe | Val | Tyr | Glu 510 | Asn | Gly | Lys | Ala | Asn 515 | Cys | Gln | Cys | Pro |

1589

| | | | | | | | | | | | | | | | |
|---|---|---|---|---|---|---|---|---|---|---|---|---|---|---|---|
| CCA | GAC | ACT | AAA | CCT | GGG | GAG | ATT | GGC | TGC | ATT | GAG | CGT | ACC | ACA | TGC |
| Pro 520 | Asp | Thr | Lys | Pro | Gly 525 | Glu | Ile | Gly | Cys | Ile 530 | Glu | Arg | Thr | Thr | Cys 535 |

1637

| | | | | | | | | | | | | | | | |
|---|---|---|---|---|---|---|---|---|---|---|---|---|---|---|---|
| AAC | CCT | AAA | GAA | ATA | CAA | GAA | TGC | CAA | GAC | AAG | AAG | CTG | GAG | TGC | GTT |
| Asn | Pro | Lys | Glu | Ile 540 | Gln | Glu | Cys | Gln | Asp 545 | Lys | Lys | Leu | Glu | Cys 550 | Val |

1685

| | | | | | | | | | | | | | | | |
|---|---|---|---|---|---|---|---|---|---|---|---|---|---|---|---|
| TAC | AAA | AAC | CAT | AAA | GCA | GAA | TGC | GAG | TGT | CCT | GAT | GAT | CAC | GAG | TGT |
| Tyr | Lys | Asn | His 555 | Lys | Ala | Glu | Cys | Glu 560 | Cys | Pro | Asp | Asp | His 565 | Glu | Cys |

1733

| | | | | | | | | | | | | | | | |
|---|---|---|---|---|---|---|---|---|---|---|---|---|---|---|---|
| TAC | AGG | GAG | CCT | GCC | AAA | GAC | TCT | TGC | AGT | GAA | GAG | GAT | AAT | GGT | AAA |
| Tyr | Arg | Glu 570 | Pro | Ala | Lys | Asp | Ser 575 | Cys | Ser | Glu | Glu | Asp 580 | Asn | Gly | Lys |

1781

| | | | | | | | | | | | | | | | |
|---|---|---|---|---|---|---|---|---|---|---|---|---|---|---|---|
| TGT | CAA | AGC | AGT | GGG | CAG | CGT | TGT | GTA | ATA | GAA | AAC | GGA | AAG | GCT | GTT |
| Cys | Gln 585 | Ser | Ser | Gly | Gln | Arg 590 | Cys | Val | Ile | Glu | Asn 595 | Gly | Lys | Ala | Val |

1829

| | | | | | | | | | | | | | | | |
|---|---|---|---|---|---|---|---|---|---|---|---|---|---|---|---|
| TGC | AAG | GAA | AAG | TCT | GAA | GCA | ACA | ACA | GCT | GCG | ACT | ACA | ACA | ACG | AAA |
| Cys 600 | Lys | Glu | Lys | Ser | Glu 605 | Ala | Thr | Thr | Ala | Thr 610 | Thr | Thr | Thr | Lys 615 | |

1877

| | | | | | | | | | | | | | | | |
|---|---|---|---|---|---|---|---|---|---|---|---|---|---|---|---|
| GCG | AAA | GAC | AAG | GAT | CCA | GAT | CCT | GGA | AAG | TCA | AGT | GCT | GCA | GCA | GTA |
| Ala | Lys | Asp | Lys | Asp 620 | Pro | Asp | Pro | Gly | Lys 625 | Ser | Ser | Ala | Ala | Ala 630 | Val |

1925

| | | | | | | | | | | | | | | | |
|---|---|---|---|---|---|---|---|---|---|---|---|---|---|---|---|
| TCA | GCT | ACT | GGG | CTC | TTG | TTA | CTG | CTC | GCA | GCT | ACT | TCA | GTC | ACC | GCA |
| Ser | Ala | Thr | Gly 635 | Leu | Leu | Leu | Leu | Leu 640 | Ala | Ala | Thr | Ser | Val 645 | Thr | Ala |

1973

| | | | | | |
|---|---|---|---|---|---|
| GCA | TCG | TTG | TAAGGAAGAT | GTCCAACTTG | AATACGGAAC AGCTTGAATA |
| Ala | Ser | Leu 650 | | | |

2022

TGTATATATA CATCACGCTT ACATCGAACA CCTAGCTTGG TTT   2065

( 2 ) INFORMATION FOR SEQ ID NO:56:

( i ) SEQUENCE CHARACTERISTICS:
        ( A ) LENGTH: 650 amino acids
        ( B ) TYPE: amino acid
        ( D ) TOPOLOGY: linear ( i i ) MOLECULE TYPE: protein ( x i ) SEQUENCE DESCRIPTION: SEQ ID NO:56:

| | | | | | | | | | | | | | | | |
|---|---|---|---|---|---|---|---|---|---|---|---|---|---|---|---|
| Met 1 | Arg | Gly | Ile | Ala 5 | Leu | Phe | Val | Ala | Ala 10 | Val | Ser | Leu | Ile | Val 15 | Glu |
| Gly | Thr | Ala | Glu 20 | Ser | Ser | Ile | Cys | Ser 25 | Asp | Phe | Gly | Asn | Glu 30 | Phe | Cys |
| Arg | Asn | Ala 35 | Glu | Cys | Glu | Val | Val 40 | Pro | Gly | Ala | Glu | Asp 45 | Asp | Phe | Val |
| Cys | Lys 50 | Cys | Pro | Arg | Asp | Asn 55 | Met | Tyr | Phe | Asn | Ala 60 | Ala | Glu | Lys | Gln |
| Cys 65 | Glu | Tyr | Lys | Asp | Thr 70 | Cys | Lys | Thr | Arg | Glu 75 | Cys | Ser | Tyr | Gly | Arg 80 |
| Cys | Val | Glu | Ser | Asn 85 | Pro | Ser | Lys | Ala | Ser 90 | Cys | Val | Cys | Glu | Ala 95 | Ser |
| Asp | Asp | Leu | Thr 100 | Leu | Gln | Cys | Lys | Ile 105 | Lys | Asn | Asp | Tyr | Ala 110 | Thr | Asp |
| Cys | Arg | Asn 115 | Arg | Gly | Gly | Thr | Ala 120 | Lys | Leu | Arg | Thr | Asp 125 | Gly | Phe | Ile |

```
Gly Ala Thr Cys Asp Cys Gly Glu Trp Gly Ala Met Asn Met Thr Thr
        130                 135                 140
Arg Asn Cys Val Pro Thr Cys Leu Arg Pro Asp Leu Thr Cys Lys
145                 150                 155                 160
Asp Leu Cys Glu Lys Asn Leu Leu Gln Arg Asp Ser Arg Cys Cys Gln
                165                 170                 175
Gly Trp Asn Thr Ala Asn Cys Ser Ala Ala Pro Pro Ala Asp Ser Tyr
            180                 185                 190
Cys Ser Pro Gly Ser Pro Lys Gly Pro Asp Gly Gln Cys Ile Asn Ala
        195                 200                 205
Cys Lys Thr Lys Glu Ala Gly Phe Val Cys Lys His Gly Cys Arg Ser
    210                 215                 220
Thr Gly Lys Ala Tyr Glu Cys Thr Cys Pro Ser Gly Ser Thr Val Ala
225                 230                 235                 240
Glu Asp Gly Ile Thr Cys Lys Ser Ile Ser His Thr Val Ser Cys Thr
            245                 250                 255
Ala Glu Gln Lys Gln Thr Cys Arg Pro Thr Glu Asp Cys Arg Val His
        260                 265                 270
Lys Gly Thr Val Leu Cys Glu Cys Pro Trp Asn Gln His Leu Val Gly
    275                 280                 285
Asp Thr Cys Ile Ser Asp Cys Val Asp Lys Lys Cys His Glu Glu Phe
290                 295                 300
Met Asp Cys Gly Val Tyr Met Asn Arg Gln Ser Cys Tyr Cys Pro Trp
305                 310                 315                 320
Lys Ser Arg Lys Pro Gly Pro Asn Val Asn Ile Asn Glu Cys Leu Leu
            325                 330                 335
Asn Glu Tyr Tyr Tyr Thr Val Ser Phe Thr Pro Asn Ile Ser Phe Asp
            340                 345                 350
Ser Asp His Cys Lys Trp Tyr Glu Asp Arg Val Leu Glu Ala Ile Arg
        355                 360                 365
Thr Ser Ile Gly Lys Glu Val Phe Lys Val Glu Ile Leu Asn Cys Thr
    370                 375                 380
Gln Asp Ile Lys Ala Arg Leu Ile Ala Glu Lys Pro Leu Ser Lys His
385                 390                 395                 400
Val Leu Arg Lys Leu Gln Ala Cys Glu His Pro Ile Gly Glu Trp Cys
            405                 410                 415
Met Met Tyr Pro Lys Leu Leu Ile Lys Lys Asn Ser Ala Thr Glu Ile
            420                 425                 430
Glu Glu Glu Asn Leu Cys Asp Ser Leu Leu Lys Asp Gln Glu Ala Ala
        435                 440                 445
Tyr Lys Gly Gln Asn Lys Cys Val Lys Val Asp Asn Leu Phe Trp Phe
    450                 455                 460
Gln Cys Ala Asp Gly Tyr Thr Thr Thr Tyr Glu Met Thr Arg Gly Arg
465                 470                 475                 480
Leu Arg Arg Ser Val Cys Lys Ala Gly Val Ser Cys Asn Glu Asn Glu
            485                 490                 495
Gln Ser Glu Cys Ala Asp Lys Gly Gln Ile Phe Val Tyr Glu Asn Gly
        500                 505                 510
Lys Ala Asn Cys Gln Cys Pro Pro Asp Thr Lys Pro Gly Glu Ile Gly
    515                 520                 525
Cys Ile Glu Arg Thr Thr Cys Asn Pro Lys Glu Ile Gln Glu Cys Gln
530                 535                 540
Asp Lys Lys Leu Glu Cys Val Tyr Lys Asn His Lys Ala Glu Cys Glu
```

```
545                 550                 555                 560
Cys Pro Asp Asp His Glu Cys Tyr Arg Glu Pro Ala Lys Asp Ser Cys
            565                 570                 575

Ser Glu Glu Asp Asn Gly Lys Cys Gln Ser Ser Gly Gln Arg Cys Val
            580                 585                 590

Ile Glu Asn Gly Lys Ala Val Cys Lys Glu Lys Ser Glu Ala Thr Thr
            595                 600                 605

Ala Ala Thr Thr Thr Thr Lys Ala Lys Asp Lys Asp Pro Asp Pro Gly
            610                 615                 620

Lys Ser Ser Ala Ala Ala Val Ser Ala Thr Gly Leu Leu Leu Leu Leu
625                 630                 635                 640

Ala Ala Thr Ser Val Thr Ala Ala Ser Leu
            645                 650
```

( 2 ) INFORMATION FOR SEQ ID NO:57:

( i ) SEQUENCE CHARACTERISTICS:
     ( A ) LENGTH: 688 amino acids
     ( B ) TYPE: amino acid
     ( D ) TOPOLOGY: linear ( x i ) SEQUENCE DESCRIPTION: SEQ ID NO:57:

```
Ala Thr Ala Ala Val Val Arg Arg Ser Glu Met Arg Gly Ile Ala Leu
1               5                   10                  15

Phe Val Ala Ala Val Ser Leu Ile Val Glu Gly Thr Ala Glu Ser Ser
                20                  25                  30

Ile Cys Ser Asp Phe Gly Asn Glu Phe Cys Arg Asn Ala Glu Cys Glu
        35                  40                  45

Val Val Pro Gly Ala Glu Asp Asp Phe Val Cys Lys Cys Pro Arg Asp
    50                  55                  60

Asn Met Tyr Phe Asn Ala Ala Glu Lys Gln Cys Glu Tyr Lys Asp Thr
65                  70                  75                  80

Cys Lys Thr Arg Glu Cys Ser Tyr Gly Arg Cys Val Glu Ser Asn Pro
                85                  90                  95

Ser Lys Ala Ser Cys Val Cys Glu Ala Ser Asp Asp Leu Thr Leu Gln
            100                 105                 110

Cys Lys Ile Lys Asn Asp Tyr Ala Thr Asp Cys Arg Asn Arg Gly Gly
            115                 120                 125

Thr Ala Lys Leu Arg Thr Asp Gly Phe Ile Gly Ala Thr Cys Asp Cys
            130                 135                 140

Gly Glu Trp Gly Ala Met Asn Met Thr Thr Arg Asn Cys Val Pro Thr
145                 150                 155                 160

Thr Cys Leu Arg Pro Asp Leu Thr Cys Lys Asp Leu Cys Glu Lys Asn
                165                 170                 175

Leu Leu Gln Arg Asp Ser Arg Cys Cys Gln Gly Trp Asn Thr Ala Asn
            180                 185                 190

Cys Ser Ala Ala Pro Pro Ala Asp Ser Tyr Cys Ser Pro Gly Ser Pro
            195                 200                 205

Lys Gly Pro Asp Gly Gln Cys Ile Asn Ala Cys Lys Thr Lys Glu Ala
            210                 215                 220

Gly Phe Val Cys Lys His Gly Cys Arg Ser Thr Gly Lys Ala Tyr Glu
225                 230                 235                 240

Cys Thr Cys Pro Ser Gly Ser Thr Val Ala Glu Asp Gly Ile Thr Cys
                245                 250                 255

Lys Ser Ile Ser His Thr Val Ser Cys Thr Ala Glu Gln Lys Gln Thr
            260                 265                 270
```

```
Cys Arg Pro Thr Glu Asp Cys Arg Val His Lys Gly Thr Val Leu Cys
        275                 280                 285
Glu Cys Pro Trp Asn Gln His Leu Val Gly Asp Thr Cys Ile Ser Asp
    290                 295                 300
Cys Val Asp Lys Lys Cys His Glu Glu Phe Met Asp Cys Gly Val Tyr
305                     310                 315                 320
Met Asn Arg Gln Ser Cys Tyr Cys Pro Trp Lys Ser Arg Lys Pro Gly
                325                 330                 335
Pro Asn Val Asn Ile Asn Glu Cys Leu Leu Asn Glu Tyr Tyr Tyr Thr
            340                 345                 350
Val Ser Phe Thr Pro Asn Ile Ser Phe Asp Ser Asp His Cys Lys Trp
        355                 360                 365
Tyr Glu Asp Arg Val Leu Glu Ala Ile Arg Thr Ser Ile Gly Lys Glu
    370                 375                 380
Val Phe Lys Val Glu Ile Leu Asn Cys Thr Gln Asp Ile Lys Ala Arg
385                 390                 395                 400
Leu Ile Ala Glu Lys Pro Leu Ser Lys His Val Leu Arg Lys Leu Gln
                405                 410                 415
Ala Cys Glu His Pro Ile Gly Glu Trp Cys Met Met Tyr Pro Lys Leu
            420                 425                 430
Leu Ile Lys Lys Asn Ser Ala Thr Glu Ile Glu Glu Glu Asn Leu Cys
        435                 440                 445
Asp Ser Leu Leu Lys Asp Gln Glu Ala Ala Tyr Lys Gly Gln Asn Lys
    450                 455                 460
Cys Val Lys Val Asp Asn Leu Phe Trp Phe Gln Cys Ala Asp Gly Tyr
465                 470                 475                 480
Thr Thr Thr Tyr Glu Met Thr Arg Gly Arg Leu Arg Arg Ser Val Cys
                485                 490                 495
Lys Ala Gly Val Ser Cys Asn Glu Asn Glu Gln Ser Glu Cys Ala Asp
            500                 505                 510
Lys Gly Gln Ile Phe Val Tyr Glu Asn Gly Lys Ala Asn Cys Gln Cys
        515                 520                 525
Pro Pro Asp Thr Lys Pro Gly Glu Ile Gly Cys Ile Glu Arg Thr Thr
    530                 535                 540
Cys Asn Pro Lys Glu Ile Gln Glu Cys Gln Asp Lys Lys Leu Glu Cys
545                 550                 555                 560
Val Tyr Lys Asn His Lys Ala Glu Cys Cys Pro Asp His Glu
                565                 570                 575
Cys Tyr Arg Glu Pro Ala Lys Asp Ser Cys Ser Glu Glu Asp Asn Gly
            580                 585                 590
Lys Cys Gln Ser Ser Gly Gln Arg Cys Val Ile Glu Asn Gly Lys Ala
        595                 600                 605
Val Cys Lys Glu Lys Ser Glu Ala Thr Thr Ala Ala Thr Thr Thr Thr
    610                 615                 620
Lys Ala Lys Asp Lys Asp Pro Asp Pro Gly Lys Ser Ser Ala Ala Ala
625                 630                 635                 640
Val Ser Ala Thr Gly Leu Leu Leu Leu Leu Ala Ala Thr Ser Val Thr
                645                 650                 655
Ala Ala Ser Leu Xaa Gly Arg Cys Pro Thr Xaa Ile Arg Asn Ser Leu
            660                 665                 670
Asn Met Tyr Ile Tyr Ile Thr Leu Thr Ser Asn Thr Xaa Leu Gly Phe
        675                 680                 685
```

( 2 ) INFORMATION FOR SEQ ID NO:58:

( i ) SEQUENCE CHARACTERISTICS:
        ( A ) LENGTH: 2259 base pairs
        ( B ) TYPE: nucleic acid
        ( C ) STRANDEDNESS: double
        ( D ) TOPOLOGY: linear ( v i i ) IMMEDIATE SOURCE:
        ( B ) CLONE: Figure 12

( i x ) FEATURE:
        ( A ) NAME/KEY: CDS
        ( B ) LOCATION: 52..2004

( x i ) SEQUENCE DESCRIPTION: SEQ ID NO:58:

```
GAATTCGCGG  CCGCGAAAGT  GCGACAGCTG  CGGTGGTTCG  ACGCAGTCGA  G ATG CGT                57
                                                              Met Arg
                                                                1

GGC ATC GCT TTG TTC GTC GCC GCT GTT TCA CTG ATT GTA GAG GGC ACA                      105
Gly Ile Ala Leu Phe Val Ala Ala Val Ser Leu Ile Val Glu Gly Thr
         5              10                  15

GCA GAA TCA TCC ATT TGC TCT GAC TTC GGG AAC GAG TTC TGT CGC AAC                      153
Ala Glu Ser Ser Ile Cys Ser Asp Phe Gly Asn Glu Phe Cys Arg Asn
     20                  25                  30

GCT GAA TGT GAA GTG GTG CCT GGT GCA GAG GAT GAT TTC GTG TGC AAA                      201
Ala Glu Cys Glu Val Val Pro Gly Ala Glu Asp Asp Phe Val Cys Lys
 35              40                  45                      50

TGT CCG CGA GAT AAT ATG TAC TTC AAT GCT GCT GAA AAG CAA TGC GAA                      249
Cys Pro Arg Asp Asn Met Tyr Phe Asn Ala Ala Glu Lys Gln Cys Glu
             55                  60                  65

TAT AAA GAC ACG TGC AAA ACA AGG GAG TGC AGC TAT GGA CGT TGC GTT                      297
Tyr Lys Asp Thr Cys Lys Thr Arg Glu Cys Ser Tyr Gly Arg Cys Val
             70                  75              80

GAA AGT AAC CCG AGC AAG GCT AGC TGC GTC TGC GAA GCA TCG GAC GAT                      345
Glu Ser Asn Pro Ser Lys Ala Ser Cys Val Cys Glu Ala Ser Asp Asp
         85                  90                  95

CTA ACG CTA CAA TGC AAA ATT AAA AAT GAC TAC GCA ACT GAC TGC CGA                      393
Leu Thr Leu Gln Cys Lys Ile Lys Asn Asp Tyr Ala Thr Asp Cys Arg
    100                 105                 110

AAC CGA GGT GGC ACT GCT AAG TTG CGC ACG GAT GGG TTT ATT GGC GCA                      441
Asn Arg Gly Gly Thr Ala Lys Leu Arg Thr Asp Gly Phe Ile Gly Ala
115                 120                 125                 130

ACG TGT GAC TGT GGT GAA TGG GGT GCG ATG AAC ATG ACC ACC CGG AAC                      489
Thr Cys Asp Cys Gly Glu Trp Gly Ala Met Asn Met Thr Thr Arg Asn
                135                 140                 145

TGT GTC CCT ACC ACG TGT CTT CGT CCC GAC TTG AGC TGC AAA GAC CTC                      537
Cys Val Pro Thr Thr Cys Leu Arg Pro Asp Leu Ser Cys Lys Asp Leu
            150                 155                 160

TGC GAG AAA AAC CTG CTT CAA AGG GAT TCT CGT TGT TGC CAG GGG TGG                      585
Cys Glu Lys Asn Leu Leu Gln Arg Asp Ser Arg Cys Cys Gln Gly Trp
        165                 170                 175

AAC ACA GCA AAC TGT TCA GCC GCT CCT CCA GCT GAC TCC TAT TGC TCT                      633
Asn Thr Ala Asn Cys Ser Ala Ala Pro Pro Ala Asp Ser Tyr Cys Ser
    180                 185                 190

CCT GGG AGC CCC AAA GGA CCG GAC GGA CAG TGT ATA AAT GCT TGC AAG                      681
Pro Gly Ser Pro Lys Gly Pro Asp Gly Gln Cys Ile Asn Ala Cys Lys
195                 200                 205                 210

ATG AAA GAA GCT GGG TTT GTC TGC AAG CAT GGA TGC AGG TCG ACC GCC                      729
Met Lys Glu Ala Gly Phe Val Cys Lys His Gly Cys Arg Ser Thr Ala
                215                 220                 225

AAG GCG TAC GAG TGC ACG TGC CCA CGT GCC TTT ACC GTC GCG GAA GAT                      777
Lys Ala Tyr Glu Cys Thr Cys Pro Arg Ala Phe Thr Val Ala Glu Asp
            230                 235                 240
```

| | | | | | | | | | | | | | | | | |
|---|---|---|---|---|---|---|---|---|---|---|---|---|---|---|---|---|
| GGC | ATT | ACC | TGC | AAA | AGT | ATT | TCG | CAC | ACA | GTC | AGC | TGC | ACT | GCT | GAG | 825 |
| Gly | Ile | Thr | Cys | Lys | Ser | Ile | Ser | His | Thr | Val | Ser | Cys | Thr | Ala | Glu | |
| | | 245 | | | | | 250 | | | | | 255 | | | | |
| CAA | AAA | CAG | ACC | TGC | CGC | CCA | ACC | GAA | GAC | TGT | CGT | GTG | CAC | AAA | GGA | 873 |
| Gln | Lys | Gln | Thr | Cys | Arg | Pro | Thr | Glu | Asp | Cys | Arg | Val | His | Lys | Gly | |
| | 260 | | | | | 265 | | | | | 270 | | | | | |
| ACT | GTG | TTG | TGT | GAG | TGC | CCG | TGG | AAT | CAA | CAT | CTA | GTG | GGG | GAC | ACG | 921 |
| Thr | Val | Leu | Cys | Glu | Cys | Pro | Trp | Asn | Gln | His | Leu | Val | Gly | Asp | Thr | |
| 275 | | | | | 280 | | | | | 285 | | | | | 290 | |
| TGC | ATA | AGT | GAT | TGC | GTC | GAC | AAG | AAA | TGC | CAC | GAA | GAA | TTT | ATG | GAC | 969 |
| Cys | Ile | Ser | Asp | Cys | Val | Asp | Lys | Lys | Cys | His | Glu | Glu | Phe | Met | Asp | |
| | | | | 295 | | | | | 300 | | | | | 305 | | |
| TGT | GGC | GTA | TAT | ATG | AAT | CGA | CAA | AGC | TGC | TAT | TGT | CCA | TGG | AAA | TCA | 1017 |
| Cys | Gly | Val | Tyr | Met | Asn | Arg | Gln | Ser | Cys | Tyr | Cys | Pro | Trp | Lys | Ser | |
| | | | 310 | | | | | 315 | | | | | 320 | | | |
| AGG | AAG | CCG | GGC | CCA | AAT | GTC | AAC | ATC | AAT | GGA | TGC | CTA | CTG | AAT | GAG | 1065 |
| Arg | Lys | Pro | Gly | Pro | Asn | Val | Asn | Ile | Asn | Gly | Cys | Leu | Leu | Asn | Glu | |
| | 325 | | | | | 330 | | | | | 335 | | | | | |
| TAT | TAC | TAC | ACG | GTG | TCA | TTC | ACC | CCA | AAC | ATA | TCT | TTT | GAT | TCT | GAC | 1113 |
| Tyr | Tyr | Tyr | Thr | Val | Ser | Phe | Thr | Pro | Asn | Ile | Ser | Phe | Asp | Ser | Asp | |
| | 340 | | | | | 345 | | | | | 350 | | | | | |
| CAT | TGC | AAA | TGG | TAT | GAG | GAT | CGT | GTT | TTG | GAA | GCG | ATA | CGG | ACC | AGT | 1161 |
| His | Cys | Lys | Trp | Tyr | Glu | Asp | Arg | Val | Leu | Glu | Ala | Ile | Arg | Thr | Ser | |
| 355 | | | | | 360 | | | | | 365 | | | | | 370 | |
| ATC | GGA | AAA | GAA | GTT | TTT | AAG | GTT | GAG | ATA | CTT | AAC | TGC | ACG | CAG | GAC | 1209 |
| Ile | Gly | Lys | Glu | Val | Phe | Lys | Val | Glu | Ile | Leu | Asn | Cys | Thr | Gln | Asp | |
| | | | | 375 | | | | | 380 | | | | | 385 | | |
| ATT | AAG | GCA | AGA | CTC | ATA | GCA | GAG | AAA | TTA | CTG | TCA | AAA | CAC | GTG | CTC | 1257 |
| Ile | Lys | Ala | Arg | Leu | Ile | Ala | Glu | Lys | Leu | Leu | Ser | Lys | His | Val | Leu | |
| | | | 390 | | | | | 395 | | | | | 400 | | | |
| AGG | AAA | CTA | CAA | GCA | TGC | GAG | CAT | CCA | ATC | GGC | GAA | TGG | TGC | ATG | ATG | 1305 |
| Arg | Lys | Leu | Gln | Ala | Cys | Glu | His | Pro | Ile | Gly | Glu | Trp | Cys | Met | Met | |
| | | 405 | | | | | 410 | | | | | 415 | | | | |
| TAT | CCG | AAG | TTG | CTG | ATC | AAG | AAA | AAC | TCT | GCA | ACA | GAA | ATC | GAA | GAA | 1353 |
| Tyr | Pro | Lys | Leu | Leu | Ile | Lys | Lys | Asn | Ser | Ala | Thr | Glu | Ile | Glu | Glu | |
| | 420 | | | | | 425 | | | | | 430 | | | | | |
| GAG | AAC | CTT | TGC | GAC | AGT | CTG | CTC | AAG | GAT | CAG | GAA | GCT | GCC | TAC | AAA | 1401 |
| Glu | Asn | Leu | Cys | Asp | Ser | Leu | Leu | Lys | Asp | Gln | Glu | Ala | Ala | Tyr | Lys | |
| 435 | | | | | 440 | | | | | 445 | | | | | 450 | |
| GGT | CAA | AAC | AAA | TGC | GTC | AAG | GTC | GAC | AAC | CTC | TTC | TGG | TTC | CAG | TGC | 1449 |
| Gly | Gln | Asn | Lys | Cys | Val | Lys | Val | Asp | Asn | Leu | Phe | Trp | Phe | Gln | Cys | |
| | | | | 455 | | | | | 460 | | | | | 465 | | |
| GCT | GAT | GGT | TAC | ACA | ACA | ACT | TAC | GAG | ATG | ACA | CGA | GGT | CGC | CTA | CGC | 1497 |
| Ala | Asp | Gly | Tyr | Thr | Thr | Thr | Tyr | Glu | Met | Thr | Arg | Gly | Arg | Leu | Arg | |
| | | | 470 | | | | | 475 | | | | | 480 | | | |
| CGC | TCC | GTG | TGT | AAA | GCT | GGA | GTT | TCT | TGC | AAC | GAA | AAC | GAG | CAG | TCG | 1545 |
| Arg | Ser | Val | Cys | Lys | Ala | Gly | Val | Ser | Cys | Asn | Glu | Asn | Glu | Gln | Ser | |
| | | 485 | | | | | 490 | | | | | 495 | | | | |
| GAG | TGT | GCT | GAC | AAA | GGG | CAA | ATA | TGT | GTT | TAC | GAA | AAC | GGC | AAA | GCG | 1593 |
| Glu | Cys | Ala | Asp | Lys | Gly | Gln | Ile | Cys | Val | Tyr | Glu | Asn | Gly | Lys | Ala | |
| | 500 | | | | | 505 | | | | | 510 | | | | | |
| AAT | TGC | CAA | TGC | CCA | CCA | GAC | ACT | AAA | CCT | GGG | GAG | ATT | GGC | TGC | ATT | 1641 |
| Asn | Cys | Gln | Cys | Pro | Pro | Asp | Thr | Lys | Pro | Gly | Glu | Ile | Gly | Cys | Ile | |
| 515 | | | | | 520 | | | | | 525 | | | | | 530 | |
| GAG | CGT | ACC | ACA | TGC | AAC | CCT | AAA | GAG | ATA | CAA | GAA | TGC | CAA | GAC | AAG | 1689 |
| Glu | Arg | Thr | Thr | Cys | Asn | Pro | Lys | Glu | Ile | Gln | Glu | Cys | Gln | Asp | Lys | |
| | | | | 535 | | | | | 540 | | | | | 545 | | |
| AAG | CTG | GAG | TGC | GTT | TAC | AAA | AAC | CAT | AAA | GCA | GAA | TSS | AAG | TGT | CCT | 1737 |
| Lys | Leu | Glu | Cys | Val | Tyr | Lys | Asn | His | Lys | Ala | Glu | Xaa | Lys | Cys | Pro | |
| | | 550 | | | | | 555 | | | | | 560 | | | | |

```
GAT GAT CAC GAG TGT TAC AGG GAG CCT GCC AAA GAC TCT TGC AGT GAA          1785
Asp Asp His Glu Cys Tyr Arg Glu Pro Ala Lys Asp Ser Cys Ser Glu
        565                 570                 575

GAG GAT AAT GGT AAA TGT CAA AGC AGT GGG CAG CGT TGT GTA ATA GAA          1833
Glu Asp Asn Gly Lys Cys Gln Ser Ser Gly Gln Arg Cys Val Ile Glu
    580                 585                 590

AAC GGA AAG GCT GTT TGC AAG GAA AAG TCT GAA GCA ACA ACA GCT GCG          1881
Asn Gly Lys Ala Val Cys Lys Glu Lys Ser Glu Ala Thr Thr Ala Ala
595                 600                 605                 610

ACT ACA ACA ACG AAA GCG AAA GAC AAG GAT CCA GAT CCT GGA AAG TCA          1929
Thr Thr Thr Thr Lys Ala Lys Asp Lys Asp Pro Asp Pro Gly Lys Ser
            615                 620                 625

AGT GCT GCA GCA GTA TCA GCT ACT GGG CTC TTG TTA CTG CTC GCA GCT          1977
Ser Ala Ala Ala Val Ser Ala Thr Gly Leu Leu Leu Leu Leu Ala Ala
                630                 635                 640

ACT TCA GTC ACC GCA GCA TCG TTG TAAGGAAGAT GTCCAACTTG AATACGGAAC         2031
Thr Ser Val Thr Ala Ala Ser Leu
            645                 650

AGCTTGAATA TGTATATATA CATCACGCTT ACATCGAACA CCTAGCTTGG TTTTTGGAAT        2091

TTCAATATTG CGCATTGGTA CTCACGGCAA CATGAATGTA TTACTTTAGA ATGACAGGGA        2151

AGAGGGACGT GAAAGGAGTT TCCTTGTCTG AACATATCAA AGAAAATTTT CCCCTATCCG        2211

ACCGATGTCA AATAAAGATA GTTGGGTCTA ACAGCGGCC GCGAATTC                     2259
```

( 2 ) INFORMATION FOR SEQ ID NO:59:

( i ) SEQUENCE CHARACTERISTICS:
        ( A ) LENGTH: 650 amino acids
        ( B ) TYPE: amino acid
        ( D ) TOPOLOGY: linear ( i i ) MOLECULE TYPE: protein ( x i ) SEQUENCE DESCRIPTION: SEQ ID NO:59:

```
Met Arg Gly Ile Ala Leu Phe Val Ala Ala Val Ser Leu Ile Val Glu
 1               5                  10                  15

Gly Thr Ala Glu Ser Ser Ile Cys Ser Asp Phe Gly Asn Glu Phe Cys
            20                  25                  30

Arg Asn Ala Glu Cys Glu Val Val Pro Gly Ala Glu Asp Asp Phe Val
            35                  40                  45

Cys Lys Cys Pro Arg Asp Asn Met Tyr Phe Asn Ala Ala Glu Lys Gln
        50                  55                  60

Cys Glu Tyr Lys Asp Thr Cys Lys Thr Arg Glu Cys Ser Tyr Gly Arg
 65                 70                  75                  80

Cys Val Glu Ser Asn Pro Ser Lys Ala Ser Cys Val Cys Glu Ala Ser
                85                  90                  95

Asp Asp Leu Thr Leu Gln Cys Lys Ile Lys Asn Asp Tyr Ala Thr Asp
            100                 105                 110

Cys Arg Asn Arg Gly Gly Thr Ala Lys Leu Arg Thr Asp Gly Phe Ile
            115                 120                 125

Gly Ala Thr Cys Asp Cys Gly Glu Trp Gly Ala Met Asn Met Thr Thr
        130                 135                 140

Arg Asn Cys Val Pro Thr Thr Cys Leu Arg Pro Asp Leu Ser Cys Lys
145                 150                 155                 160

Asp Leu Cys Glu Lys Asn Leu Leu Gln Arg Asp Ser Arg Cys Cys Gln
                165                 170                 175

Gly Trp Asn Thr Ala Asn Cys Ser Ala Ala Pro Pro Ala Asp Ser Tyr
            180                 185                 190
```

```
Cys Ser Pro Gly Ser Pro Lys Gly Pro Asp Gly Gln Cys Ile Asn Ala
        195                 200                 205

Cys Lys Met Lys Glu Ala Gly Phe Val Cys Lys His Gly Cys Arg Ser
    210                 215                 220

Thr Ala Lys Ala Tyr Glu Cys Thr Cys Pro Arg Ala Phe Thr Val Ala
225                 230                 235                 240

Glu Asp Gly Ile Thr Cys Lys Ser Ile Ser His Thr Val Ser Cys Thr
                245                 250                 255

Ala Glu Gln Lys Gln Thr Cys Arg Pro Thr Glu Asp Cys Arg Val His
            260                 265                 270

Lys Gly Thr Val Leu Cys Glu Cys Pro Trp Asn Gln His Leu Val Gly
        275                 280                 285

Asp Thr Cys Ile Ser Asp Cys Val Asp Lys Lys Cys His Glu Glu Phe
    290                 295                 300

Met Asp Cys Gly Val Tyr Met Asn Arg Gln Ser Cys Tyr Cys Pro Trp
305                 310                 315                 320

Lys Ser Arg Lys Pro Gly Pro Asn Val Asn Ile Asn Gly Cys Leu Leu
                325                 330                 335

Asn Glu Tyr Tyr Tyr Thr Val Ser Phe Thr Pro Asn Ile Ser Phe Asp
            340                 345                 350

Ser Asp His Cys Lys Trp Tyr Glu Asp Arg Val Leu Glu Ala Ile Arg
        355                 360                 365

Thr Ser Ile Gly Lys Glu Val Phe Lys Val Glu Ile Leu Asn Cys Thr
    370                 375                 380

Gln Asp Ile Lys Ala Arg Leu Ile Ala Glu Lys Leu Leu Ser Lys His
385                 390                 395                 400

Val Leu Arg Lys Leu Gln Ala Cys Glu His Pro Ile Gly Glu Trp Cys
                405                 410                 415

Met Met Tyr Pro Lys Leu Leu Ile Lys Lys Asn Ser Ala Thr Glu Ile
            420                 425                 430

Glu Glu Glu Asn Leu Cys Asp Ser Leu Leu Lys Asp Gln Glu Ala Ala
        435                 440                 445

Tyr Lys Gly Gln Asn Lys Cys Val Lys Val Asp Asn Leu Phe Trp Phe
    450                 455                 460

Gln Cys Ala Asp Gly Tyr Thr Thr Thr Tyr Glu Met Thr Arg Gly Arg
465                 470                 475                 480

Leu Arg Arg Ser Val Cys Lys Ala Gly Val Ser Cys Asn Glu Asn Glu
                485                 490                 495

Gln Ser Glu Cys Ala Asp Lys Gly Gln Ile Cys Val Tyr Glu Asn Gly
        500                 505                 510

Lys Ala Asn Cys Gln Cys Pro Asp Thr Lys Pro Gly Glu Ile Gly
    515                 520                 525

Cys Ile Glu Arg Thr Thr Cys Asn Pro Lys Glu Ile Gln Glu Cys Gln
530                 535                 540

Asp Lys Lys Leu Glu Cys Val Tyr Lys Asn His Lys Ala Glu Xaa Lys
545                 550                 555                 560

Cys Pro Asp Asp His Glu Cys Tyr Arg Glu Pro Ala Lys Asp Ser Cys
                565                 570                 575

Ser Glu Glu Asp Asn Gly Lys Cys Gln Ser Ser Gly Gln Arg Cys Val
        580                 585                 590

Ile Glu Asn Gly Lys Ala Val Cys Lys Glu Lys Ser Glu Ala Thr Thr
    595                 600                 605

Ala Ala Thr Thr Thr Thr Lys Ala Lys Asp Lys Asp Pro Asp Pro Gly
```

| | | | | | | | | | | | | | | | | |
|---|---|---|---|---|---|---|---|---|---|---|---|---|---|---|---|---|
| | | | | 610 | | | | 615 | | | | 620 | | | | |
| Lys | Ser | Ser | Ala | Ala | Ala | Val | Ser | Ala | Thr | Gly | Leu | Leu | Leu | Leu | Leu | |
| 625 | | | | | 630 | | | | 635 | | | | | | 640 | |
| Ala | Ala | Thr | Ser | Val | Thr | Ala | Ala | Ser | Leu | | | | | | | |
| | | | | 645 | | | | | 650 | | | | | | | |

( 2 ) INFORMATION FOR SEQ ID NO:60:

( i ) SEQUENCE CHARACTERISTICS:
        ( A ) LENGTH: 1647 base pairs
        ( B ) TYPE: nucleic acid
        ( C ) STRANDEDNESS: double
        ( D ) TOPOLOGY: linear ( v i i ) IMMEDIATE SOURCE:
        ( B ) CLONE: Figure 13

( i x ) FEATURE:
        ( A ) NAME/KEY: CDS
        ( B ) LOCATION: 1..1647

( x i ) SEQUENCE DESCRIPTION: SEQ ID NO:60:

| | | | | | | | | | | | | | | | | |
|---|---|---|---|---|---|---|---|---|---|---|---|---|---|---|---|---|
| GTT | GAA | AGT | AAC | CCG | AGC | AAG | GCT | AGC | TGC | GTC | TGC | GAA | CGA | TCG | GAC | 48 |
| Val | Glu | Ser | Asn | Pro | Ser | Lys | Ala | Ser | Cys | Val | Cys | Glu | Arg | Ser | Asp | |
| 1 | | | | 5 | | | | | 10 | | | | | 15 | | |
| GAT | CTA | ACG | CTA | CAA | TGC | AAA | ATT | AAA | AAT | GAC | TAC | GCA | ACT | GAC | TGC | 96 |
| Asp | Leu | Thr | Leu | Gln | Cys | Lys | Ile | Lys | Asn | Asp | Tyr | Ala | Thr | Asp | Cys | |
| | | | 20 | | | | | 25 | | | | | 30 | | | |
| CGA | AAT | CGA | GGT | GGC | ACT | GCT | AAG | TTG | CGC | ACG | GAT | GGG | TTT | ATT | GGC | 144 |
| Arg | Asn | Arg | Gly | Gly | Thr | Ala | Lys | Leu | Arg | Thr | Asp | Gly | Phe | Ile | Gly | |
| | | 35 | | | | 40 | | | | | 45 | | | | | |
| GCA | ACG | TGT | GAC | TGT | GGT | GAA | TGG | GGT | GCG | ATG | AAC | ATG | ACC | ACC | CGG | 192 |
| Ala | Thr | Cys | Asp | Cys | Gly | Glu | Trp | Gly | Ala | Met | Asn | Met | Thr | Thr | Arg | |
| | 50 | | | | | 55 | | | | | 60 | | | | | |
| AAC | TGT | GTC | CCT | ACC | ACG | TGT | CTT | CGT | CCC | GAC | TTG | ACC | TGC | AAA | GAC | 240 |
| Asn | Cys | Val | Pro | Thr | Thr | Cys | Leu | Arg | Pro | Asp | Leu | Thr | Cys | Lys | Asp | |
| 65 | | | | | 70 | | | | | 75 | | | | | 80 | |
| CTC | TGC | GAG | AAA | AAC | CTG | CTT | CAA | AGG | GAT | TCT | CGT | TGT | TGC | CAG | GGG | 288 |
| Leu | Cys | Glu | Lys | Asn | Leu | Leu | Gln | Arg | Asp | Ser | Arg | Cys | Cys | Gln | Gly | |
| | | | | 85 | | | | | 90 | | | | | 95 | | |
| TGG | AAC | ACA | GCA | AAC | TGT | TCA | GCC | GCT | CCT | CCA | GCT | GAC | TCC | TAT | TGC | 336 |
| Trp | Asn | Thr | Ala | Asn | Cys | Ser | Ala | Ala | Pro | Pro | Ala | Asp | Ser | Tyr | Cys | |
| | | | 100 | | | | | 105 | | | | | 110 | | | |
| TCT | CCT | GGG | AGC | CCC | AAA | GGA | CCG | GAC | GGA | CAG | TGT | ATA | AAT | GCT | TGC | 384 |
| Ser | Pro | Gly | Ser | Pro | Lys | Gly | Pro | Asp | Gly | Gln | Cys | Ile | Asn | Ala | Cys | |
| | | 115 | | | | 120 | | | | | 125 | | | | | |
| AAG | ATG | AAA | GAA | GCT | GGG | TTT | GTC | TGC | GAG | CAT | GGA | TGC | AGG | TCG | ACC | 432 |
| Lys | Met | Lys | Glu | Ala | Gly | Phe | Val | Cys | Glu | His | Gly | Cys | Arg | Ser | Thr | |
| | 130 | | | | | 135 | | | | | 140 | | | | | |
| GCC | AAG | GCG | TAC | GAG | TGC | ACG | TGC | CCA | CGT | GGC | TTT | ACC | GTC | GCG | GAA | 480 |
| Ala | Lys | Ala | Tyr | Glu | Cys | Thr | Cys | Pro | Arg | Gly | Phe | Thr | Val | Ala | Glu | |
| 145 | | | | | 150 | | | | | 155 | | | | | 160 | |
| GAT | GGC | ATT | ACC | TGC | AAA | AGT | ATT | TCG | CAC | ACA | GTC | AGC | TGC | ACT | GCT | 528 |
| Asp | Gly | Ile | Thr | Cys | Lys | Ser | Ile | Ser | His | Thr | Val | Ser | Cys | Thr | Ala | |
| | | | | 165 | | | | | 170 | | | | | 175 | | |
| GAG | CAA | AAA | CAG | ACC | TGC | CGC | CCA | ACC | GAA | GAC | TGT | CGT | GTG | CAC | AAA | 576 |
| Glu | Gln | Lys | Gln | Thr | Cys | Arg | Pro | Thr | Glu | Asp | Cys | Arg | Val | His | Lys | |
| | | | 180 | | | | | 185 | | | | | 190 | | | |
| GGA | ACT | GTG | TTG | TGT | GAG | TGC | CCG | TGG | AAT | CAA | CAT | CTA | GTG | GGG | GAC | 624 |
| Gly | Thr | Val | Leu | Cys | Glu | Cys | Pro | Trp | Asn | Gln | His | Leu | Val | Gly | Asp | |
| | | 195 | | | | 200 | | | | | 205 | | | | | |
| ACG | TGC | ATA | AGT | GAT | TGC | GTC | GAC | AAG | AAA | TGC | CAC | GAA | GAA | TTT | ATG | 672 |
| Thr | Cys | Ile | Ser | Asp | Cys | Val | Asp | Lys | Lys | Cys | His | Glu | Glu | Phe | Met | |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| GAC | TGT | GGC | GTA | TAT | ATG | AAT | CGA | CAA | AGC | TGT | TAT | TGT | CCA | TGG | AAA | 720  |
| Asp | Cys | Gly | Val | Tyr | Met | Asn | Arg | Gln | Ser | Cys | Tyr | Cys | Pro | Trp | Lys |      |
| 225 |     |     |     |     | 230 |     |     |     | 235 |     |     |     |     |     | 240 |      |
| TCA | AGG | AAG | CCG | GGC | CCA | AAT | GTC | AAC | ATC | AAT | GGA | TGC | CTA | CTG | AAT | 768  |
| Ser | Arg | Lys | Pro | Gly | Pro | Asn | Val | Asn | Ile | Asn | Gly | Cys | Leu | Leu | Asn |      |
|     |     |     |     | 245 |     |     |     |     | 250 |     |     |     |     | 255 |     |      |
| GAG | TAT | TAC | TAC | ACG | GTG | TCA | TTC | ACC | CCA | AAC | ATA | TCT | TTT | GAT | TCT | 816  |
| Glu | Tyr | Tyr | Tyr | Thr | Val | Ser | Phe | Thr | Pro | Asn | Ile | Ser | Phe | Asp | Ser |      |
|     |     |     | 260 |     |     |     |     | 265 |     |     |     |     | 270 |     |     |      |
| GAC | CAT | TGC | AAA | TGG | TAT | GAG | GAT | CGT | GTT | TTG | GAA | GCG | ATA | CGG | ACC | 864  |
| Asp | His | Cys | Lys | Trp | Tyr | Glu | Asp | Arg | Val | Leu | Glu | Ala | Ile | Arg | Thr |      |
|     |     | 275 |     |     |     | 280 |     |     |     |     | 285 |     |     |     |     |      |
| AGT | ATC | GGA | AAA | GAA | GTT | TTT | AAG | GTT | GAG | ATA | CTT | AAC | TGC | ACG | CAG | 912  |
| Ser | Ile | Gly | Lys | Glu | Val | Phe | Lys | Val | Glu | Ile | Leu | Asn | Cys | Thr | Gln |      |
|     | 290 |     |     |     | 295 |     |     |     |     | 300 |     |     |     |     |     |      |
| GAC | ATT | AAG | GCA | AGA | CTC | ATA | GCA | GAG | AAA | CCA | CTG | TCA | AAC | CAC | GTG | 960  |
| Asp | Ile | Lys | Ala | Arg | Leu | Ile | Ala | Glu | Lys | Pro | Leu | Ser | Asn | His | Val |      |
| 305 |     |     |     |     | 310 |     |     |     |     | 315 |     |     |     |     | 320 |      |
| CTC | AGG | AAA | CTA | CAA | GCA | TGC | GAG | CAT | CCA | ATC | GGC | GAA | TGG | TGC | ATG | 1008 |
| Leu | Arg | Lys | Leu | Gln | Ala | Cys | Glu | His | Pro | Ile | Gly | Glu | Trp | Cys | Met |      |
|     |     |     |     | 325 |     |     |     |     | 330 |     |     |     |     | 335 |     |      |
| ATG | TAT | CCG | AAG | TTG | CTG | ATC | AAG | AAA | AAC | TCT | GCA | ACA | GAA | ATC | GAA | 1056 |
| Met | Tyr | Pro | Lys | Leu | Leu | Ile | Lys | Lys | Asn | Ser | Ala | Thr | Glu | Ile | Glu |      |
|     |     |     | 340 |     |     |     |     | 345 |     |     |     |     | 350 |     |     |      |
| GAA | GAG | AAC | CTT | TGC | GAC | AGT | CTG | CTC | AAG | AAT | CAG | GAA | GCT | GCC | TAC | 1104 |
| Glu | Glu | Asn | Leu | Cys | Asp | Ser | Leu | Leu | Lys | Asn | Gln | Glu | Ala | Ala | Tyr |      |
|     |     | 355 |     |     |     |     | 360 |     |     |     |     | 365 |     |     |     |      |
| AAA | GGT | CAA | AAC | AAA | TGC | GTC | AAG | GTC | GAC | AAC | CTC | TTC | TGG | TTC | CAG | 1152 |
| Lys | Gly | Gln | Asn | Lys | Cys | Val | Lys | Val | Asp | Asn | Leu | Phe | Trp | Phe | Gln |      |
|     | 370 |     |     |     |     | 375 |     |     |     |     | 380 |     |     |     |     |      |
| TGC | GCT | GAT | GGT | TAC | ACA | ACA | ACT | TAC | GAG | ATG | ACA | CGA | GGT | CGC | CTA | 1200 |
| Cys | Ala | Asp | Gly | Tyr | Thr | Thr | Thr | Tyr | Glu | Met | Thr | Arg | Gly | Arg | Leu |      |
| 385 |     |     |     |     | 390 |     |     |     |     | 395 |     |     |     |     | 400 |      |
| CGC | CGC | TCC | GTG | TGT | AAA | GCT | GGA | GTT | TCT | TGC | AAC | GAA | AAC | GAG | CAG | 1248 |
| Arg | Arg | Ser | Val | Cys | Lys | Ala | Gly | Val | Ser | Cys | Asn | Glu | Asn | Glu | Gln |      |
|     |     |     |     | 405 |     |     |     |     | 410 |     |     |     |     | 415 |     |      |
| TTG | GAG | TGT | GCT | GAC | AAA | GGG | CAA | ATA | TGT | GTT | TAC | GAA | AAC | GGC | AAA | 1296 |
| Leu | Glu | Cys | Ala | Asp | Lys | Gly | Gln | Ile | Cys | Val | Tyr | Glu | Asn | Gly | Lys |      |
|     |     |     | 420 |     |     |     |     | 425 |     |     |     |     | 430 |     |     |      |
| GCG | AAT | TGC | CAA | TGC | CCA | CCA | GAC | ACT | AAA | CCT | GGG | GAG | ATT | GGC | TGC | 1344 |
| Ala | Asn | Cys | Gln | Cys | Pro | Pro | Asp | Thr | Lys | Pro | Gly | Glu | Ile | Gly | Cys |      |
|     |     | 435 |     |     |     |     | 440 |     |     |     |     | 445 |     |     |     |      |
| ATT | GAG | CGT | ACC | ACA | TGC | AAC | CCT | AAA | GAG | ATA | CAA | GAA | TGC | CAA | GAC | 1392 |
| Ile | Glu | Arg | Thr | Thr | Cys | Asn | Pro | Lys | Glu | Ile | Gln | Glu | Cys | Gln | Asp |      |
| 450 |     |     |     |     | 455 |     |     |     |     | 460 |     |     |     |     |     |      |
| AAG | AAG | CTG | GAG | TGC | GTT | TAC | AAA | AAC | CAT | AAA | GCA | GAA | TGC | AAG | TGT | 1440 |
| Lys | Lys | Leu | Glu | Cys | Val | Tyr | Lys | Asn | His | Lys | Ala | Glu | Cys | Lys | Cys |      |
| 465 |     |     |     |     | 470 |     |     |     | 475 |     |     |     |     |     | 480 |      |
| CCT | GAT | GAT | CAC | GAG | TGT | TCC | AGG | GAG | CCT | GCC | AAA | GAC | TCT | TGC | AGT | 1488 |
| Pro | Asp | Asp | His | Glu | Cys | Ser | Arg | Glu | Pro | Ala | Lys | Asp | Ser | Cys | Ser |      |
|     |     |     |     | 485 |     |     |     |     | 490 |     |     |     |     | 495 |     |      |
| GAA | GAG | GAT | AAT | GGT | AAA | TGT | CAA | AGC | AGT | GGG | CAG | CGT | TGT | GTA | ATA | 1536 |
| Glu | Glu | Asp | Asn | Gly | Lys | Cys | Gln | Ser | Ser | Gly | Gln | Arg | Cys | Val | Ile |      |
|     |     |     | 500 |     |     |     |     | 505 |     |     |     |     | 510 |     |     |      |
| GAA | AAC | GGA | AAG | GCT | GTT | TGC | AAG | GAA | AAG | TCT | GAA | GCA | ACA | ACA | GCT | 1584 |
| Glu | Asn | Gly | Lys | Ala | Val | Cys | Lys | Glu | Lys | Ser | Glu | Ala | Thr | Thr | Ala |      |
|     |     | 515 |     |     |     |     | 520 |     |     |     |     | 525 |     |     |     |      |
| GCG | ACT | ACA | ACA | ACG | AAA | GCG | AAA | GAC | AAG | GAT | CCA | GAT | CCT | GGA | AAG | 1632 |
| Ala | Thr | Thr | Thr | Thr | Lys | Ala | Lys | Asp | Lys | Asp | Pro | Asp | Pro | Gly | Lys |      |

|  | 530 |  |  |  | 535 |  |  |  | 540 |  |  |  |
|---|---|---|---|---|---|---|---|---|---|---|---|---|
| TCA | AGT | GCT | GCA | GCA |  |  |  |  |  |  |  | 1647 |
| Ser | Ser | Ala | Ala | Ala |  |  |  |  |  |  |  |  |
| 545 |  |  |  |  |  |  |  |  |  |  |  |  |

( 2 ) INFORMATION FOR SEQ ID NO:61:

( i ) SEQUENCE CHARACTERISTICS:
        ( A ) LENGTH: 549 amino acids
        ( B ) TYPE: amino acid
        ( D ) TOPOLOGY: linear ( i i ) MOLECULE TYPE: protein ( x i ) SEQUENCE DESCRIPTION: SEQ ID NO:61:

| Val | Glu | Ser | Asn | Pro | Ser | Lys | Ala | Ser | Cys | Val | Cys | Glu | Arg | Ser | Asp |
|---|---|---|---|---|---|---|---|---|---|---|---|---|---|---|---|
| 1 |  |  |  | 5 |  |  |  |  | 10 |  |  |  |  | 15 |  |
| Asp | Leu | Thr | Leu | Gln | Cys | Lys | Ile | Lys | Asn | Asp | Tyr | Ala | Thr | Asp | Cys |
|  |  |  | 20 |  |  |  |  | 25 |  |  |  |  | 30 |  |  |
| Arg | Asn | Arg | Gly | Gly | Thr | Ala | Lys | Leu | Arg | Thr | Asp | Gly | Phe | Ile | Gly |
|  |  | 35 |  |  |  |  | 40 |  |  |  |  | 45 |  |  |  |
| Ala | Thr | Cys | Asp | Cys | Gly | Glu | Trp | Gly | Ala | Met | Asn | Met | Thr | Thr | Arg |
|  | 50 |  |  |  |  | 55 |  |  |  |  | 60 |  |  |  |  |
| Asn | Cys | Val | Pro | Thr | Thr | Cys | Leu | Arg | Pro | Asp | Leu | Thr | Cys | Lys | Asp |
| 65 |  |  |  |  | 70 |  |  |  |  | 75 |  |  |  |  | 80 |
| Leu | Cys | Glu | Lys | Asn | Leu | Leu | Gln | Arg | Asp | Ser | Arg | Cys | Cys | Gln | Gly |
|  |  |  |  | 85 |  |  |  |  | 90 |  |  |  |  | 95 |  |
| Trp | Asn | Thr | Ala | Asn | Cys | Ser | Ala | Ala | Pro | Pro | Ala | Asp | Ser | Tyr | Cys |
|  |  |  | 100 |  |  |  |  | 105 |  |  |  |  | 110 |  |  |
| Ser | Pro | Gly | Ser | Pro | Lys | Gly | Pro | Asp | Gly | Gln | Cys | Ile | Asn | Ala | Cys |
|  |  | 115 |  |  |  |  | 120 |  |  |  |  | 125 |  |  |  |
| Lys | Met | Lys | Glu | Ala | Gly | Phe | Val | Cys | Glu | His | Gly | Cys | Arg | Ser | Thr |
|  | 130 |  |  |  |  | 135 |  |  |  |  | 140 |  |  |  |  |
| Ala | Lys | Ala | Tyr | Glu | Cys | Thr | Cys | Pro | Arg | Gly | Phe | Thr | Val | Ala | Glu |
| 145 |  |  |  |  | 150 |  |  |  |  | 155 |  |  |  |  | 160 |
| Asp | Gly | Ile | Thr | Cys | Lys | Ser | Ile | Ser | His | Thr | Val | Ser | Cys | Thr | Ala |
|  |  |  |  | 165 |  |  |  |  | 170 |  |  |  |  | 175 |  |
| Glu | Gln | Lys | Gln | Thr | Cys | Arg | Pro | Thr | Glu | Asp | Cys | Arg | Val | His | Lys |
|  |  |  | 180 |  |  |  |  | 185 |  |  |  |  | 190 |  |  |
| Gly | Thr | Val | Leu | Cys | Glu | Cys | Pro | Trp | Asn | Gln | His | Leu | Val | Gly | Asp |
|  |  | 195 |  |  |  |  | 200 |  |  |  |  | 205 |  |  |  |
| Thr | Cys | Ile | Ser | Asp | Cys | Val | Asp | Lys | Lys | Cys | His | Glu | Glu | Phe | Met |
|  | 210 |  |  |  |  | 215 |  |  |  |  | 220 |  |  |  |  |
| Asp | Cys | Gly | Val | Tyr | Met | Asn | Arg | Gln | Ser | Cys | Tyr | Cys | Pro | Trp | Lys |
| 225 |  |  |  |  | 230 |  |  |  |  | 235 |  |  |  |  | 240 |
| Ser | Arg | Lys | Pro | Gly | Pro | Asn | Val | Asn | Ile | Asn | Gly | Cys | Leu | Leu | Asn |
|  |  |  |  | 245 |  |  |  |  | 250 |  |  |  |  | 255 |  |
| Glu | Tyr | Tyr | Tyr | Thr | Val | Ser | Phe | Thr | Pro | Asn | Ile | Ser | Phe | Asp | Ser |
|  |  |  | 260 |  |  |  |  | 265 |  |  |  |  | 270 |  |  |
| Asp | His | Cys | Lys | Trp | Tyr | Glu | Asp | Arg | Val | Leu | Glu | Ala | Ile | Arg | Thr |
|  |  | 275 |  |  |  |  | 280 |  |  |  |  | 285 |  |  |  |
| Ser | Ile | Gly | Lys | Glu | Val | Phe | Lys | Val | Glu | Ile | Leu | Asn | Cys | Thr | Gln |
|  | 290 |  |  |  |  | 295 |  |  |  |  | 300 |  |  |  |  |
| Asp | Ile | Lys | Ala | Arg | Leu | Ile | Ala | Glu | Lys | Pro | Leu | Ser | Asn | His | Val |
| 305 |  |  |  |  | 310 |  |  |  |  | 315 |  |  |  |  | 320 |
| Leu | Arg | Lys | Leu | Gln | Ala | Cys | Glu | His | Pro | Ile | Gly | Glu | Trp | Cys | Met |
|  |  |  |  | 325 |  |  |  |  | 330 |  |  |  |  | 335 |  |

```
Met  Tyr  Pro  Lys  Leu  Leu  Ile  Lys  Lys  Asn  Ser  Ala  Thr  Glu  Ile  Glu
               340                 345                      350

Glu  Glu  Asn  Leu  Cys  Asp  Ser  Leu  Leu  Lys  Asn  Gln  Glu  Ala  Ala  Tyr
          355                      360                 365

Lys  Gly  Gln  Asn  Lys  Cys  Val  Lys  Val  Asp  Asn  Leu  Phe  Trp  Phe  Gln
     370                 375                      380

Cys  Ala  Asp  Gly  Tyr  Thr  Thr  Tyr  Glu  Met  Thr  Arg  Gly  Arg  Leu
385                      390                 395                           400

Arg  Arg  Ser  Val  Cys  Lys  Ala  Gly  Val  Ser  Cys  Asn  Glu  Asn  Glu  Gln
               405                      410                           415

Leu  Glu  Cys  Ala  Asp  Lys  Gly  Gln  Ile  Cys  Val  Tyr  Glu  Asn  Gly  Lys
               420                      425                      430

Ala  Asn  Cys  Gln  Cys  Pro  Pro  Asp  Thr  Lys  Pro  Gly  Glu  Ile  Gly  Cys
          435                      440                      445

Ile  Glu  Arg  Thr  Thr  Cys  Asn  Pro  Lys  Glu  Ile  Gln  Glu  Cys  Gln  Asp
     450                      455                      460

Lys  Lys  Leu  Glu  Cys  Val  Tyr  Lys  Asn  His  Lys  Ala  Glu  Cys  Lys  Cys
465                      470                 475                           480

Pro  Asp  Asp  His  Glu  Cys  Ser  Arg  Glu  Pro  Ala  Lys  Asp  Ser  Cys  Ser
               485                      490                           495

Glu  Glu  Asp  Asn  Gly  Lys  Cys  Gln  Ser  Ser  Gly  Gln  Arg  Cys  Val  Ile
               500                      505                      510

Glu  Asn  Gly  Lys  Ala  Val  Cys  Lys  Glu  Lys  Ser  Glu  Ala  Thr  Thr  Ala
          515                      520                      525

Ala  Thr  Thr  Thr  Thr  Lys  Ala  Lys  Asp  Lys  Asp  Pro  Asp  Pro  Gly  Lys
     530                      535                      540

Ser  Ser  Ala  Ala  Ala
545
```

(2) INFORMATION FOR SEQ ID NO:62:

(i) SEQUENCE CHARACTERISTICS:
        (A) LENGTH: 2308 base pairs
        (B) TYPE: nucleic acid
        (C) STRANDEDNESS: double
        (D) TOPOLOGY: linear (vii) IMMEDIATE SOURCE:
        (B) CLONE: Figure 14

(ix) FEATURE:
        (A) NAME/KEY: CDS
        (B) LOCATION: 58..2010

(xi) SEQUENCE DESCRIPTION: SEQ ID NO:62:

```
CCCCCTCGAG  GTCGACGGTA  TCGATAAGCT  TGATATCGAA  TTCCGCCGGC  CGCCGAG                57

ATG  CGT  GGC  ATC  GCT  TTG  TTC  GTC  GCC  GCT  GTT  TCA  CTG  ATT  GTA  GAG    105
Met  Arg  Gly  Ile  Ala  Leu  Phe  Val  Ala  Ala  Val  Ser  Leu  Ile  Val  Glu
 1             5                       10                      15

TGC  ACA  GCA  GAA  TCA  TCC  ATT  TGC  TCT  GAC  TTC  GGG  AAC  GAG  TTC  TGT    153
Cys  Thr  Ala  Glu  Ser  Ser  Ile  Cys  Ser  Asp  Phe  Gly  Asn  Glu  Phe  Cys
               20                       25                      30

CGC  AAC  GCT  GAA  TGT  GAA  GTG  GTG  CCT  GGT  GCA  GAG  GAT  GAT  TTC  GTG    201
Arg  Asn  Ala  Glu  Cys  Glu  Val  Val  Pro  Gly  Ala  Glu  Asp  Asp  Phe  Val
          35                       40                       45

TGC  AAA  TGT  CCG  CGA  GAT  AAT  ATG  TAC  TTC  AAT  GCT  GCT  GAA  AAG  CAA    249
Cys  Lys  Cys  Pro  Arg  Asp  Asn  Met  Tyr  Phe  Asn  Ala  Ala  Glu  Lys  Gln
     50                       55                            60

TGC  GAA  TAT  AAA  GAC  ACG  TGC  AAG  ACA  AGG  GAG  TGC  AGC  TAT  GGA  CGT    297
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| Cys | Glu | Tyr | Lys | Asp | Thr | Cys | Lys | Thr | Arg | Glu | Cys | Ser | Tyr | Gly | Arg |      |
| 65  |     |     |     |     | 70  |     |     |     | 75  |     |     |     |     |     | 80  |      |
| TGC | GTT | GAA | AGT | AAC | CCG | AGC | AAG | GCT | AGC | TGC | GTC | TGC | GAA | GCA | TCG | 345  |
| Cys | Val | Glu | Ser | Asn | Pro | Ser | Lys | Ala | Ser | Cys | Val | Cys | Glu | Ala | Ser |      |
|     |     |     |     | 85  |     |     |     |     | 90  |     |     |     |     | 95  |     |      |
| GAC | GAT | CTA | ACG | CTA | CAA | TGC | AAA | ATT | AAA | AAT | GAC | TAC | GCA | ACT | GAC | 393  |
| Asp | Asp | Leu | Thr | Leu | Gln | Cys | Lys | Ile | Lys | Asn | Asp | Tyr | Ala | Thr | Asp |      |
|     |     |     | 100 |     |     |     |     | 105 |     |     |     |     | 110 |     |     |      |
| TGC | CGA | AAT | CGA | GGT | GGC | ACT | GCT | AAG | TTG | CGC | ACG | GAT | GGG | TTT | ATT | 441  |
| Cys | Arg | Asn | Arg | Gly | Gly | Thr | Ala | Lys | Leu | Arg | Thr | Asp | Gly | Phe | Ile |      |
|     |     | 115 |     |     |     |     | 120 |     |     |     |     | 125 |     |     |     |      |
| GGC | GCA | ACG | TGT | GAC | TGT | GGT | GAA | TGG | GGT | GCG | ATG | AAC | ATG | ACC | ACC | 489  |
| Gly | Ala | Thr | Cys | Asp | Cys | Gly | Glu | Trp | Gly | Ala | Met | Asn | Met | Thr | Thr |      |
|     | 130 |     |     |     | 135 |     |     |     |     | 140 |     |     |     |     |     |      |
| CGG | AAC | TGT | GTC | CCT | ACC | ACG | TGT | CTT | CGT | CCC | GAC | TTG | ACC | TGC | AAA | 537  |
| Arg | Asn | Cys | Val | Pro | Thr | Thr | Cys | Leu | Arg | Pro | Asp | Leu | Thr | Cys | Lys |      |
| 145 |     |     |     |     | 150 |     |     |     |     | 155 |     |     |     |     | 160 |      |
| GAC | CTC | TGC | GAG | AAA | AAC | CTG | CTT | CAA | AGG | GAT | TCT | CGT | TGT | TGC | CAG | 585  |
| Asp | Leu | Cys | Glu | Lys | Asn | Leu | Leu | Gln | Arg | Asp | Ser | Arg | Cys | Cys | Gln |      |
|     |     |     |     | 165 |     |     |     |     | 170 |     |     |     |     | 175 |     |      |
| GGG | TGG | AAC | ACA | GCA | AAC | TGT | TCA | GCC | GCT | CCT | CCA | GCT | GAC | TCC | TAT | 633  |
| Gly | Trp | Asn | Thr | Ala | Asn | Cys | Ser | Ala | Ala | Pro | Pro | Ala | Asp | Ser | Tyr |      |
|     |     |     | 180 |     |     |     |     | 185 |     |     |     |     | 190 |     |     |      |
| TGC | TCT | CCT | GGG | AGC | CCC | AAA | GGA | CCG | GAC | GGA | CAG | TGT | ATA | AAT | GCT | 681  |
| Cys | Ser | Pro | Gly | Ser | Pro | Lys | Gly | Pro | Asp | Gly | Gln | Cys | Ile | Asn | Ala |      |
|     |     | 195 |     |     |     |     | 200 |     |     |     |     | 205 |     |     |     |      |
| TGC | AAG | ATG | AAA | GAA | GCT | GGG | TTT | GTC | TGC | GAG | CAT | GGA | TGC | AGG | TCG | 729  |
| Cys | Lys | Met | Lys | Glu | Ala | Gly | Phe | Val | Cys | Glu | His | Gly | Cys | Arg | Ser |      |
|     | 210 |     |     |     |     | 215 |     |     |     |     | 220 |     |     |     |     |      |
| ACC | GCC | AAG | GCG | TAC | GAG | TGC | ACG | TGC | CCA | CGT | GGC | TTT | ACC | GTC | GCG | 777  |
| Thr | Ala | Lys | Ala | Tyr | Glu | Cys | Thr | Cys | Pro | Arg | Gly | Phe | Thr | Val | Ala |      |
| 225 |     |     |     | 230 |     |     |     |     | 235 |     |     |     |     |     | 240 |      |
| GAA | GAT | GGC | ATT | ACC | TGC | AAA | AGT | ATT | TCG | CAC | ACA | GTC | AGC | TGC | ACT | 825  |
| Glu | Asp | Gly | Ile | Thr | Cys | Lys | Ser | Ile | Ser | His | Thr | Val | Ser | Cys | Thr |      |
|     |     |     |     | 245 |     |     |     |     | 250 |     |     |     |     | 255 |     |      |
| GCT | GAG | CAA | AAA | CAG | ACC | TGC | CGC | CCA | ACC | GAA | GAC | TGT | CGT | GTG | CAC | 873  |
| Ala | Glu | Gln | Lys | Gln | Thr | Cys | Arg | Pro | Thr | Glu | Asp | Cys | Arg | Val | His |      |
|     |     |     | 260 |     |     |     |     | 265 |     |     |     |     | 270 |     |     |      |
| AAA | GGA | ACT | GTG | TTG | TGT | GAG | TGC | CCG | TGG | AAT | CAA | CAT | CTA | GTG | GGG | 921  |
| Lys | Gly | Thr | Val | Leu | Cys | Glu | Cys | Pro | Trp | Asn | Gln | His | Leu | Val | Gly |      |
|     |     | 275 |     |     |     |     | 280 |     |     |     |     | 285 |     |     |     |      |
| GAC | ACG | TGC | ATA | AGT | GAT | TGC | GTC | GAC | AAG | AAA | TGC | CAC | GAA | GAA | TTT | 969  |
| Asp | Thr | Cys | Ile | Ser | Asp | Cys | Val | Asp | Lys | Lys | Cys | His | Glu | Glu | Phe |      |
|     | 290 |     |     |     |     | 295 |     |     |     |     | 300 |     |     |     |     |      |
| ATG | GAC | TGT | GGC | GTA | TAT | ATG | AAT | CGA | CAA | AGC | TGC | TAT | TGT | CCA | TGG | 1017 |
| Met | Asp | Cys | Gly | Val | Tyr | Met | Asn | Arg | Gln | Ser | Cys | Tyr | Cys | Pro | Trp |      |
| 305 |     |     |     |     | 310 |     |     |     |     | 315 |     |     |     |     | 320 |      |
| AAA | TCA | AGG | AAG | CCG | GGC | CCA | AAT | GTC | AAC | ATC | AAT | GGA | TGC | CTA | CTG | 1065 |
| Lys | Ser | Arg | Lys | Pro | Gly | Pro | Asn | Val | Asn | Ile | Asn | Gly | Cys | Leu | Leu |      |
|     |     |     |     | 325 |     |     |     |     | 330 |     |     |     |     | 335 |     |      |
| AAT | GAG | TAT | TAC | TAC | ACG | GTG | TCA | TTC | ACC | CCA | AAC | ATA | TCT | TTT | GAT | 1113 |
| Asn | Glu | Tyr | Tyr | Tyr | Thr | Val | Ser | Phe | Thr | Pro | Asn | Ile | Ser | Phe | Asp |      |
|     |     |     | 340 |     |     |     |     | 345 |     |     |     |     | 350 |     |     |      |
| TCT | GAC | CAT | TGC | AAA | TGG | TAT | GAG | GAT | CGT | GTT | TTG | GAA | GCG | ATA | CGG | 1161 |
| Ser | Asp | His | Cys | Lys | Trp | Tyr | Glu | Asp | Arg | Val | Leu | Glu | Ala | Ile | Arg |      |
|     |     | 355 |     |     |     |     | 360 |     |     |     |     | 365 |     |     |     |      |
| ACC | AGT | ATC | GGA | AAA | GAA | GTT | TTT | AAG | GTT | GAG | ATA | CTT | AAC | TGC | ACG | 1209 |
| Thr | Ser | Ile | Gly | Lys | Glu | Val | Phe | Lys | Val | Glu | Ile | Leu | Asn | Cys | Thr |      |
|     | 370 |     |     |     | 375 |     |     |     |     | 380 |     |     |     |     |     |      |
| CAG | GAC | ATT | AAG | GCA | AGA | CTC | ATA | GCA | GAG | AAA | CCA | CTG | TCA | AAC | CAC | 1257 |

```
Gln  Asp  Ile  Lys  Ala  Arg  Leu  Ile  Ala  Glu  Lys  Pro  Leu  Ser  Asn  His
385            390                 395                      400

GTG  CTC  AGG  AAA  CTA  CAA  GCA  TGC  GAG  CAT  CCA  ATC  GGC  GAA  TGG  TGC       1305
Val  Leu  Arg  Lys  Leu  Gln  Ala  Cys  Glu  His  Pro  Ile  Gly  Glu  Trp  Cys
               405                      410                      415

ATG  ATG  TAT  CCG  AAG  TTG  CTG  ATC  AAG  AAA  AAC  TCT  GCA  ACA  GAA  ATC       1353
Met  Met  Tyr  Pro  Lys  Leu  Leu  Ile  Lys  Lys  Asn  Ser  Ala  Thr  Glu  Ile
               420                      425                      430

GAA  GAA  GAG  AAC  CTT  TGC  GAC  AGT  CTG  CTC  AAG  AAT  CAG  GAA  GCT  GCC       1401
Glu  Glu  Glu  Asn  Leu  Cys  Asp  Ser  Leu  Leu  Lys  Asn  Gln  Glu  Ala  Ala
          435                      440                      445

TAC  AAA  GGT  CAA  AAC  AAA  TGC  GTC  AAG  GTC  GAC  AAC  CTC  TTC  TGG  TTC       1449
Tyr  Lys  Gly  Gln  Asn  Lys  Cys  Val  Lys  Val  Asp  Asn  Leu  Phe  Trp  Phe
     450                      455                      460

CAG  TGC  GCT  GAT  GGT  TAC  ACA  ACA  ACT  TAC  GAG  ATG  ACA  CGA  GGT  CGC       1497
Gln  Cys  Ala  Asp  Gly  Tyr  Thr  Thr  Thr  Tyr  Glu  Met  Thr  Arg  Gly  Arg
465                 470                      475                      480

CTA  CGC  CGC  TCC  GTG  TGT  AAA  GCT  GGA  GTT  TCT  TGC  AAC  GAA  AAC  GAG       1545
Leu  Arg  Arg  Ser  Val  Cys  Lys  Ala  Gly  Val  Ser  Cys  Asn  Glu  Asn  Glu
               485                      490                      495

CAG  TTG  GAG  TGT  GCT  GAC  AAA  GGG  CAA  ATA  TGT  GTT  TAC  GAA  AAC  GGC       1593
Gln  Leu  Glu  Cys  Ala  Asp  Lys  Gly  Gln  Ile  Cys  Val  Tyr  Glu  Asn  Gly
               500                      505                      510

AAA  GCG  AAT  TGC  CAA  TGC  CCA  CCA  GAC  ACT  AAA  CCT  GGG  GAG  ATT  GGC       1641
Lys  Ala  Asn  Cys  Gln  Cys  Pro  Pro  Asp  Thr  Lys  Pro  Gly  Glu  Ile  Gly
          515                      520                      525

TGC  ATT  GAG  CGT  ACC  ACA  TGC  AAC  CCT  AAA  GAG  ATA  CAA  GAA  TGC  CAA       1689
Cys  Ile  Glu  Arg  Thr  Thr  Cys  Asn  Pro  Lys  Glu  Ile  Gln  Glu  Cys  Gln
     530                      535                      540

GAC  AAG  AAG  CTG  GAG  TGC  GTT  TAC  AAA  AAC  CAT  AAA  GCA  GAA  TGC  AAG       1737
Asp  Lys  Lys  Leu  Glu  Cys  Val  Tyr  Lys  Asn  His  Lys  Ala  Glu  Cys  Lys
545                      550                      555                      560

TGT  CCT  GAT  GAT  CAC  GAG  TGT  TCC  AGG  GAG  CCT  GCC  AAA  GAC  TCT  TGC       1785
Cys  Pro  Asp  Asp  His  Glu  Cys  Ser  Arg  Glu  Pro  Ala  Lys  Asp  Ser  Cys
               565                      570                      575

AGT  GAA  GAG  GAT  AAT  GGT  AAA  TGT  CAA  AGC  AGT  GGG  CAG  CGT  TGT  GTA       1833
Ser  Glu  Glu  Asp  Asn  Gly  Lys  Cys  Gln  Ser  Ser  Gly  Gln  Arg  Cys  Val
               580                      585                      590

ATA  GAA  AAC  GGA  AAG  GCT  GTT  TGC  AAG  GAA  AAG  TCT  GAA  GCA  ACA  ACA       1881
Ile  Glu  Asn  Gly  Lys  Ala  Val  Cys  Lys  Glu  Lys  Ser  Glu  Ala  Thr  Thr
          595                      600                      605

GCT  GCG  ACT  ACA  ACA  ACG  AAA  GCG  AAA  GAC  AAG  GAT  CCA  GAT  CCT  GGA       1929
Ala  Ala  Thr  Thr  Thr  Thr  Lys  Ala  Lys  Asp  Lys  Asp  Pro  Asp  Pro  Gly
610                      615                      620

AAG  TCA  AGT  GCT  GCA  GCA  GTA  TCA  GCT  ACT  GGG  CTC  TTG  TTA  CTG  CTC       1977
Lys  Ser  Ser  Ala  Ala  Ala  Val  Ser  Ala  Thr  Gly  Leu  Leu  Leu  Leu  Leu
625                      630                      635                      640

GCA  GCT  ACT  TCA  GTC  ACC  GCA  GCA  TCG  TTG  TAAGGAAGMT  GTCCAACTNC              2027
Ala  Ala  Thr  Ser  Val  Thr  Ala  Ala  Ser  Leu
               645                      650

AATACGGAAC  AGCTTGAATA  TGTATATATA  CATCACGCTT  ACATCGAACA  CCTAGCTTGG               2087

TTTTTGGAAT  TTCAATATTG  CGCATTGGTA  CTCACNGCAA  CATGAATGTA  TTACTTTAGA               2147

ATGACAGGGA  AGAGGGACGT  GAAAGGAGTT  TCCTTGTCTG  AACATATCAA  AGAAAATTTT               2207

CCCCTATCCG  ACCGATGTCA  GCGGCCGCGA  ATTCCTGCAG  CCCGGGGGAT  CCACTAGTTC               2267

TAGAGCGGGC  GGCCGCGTTA  ACCACCGCGG  TGGAGCTCCA  G                                    2308
```

( 2 ) INFORMATION FOR SEQ ID NO:63:

( i ) SEQUENCE CHARACTERISTICS:
   ( A ) LENGTH: 650 amino acids
   ( B ) TYPE: amino acid
   ( D ) TOPOLOGY: linear ( i i ) MOLECULE TYPE: protein ( x i ) SEQUENCE DESCRIPTION: SEQ ID NO:63:

| Met | Arg | Gly | Ile | Ala | Leu | Phe | Val | Ala | Ala | Val | Ser | Leu | Ile | Val | Glu |
|---|---|---|---|---|---|---|---|---|---|---|---|---|---|---|---|
| 1 | | | | 5 | | | | | 10 | | | | | 15 | |
| Cys | Thr | Ala | Glu | Ser | Ser | Ile | Cys | Ser | Asp | Phe | Gly | Asn | Glu | Phe | Cys |
| | | | 20 | | | | 25 | | | | | 30 | | | |
| Arg | Asn | Ala | Glu | Cys | Glu | Val | Val | Pro | Gly | Ala | Glu | Asp | Asp | Phe | Val |
| | | 35 | | | | 40 | | | | | 45 | | | | |
| Cys | Lys | Cys | Pro | Arg | Asp | Asn | Met | Tyr | Phe | Asn | Ala | Ala | Glu | Lys | Gln |
| | 50 | | | | | 55 | | | | | | 60 | | | |
| Cys | Glu | Tyr | Lys | Asp | Thr | Cys | Lys | Thr | Arg | Glu | Cys | Ser | Tyr | Gly | Arg |
| 65 | | | | | 70 | | | | | 75 | | | | | 80 |
| Cys | Val | Glu | Ser | Asn | Pro | Ser | Lys | Ala | Ser | Cys | Val | Cys | Glu | Ala | Ser |
| | | | | 85 | | | | | 90 | | | | | 95 | |
| Asp | Asp | Leu | Thr | Leu | Gln | Cys | Lys | Ile | Lys | Asn | Asp | Tyr | Ala | Thr | Asp |
| | | | 100 | | | | | 105 | | | | | 110 | | |
| Cys | Arg | Asn | Arg | Gly | Gly | Thr | Ala | Lys | Leu | Arg | Thr | Asp | Gly | Phe | Ile |
| | | 115 | | | | | 120 | | | | | 125 | | | |
| Gly | Ala | Thr | Cys | Asp | Cys | Gly | Glu | Trp | Gly | Ala | Met | Asn | Met | Thr | Thr |
| | 130 | | | | | 135 | | | | | 140 | | | | |
| Arg | Asn | Cys | Val | Pro | Thr | Thr | Cys | Leu | Arg | Pro | Asp | Leu | Thr | Cys | Lys |
| 145 | | | | | 150 | | | | | 155 | | | | | 160 |
| Asp | Leu | Cys | Glu | Lys | Asn | Leu | Leu | Gln | Arg | Asp | Ser | Arg | Cys | Cys | Gln |
| | | | | 165 | | | | | 170 | | | | | 175 | |
| Gly | Trp | Asn | Thr | Ala | Asn | Cys | Ser | Ala | Ala | Pro | Pro | Ala | Asp | Ser | Tyr |
| | | | 180 | | | | | 185 | | | | | 190 | | |
| Cys | Ser | Pro | Gly | Ser | Pro | Lys | Gly | Pro | Asp | Gly | Gln | Cys | Ile | Asn | Ala |
| | | 195 | | | | | 200 | | | | | 205 | | | |
| Cys | Lys | Met | Lys | Glu | Ala | Gly | Phe | Val | Cys | Glu | His | Gly | Cys | Arg | Ser |
| | 210 | | | | | 215 | | | | | 220 | | | | |
| Thr | Ala | Lys | Ala | Tyr | Glu | Cys | Thr | Cys | Pro | Arg | Gly | Phe | Thr | Val | Ala |
| 225 | | | | | 230 | | | | | 235 | | | | | 240 |
| Glu | Asp | Gly | Ile | Thr | Cys | Lys | Ser | Ile | Ser | His | Thr | Val | Ser | Cys | Thr |
| | | | | 245 | | | | | 250 | | | | | 255 | |
| Ala | Glu | Gln | Lys | Gln | Thr | Cys | Arg | Pro | Thr | Glu | Asp | Cys | Arg | Val | His |
| | | | 260 | | | | | 265 | | | | | 270 | | |
| Lys | Gly | Thr | Val | Leu | Cys | Glu | Cys | Pro | Trp | Asn | Gln | His | Leu | Val | Gly |
| | | 275 | | | | | 280 | | | | | 285 | | | |
| Asp | Thr | Cys | Ile | Ser | Asp | Cys | Val | Asp | Lys | Lys | Cys | His | Glu | Glu | Phe |
| | 290 | | | | | 295 | | | | | 300 | | | | |
| Met | Asp | Cys | Gly | Val | Tyr | Met | Asn | Arg | Gln | Ser | Cys | Tyr | Cys | Pro | Trp |
| 305 | | | | | 310 | | | | | 315 | | | | | 320 |
| Lys | Ser | Arg | Lys | Pro | Gly | Pro | Asn | Val | Asn | Ile | Asn | Gly | Cys | Leu | Leu |
| | | | | 325 | | | | | 330 | | | | | 335 | |
| Asn | Glu | Tyr | Tyr | Tyr | Thr | Val | Ser | Phe | Thr | Pro | Asn | Ile | Ser | Phe | Asp |
| | | | 340 | | | | | 345 | | | | | 350 | | |
| Ser | Asp | His | Cys | Lys | Trp | Tyr | Glu | Asp | Arg | Val | Leu | Glu | Ala | Ile | Arg |
| | | 355 | | | | | 360 | | | | | 365 | | | |
| Thr | Ser | Ile | Gly | Lys | Glu | Val | Phe | Lys | Val | Glu | Ile | Leu | Asn | Cys | Thr |
| 370 | | | | | 375 | | | | | 380 | | | | | |

```
Gln  Asp  Ile  Lys  Ala  Arg  Leu  Ile  Ala  Glu  Lys  Pro  Leu  Ser  Asn  His
385                 390                 395                           400

Val  Leu  Arg  Lys  Leu  Gln  Ala  Cys  Glu  His  Pro  Ile  Gly  Glu  Trp  Cys
                    405                 410                      415

Met  Met  Tyr  Pro  Lys  Leu  Leu  Ile  Lys  Lys  Asn  Ser  Ala  Thr  Glu  Ile
               420                      425                      430

Glu  Glu  Glu  Asn  Leu  Cys  Asp  Ser  Leu  Leu  Lys  Asn  Gln  Glu  Ala  Ala
          435                 440                      445

Tyr  Lys  Gly  Gln  Asn  Lys  Cys  Val  Lys  Val  Asp  Asn  Leu  Phe  Trp  Phe
     450                     455                 460

Gln  Cys  Ala  Asp  Gly  Tyr  Thr  Thr  Thr  Tyr  Glu  Met  Thr  Arg  Gly  Arg
465                      470                 475                           480

Leu  Arg  Arg  Ser  Val  Cys  Lys  Ala  Gly  Val  Ser  Cys  Asn  Glu  Asn  Glu
                    485                      490                      495

Gln  Leu  Glu  Cys  Ala  Asp  Lys  Gly  Gln  Ile  Cys  Val  Tyr  Glu  Asn  Gly
               500                      505                 510

Lys  Ala  Asn  Cys  Gln  Cys  Pro  Pro  Asp  Thr  Lys  Pro  Gly  Glu  Ile  Gly
          515                     520                      525

Cys  Ile  Glu  Arg  Thr  Thr  Cys  Asn  Pro  Lys  Glu  Ile  Gln  Glu  Cys  Gln
530                           535                      540

Asp  Lys  Lys  Leu  Glu  Cys  Val  Tyr  Lys  Asn  His  Lys  Ala  Glu  Cys  Lys
545                      550                 555                           560

Cys  Pro  Asp  Asp  His  Glu  Cys  Ser  Arg  Glu  Pro  Ala  Lys  Asp  Ser  Cys
               565                      570                      575

Ser  Glu  Glu  Asp  Asn  Gly  Lys  Cys  Gln  Ser  Ser  Gly  Gln  Arg  Cys  Val
               580                      585                 590

Ile  Glu  Asn  Gly  Lys  Ala  Val  Cys  Lys  Glu  Lys  Ser  Glu  Ala  Thr  Thr
          595                      600                 605

Ala  Ala  Thr  Thr  Thr  Thr  Lys  Ala  Lys  Asp  Lys  Asp  Pro  Asp  Pro  Gly
          610                     615                 620

Lys  Ser  Ser  Ala  Ala  Ala  Val  Ser  Ala  Thr  Gly  Leu  Leu  Leu  Leu  Leu
625                      630                 635                           640

Ala  Ala  Thr  Ser  Val  Thr  Ala  Ala  Ser  Leu
               645                      650
```

( 2 ) INFORMATION FOR SEQ ID NO:64:

( i ) SEQUENCE CHARACTERISTICS:
        ( A ) LENGTH: 2131 base pairs
        ( B ) TYPE: nucleic acid
        ( C ) STRANDEDNESS: double
        ( D ) TOPOLOGY: linear ( v i i ) IMMEDIATE SOURCE:
        ( B ) CLONE: Figure 15

( i x ) FEATURE:
        ( A ) NAME/KEY: CDS
        ( B ) LOCATION: 1..1863

( x i ) SEQUENCE DESCRIPTION: SEQ ID NO:64:

```
TTC  TGT  CGC  AAC  GCT  GAA  TGC  GAA  GAG  GTG  CCT  GGT  GCC  GAG  GAT  GAT    48
Phe  Cys  Arg  Asn  Ala  Glu  Cys  Glu  Glu  Val  Pro  Gly  Ala  Glu  Asp  Asp
 1                  5                    10                       15

TTC  GTG  TGC  AAA  TGT  CCG  CGA  TAT  AAT  ATG  TAC  TTC  AAT  GCT  GCT  GAA    96
Phe  Val  Cys  Lys  Cys  Pro  Arg  Tyr  Asn  Met  Tyr  Phe  Asn  Ala  Ala  Glu
               20                   25                       30

AAA  CAA  TGC  GAA  TAT  AAA  GAT  ACG  TGC  AAG  ACA  AGA  GAG  TGC  AGC  TAT   144
Lys  Gln  Cys  Glu  Tyr  Lys  Asp  Thr  Cys  Lys  Thr  Arg  Glu  Cys  Ser  Tyr
```

|  | 35 | | | | 40 | | | | | 45 | | | | |
|---|---|---|---|---|---|---|---|---|---|---|---|---|---|---|
| GGC | CGT | TGC | GTT | CAA | AGT | AAC | CCG | AGC | AAG | GCT | AGC | TGT | GTC | TGC | GAA | 192 |
| Gly | Arg | Cys | Val | Gln | Ser | Asn | Pro | Ser | Lys | Ala | Ser | Cys | Val | Cys | Glu | |
| | 50 | | | | 55 | | | | | 60 | | | | | | |
| GCA | TCT | GAC | ACT | CTA | ACG | CTA | CAA | TGC | AAC | ATT | AAC | AAT | GAC | TAC | GCA | 240 |
| Ala | Ser | Asp | Thr | Leu | Thr | Leu | Gln | Cys | Asn | Ile | Asn | Asn | Asp | Tyr | Ala | |
| 65 | | | | | 70 | | | | | 75 | | | | | 80 | |
| ACT | GAC | TGC | CGA | AAC | AGG | GGT | GGT | ACC | GCT | AAG | TTG | CGC | ACG | GAT | GGG | 288 |
| Thr | Asp | Cys | Arg | Asn | Arg | Gly | Gly | Thr | Ala | Lys | Leu | Arg | Thr | Asp | Gly | |
| | | | | 85 | | | | | 90 | | | | | 95 | | |
| TTT | ATT | GGC | GCA | ACG | TGT | GAC | TGT | GGT | GAA | TGG | GGC | GCA | ATG | AAC | AAA | 336 |
| Phe | Ile | Gly | Ala | Thr | Cys | Asp | Cys | Gly | Glu | Trp | Gly | Ala | Met | Asn | Lys | |
| | | | 100 | | | | | 105 | | | | | 110 | | | |
| ACC | ACC | CGG | AAC | TGT | GTC | CCT | ACC | ACG | TGT | CTT | CGT | CCC | GAC | TTG | ACC | 384 |
| Thr | Thr | Arg | Asn | Cys | Val | Pro | Thr | Thr | Cys | Leu | Arg | Pro | Asp | Leu | Thr | |
| | | 115 | | | | | 120 | | | | | 125 | | | | |
| TGC | AAA | GAC | CTC | TGC | GAG | AAA | AAC | CTG | CTT | CAA | AGG | GAT | TCT | CGT | TGT | 432 |
| Cys | Lys | Asp | Leu | Cys | Glu | Lys | Asn | Leu | Leu | Gln | Arg | Asp | Ser | Arg | Cys | |
| | 130 | | | | | 135 | | | | | 140 | | | | | |
| TGC | CAG | GGG | TGG | AAC | ACA | GCA | AAC | TGT | TTA | GCC | GCT | CCT | CCA | GCT | GAC | 480 |
| Cys | Gln | Gly | Trp | Asn | Thr | Ala | Asn | Cys | Leu | Ala | Ala | Pro | Pro | Ala | Asp | |
| 145 | | | | | 150 | | | | | 155 | | | | | 160 | |
| TCC | TAT | TGC | TCT | CCT | GGG | AGC | CCC | AAA | GGA | CCG | GAC | GGA | CAG | TGT | AAA | 528 |
| Ser | Tyr | Cys | Ser | Pro | Gly | Ser | Pro | Lys | Gly | Pro | Asp | Gly | Gln | Cys | Lys | |
| | | | | 165 | | | | | 170 | | | | | 175 | | |
| AAT | GCT | TGC | AGG | ACG | AAA | GAA | GCT | GGG | TTT | GTC | TGC | AAG | CAT | GGA | TGC | 576 |
| Asn | Ala | Cys | Arg | Thr | Lys | Glu | Ala | Gly | Phe | Val | Cys | Lys | His | Gly | Cys | |
| | | | 180 | | | | | 185 | | | | | 190 | | | |
| AGG | TCC | ACC | GAC | AAG | GCG | TAC | GAG | TGC | ACG | TGC | CCG | AGT | GGC | TCT | ACC | 624 |
| Arg | Ser | Thr | Asp | Lys | Ala | Tyr | Glu | Cys | Thr | Cys | Pro | Ser | Gly | Ser | Thr | |
| | | 195 | | | | | 200 | | | | | 205 | | | | |
| GTC | GCC | GAA | GAT | GGC | ATT | ACC | TGC | AAA | AGT | ATT | TCG | TAC | ACA | GTC | AGC | 672 |
| Val | Ala | Glu | Asp | Gly | Ile | Thr | Cys | Lys | Ser | Ile | Ser | Tyr | Thr | Val | Ser | |
| | 210 | | | | | 215 | | | | | 220 | | | | | |
| TGC | ACT | GTT | GAG | CAA | AAA | CAG | ACC | TGC | CGC | CCA | ACC | GAA | GAC | TGT | CGT | 720 |
| Cys | Thr | Val | Glu | Gln | Lys | Gln | Thr | Cys | Arg | Pro | Thr | Glu | Asp | Cys | Arg | |
| 225 | | | | | 230 | | | | | 235 | | | | | 240 | |
| GTG | CAG | AAA | GGA | ACT | GTG | TTG | TGT | GAG | TGC | CCG | TGG | AAT | CAA | CAT | CTA | 768 |
| Val | Gln | Lys | Gly | Thr | Val | Leu | Cys | Glu | Cys | Pro | Trp | Asn | Gln | His | Leu | |
| | | | | 245 | | | | | 250 | | | | | 255 | | |
| GTG | GGG | GAC | AAG | TGC | ATA | AGT | GAT | TGC | GTC | GAC | AAG | AAA | TGT | CAC | GAA | 816 |
| Val | Gly | Asp | Lys | Cys | Ile | Ser | Asp | Cys | Val | Asp | Lys | Lys | Cys | His | Glu | |
| | | | 260 | | | | | 265 | | | | | 270 | | | |
| GAA | TTT | ATG | GAC | TGT | GGC | GTA | TAT | ATG | AAT | CGA | CAA | AGC | TGC | TAT | TGT | 864 |
| Glu | Phe | Met | Asp | Cys | Gly | Val | Tyr | Met | Asn | Arg | Gln | Ser | Cys | Tyr | Cys | |
| | | 275 | | | | | 280 | | | | | 285 | | | | |
| CCA | TGG | AAA | TCA | AGG | AAG | CCG | GGC | CCA | AAT | GTC | AAC | ATC | AAT | GAA | TGC | 912 |
| Pro | Trp | Lys | Ser | Arg | Lys | Pro | Gly | Pro | Asn | Val | Asn | Ile | Asn | Glu | Cys | |
| | 290 | | | | | 295 | | | | | 300 | | | | | |
| CTA | CTG | AAT | GAG | TAT | TAC | TAC | ACG | GTG | TCA | TTC | ACC | CCG | AAC | ATA | TCT | 960 |
| Leu | Leu | Asn | Glu | Tyr | Tyr | Tyr | Thr | Val | Ser | Phe | Thr | Pro | Asn | Ile | Ser | |
| 305 | | | | | 310 | | | | | 315 | | | | | 320 | |
| TTT | GAT | TCT | GAC | CAT | TGC | AAA | CGG | TAT | GAG | GAT | CGT | GTT | TTG | GAA | GCG | 1008 |
| Phe | Asp | Ser | Asp | His | Cys | Lys | Arg | Tyr | Glu | Asp | Arg | Val | Leu | Glu | Ala | |
| | | | | 325 | | | | | 330 | | | | | 335 | | |
| ATA | CGG | ACC | AGT | ATC | GGA | AAA | GAA | GTT | TTT | AAG | GTT | GAG | ATA | CTT | AAC | 1056 |
| Ile | Arg | Thr | Ser | Ile | Gly | Lys | Glu | Val | Phe | Lys | Val | Glu | Ile | Leu | Asn | |
| | | | 340 | | | | | 345 | | | | | 350 | | | |
| TGC | ACG | CAG | GAC | ATT | AAG | GCA | AGA | CTC | ATA | GCA | GAG | AAA | CCA | CTG | TCA | 1104 |
| Cys | Thr | Gln | Asp | Ile | Lys | Ala | Arg | Leu | Ile | Ala | Glu | Lys | Pro | Leu | Ser | |

-continued

|  |  |  | 355 |  |  |  |  | 360 |  |  |  |  | 365 |  |  |  |
|---|---|---|---|---|---|---|---|---|---|---|---|---|---|---|---|---|
| AAA | TAC | GTG | CTC | AGG | AAA | CTA | CAA | GCA | TGC | GAG | CAT | CCA | ATC | GGC | GAA | 1152 |
| Lys | Tyr | Val | Leu | Arg | Lys | Leu | Gln | Ala | Cys | Glu | His | Pro | Ile | Gly | Glu |  |
|  | 370 |  |  |  | 375 |  |  |  |  | 380 |  |  |  |  |  |  |
| TGG | TGC | ATG | ATG | TAT | CCG | AAG | TTG | CTG | ATC | AAG | AAA | AAC | TCT | GCA | ACA | 1200 |
| Trp | Cys | Met | Met | Tyr | Pro | Lys | Leu | Leu | Ile | Lys | Lys | Asn | Ser | Ala | Thr |  |
| 385 |  |  |  |  | 390 |  |  |  |  | 395 |  |  |  |  | 400 |  |
| GAA | ATT | GAA | GAA | GAG | AAC | CTT | TGC | GAC | AGT | CTG | CTC | AAG | AAT | CAG | GAA | 1248 |
| Glu | Ile | Glu | Glu | Glu | Asn | Leu | Cys | Asp | Ser | Leu | Leu | Lys | Asn | Gln | Glu |  |
|  |  |  |  | 405 |  |  |  |  | 410 |  |  |  |  | 415 |  |  |
| GCT | GCC | TAC | AAA | GGT | CAA | AAC | AAA | TGC | GTC | AAG | GTC | GAC | AAC | CTC | TTC | 1296 |
| Ala | Ala | Tyr | Lys | Gly | Gln | Asn | Lys | Cys | Val | Lys | Val | Asp | Asn | Leu | Phe |  |
|  |  |  | 420 |  |  |  |  | 425 |  |  |  |  | 430 |  |  |  |
| TGG | TTC | CAG | TGC | GCT | GAT | GGT | TAC | ACA | ACA | ACT | TAC | GAG | ATG | ACA | CGA | 1344 |
| Trp | Phe | Gln | Cys | Ala | Asp | Gly | Tyr | Thr | Thr | Thr | Tyr | Glu | Met | Thr | Arg |  |
|  |  | 435 |  |  |  |  | 440 |  |  |  |  | 445 |  |  |  |  |
| GGT | CGC | CTA | CGC | CGC | TCC | GTG | TGT | AAA | GCT | GGA | GTT | TCT | TGC | AAC | GAA | 1392 |
| Gly | Arg | Leu | Arg | Arg | Ser | Val | Cys | Lys | Ala | Gly | Val | Ser | Cys | Asn | Glu |  |
|  | 450 |  |  |  |  | 455 |  |  |  |  | 460 |  |  |  |  |  |
| AAC | GAG | CAG | TTG | GAG | TGT | GCT | AAC | AAA | GGT | CAA | ATA | TGT | GTC | TAC | GAA | 1440 |
| Asn | Glu | Gln | Leu | Glu | Cys | Ala | Asn | Lys | Gly | Gln | Ile | Cys | Val | Tyr | Glu |  |
| 465 |  |  |  |  | 470 |  |  |  |  | 475 |  |  |  |  | 480 |  |
| AAC | GGC | AAA | GCG | AAT | TGC | CAA | TGC | CCA | CCA | GAC | ACT | AAA | CCA | GGG | GAG | 1488 |
| Asn | Gly | Lys | Ala | Asn | Cys | Gln | Cys | Pro | Pro | Asp | Thr | Lys | Pro | Gly | Glu |  |
|  |  |  |  | 485 |  |  |  |  | 490 |  |  |  |  | 495 |  |  |
| ATT | GGC | TGC | ATT | GAG | CGT | ACC | ACA | TGC | AAC | CCT | AAA | GAG | ATA | CAA | GAA | 1536 |
| Ile | Gly | Cys | Ile | Glu | Arg | Thr | Thr | Cys | Asn | Pro | Lys | Glu | Ile | Gln | Glu |  |
|  |  |  | 500 |  |  |  |  | 505 |  |  |  |  | 510 |  |  |  |
| TGC | CAA | GAC | AAG | AAG | CTC | GAG | TGC | GTT | TAC | AAA | AAC | CAT | AAA | GCA | GAA | 1584 |
| Cys | Gln | Asp | Lys | Lys | Leu | Glu | Cys | Val | Tyr | Lys | Asn | His | Lys | Ala | Glu |  |
|  |  | 515 |  |  |  |  | 520 |  |  |  |  | 525 |  |  |  |  |
| TSS | AAG | TGT | CCT | GAT | GAT | CAC | GAG | TGT | TCT | AGG | GAG | CCT | GCC | AAA | GAC | 1632 |
| Xaa | Lys | Cys | Pro | Asp | Asp | His | Glu | Cys | Ser | Arg | Glu | Pro | Ala | Lys | Asp |  |
|  | 530 |  |  |  |  | 535 |  |  |  |  | 540 |  |  |  |  |  |
| TCT | TGC | AGT | GAA | GAA | GAT | AAT | GGT | AAA | TGT | CAA | AGC | AGT | GGG | CAG | CGT | 1680 |
| Ser | Cys | Ser | Glu | Glu | Asp | Asn | Gly | Lys | Cys | Gln | Ser | Ser | Gly | Gln | Arg |  |
| 545 |  |  |  |  | 550 |  |  |  |  | 555 |  |  |  |  | 560 |  |
| TGT | GTA | ATG | GAA | AAC | GGA | AAT | GCT | GTT | TGC | AAA | GAG | AAG | TCT | GAT | GCA | 1728 |
| Cys | Val | Met | Glu | Asn | Gly | Asn | Ala | Val | Cys | Lys | Glu | Lys | Ser | Asp | Ala |  |
|  |  |  |  | 565 |  |  |  |  | 570 |  |  |  |  | 575 |  |  |
| ACA | ACA | GCT | TCG | ACT | ACA | ACA | ACG | AAA | GCG | AAA | GAC | AAG | GAT | CCA | GAT | 1776 |
| Thr | Thr | Ala | Ser | Thr | Thr | Thr | Thr | Lys | Ala | Lys | Asp | Lys | Asp | Pro | Asp |  |
|  |  |  | 580 |  |  |  |  | 585 |  |  |  |  | 590 |  |  |  |
| CCT | GAA | AAG | TCA | AGT | GCT | GCA | GCA | GTA | TCA | GCT | ACT | GGG | CTC | TTG | TTA | 1824 |
| Pro | Glu | Lys | Ser | Ser | Ala | Ala | Ala | Val | Ser | Ala | Thr | Gly | Leu | Leu | Leu |  |
|  |  | 595 |  |  |  |  | 600 |  |  |  |  | 605 |  |  |  |  |
| CTG | CTC | GCA | GCT | ACT | TCA | GTC | ACC | GCA | GCA | TCG | TTG | TAATGAAGAT |  |  |  | 1870 |
| Leu | Leu | Ala | Ala | Thr | Ser | Val | Thr | Ala | Ala | Ser | Leu |  |  |  |  |  |
|  | 610 |  |  |  |  | 615 |  |  |  |  | 620 |  |  |  |  |  |

```
GTCCAACTTG AATACGGAAC AGCTTGAAAA TGTATATATA CATCACGCTT ACATCGAACA   1930

TCTAGCTTGG TCTTTGGAAT TTAAATATTG CACATGGGTA CTCACGGCAA AATGGACGTA   1990

TTATTTTAGA ATGACAGGGA AGATGGACGT GAAAGGAGTT TCCTTGTCTG AAAATATCAA   2050

AGAAAAACTT TCCCTATCTG AATGATGTCA AATAAAGATA GTTGGGTCTA AACAAAAAAA   2110

AAAAAAAAAA AAAAGCGGCC G                                             2131
```

( 2 ) INFORMATION FOR SEQ ID NO:65:

( i ) SEQUENCE CHARACTERISTICS:

( A ) LENGTH: 620 amino acids
( B ) TYPE: amino acid
( D ) TOPOLOGY: linear ( i i ) MOLECULE TYPE: protein ( x i ) SEQUENCE DESCRIPTION: SEQ ID NO:65:

| Phe | Cys | Arg | Asn | Ala | Glu | Cys | Glu | Glu | Val | Pro | Gly | Ala | Glu | Asp | Asp |
|---|---|---|---|---|---|---|---|---|---|---|---|---|---|---|---|
| 1 | | | | 5 | | | | | 10 | | | | | 15 | |
| Phe | Val | Cys | Lys | Cys | Pro | Arg | Tyr | Asn | Met | Tyr | Phe | Asn | Ala | Ala | Glu |
| | | | 20 | | | | | 25 | | | | | 30 | | |
| Lys | Gln | Cys | Glu | Tyr | Lys | Asp | Thr | Cys | Lys | Thr | Arg | Glu | Cys | Ser | Tyr |
| | | 35 | | | | | 40 | | | | | 45 | | | |
| Gly | Arg | Cys | Val | Gln | Ser | Asn | Pro | Ser | Lys | Ala | Ser | Cys | Val | Cys | Glu |
| | 50 | | | | | 55 | | | | | 60 | | | | |
| Ala | Ser | Asp | Thr | Leu | Thr | Leu | Gln | Cys | Asn | Ile | Asn | Asn | Asp | Tyr | Ala |
| 65 | | | | | 70 | | | | 75 | | | | | 80 | |
| Thr | Asp | Cys | Arg | Asn | Arg | Gly | Gly | Thr | Ala | Lys | Leu | Arg | Thr | Asp | Gly |
| | | | | 85 | | | | 90 | | | | | | 95 | |
| Phe | Ile | Gly | Ala | Thr | Cys | Asp | Cys | Gly | Glu | Trp | Gly | Ala | Met | Asn | Lys |
| | | | 100 | | | | | 105 | | | | | 110 | | |
| Thr | Thr | Arg | Asn | Cys | Val | Pro | Thr | Thr | Cys | Leu | Arg | Pro | Asp | Leu | Thr |
| | | 115 | | | | | 120 | | | | | 125 | | | |
| Cys | Lys | Asp | Leu | Cys | Glu | Lys | Asn | Leu | Leu | Gln | Arg | Asp | Ser | Arg | Cys |
| | 130 | | | | | 135 | | | | | 140 | | | | |
| Cys | Gln | Gly | Trp | Asn | Thr | Ala | Asn | Cys | Leu | Ala | Ala | Pro | Pro | Ala | Asp |
| 145 | | | | | 150 | | | | | 155 | | | | | 160 |
| Ser | Tyr | Cys | Ser | Pro | Gly | Ser | Pro | Lys | Gly | Pro | Asp | Gly | Gln | Cys | Lys |
| | | | | 165 | | | | | 170 | | | | | 175 | |
| Asn | Ala | Cys | Arg | Thr | Lys | Glu | Ala | Gly | Phe | Val | Cys | Lys | His | Gly | Cys |
| | | | 180 | | | | | 185 | | | | | 190 | | |
| Arg | Ser | Thr | Asp | Lys | Ala | Tyr | Glu | Cys | Thr | Cys | Pro | Ser | Gly | Ser | Thr |
| | | 195 | | | | | 200 | | | | | 205 | | | |
| Val | Ala | Glu | Asp | Gly | Ile | Thr | Cys | Lys | Ser | Ile | Ser | Tyr | Thr | Val | Ser |
| | 210 | | | | | 215 | | | | | 220 | | | | |
| Cys | Thr | Val | Glu | Gln | Lys | Gln | Thr | Cys | Arg | Pro | Thr | Glu | Asp | Cys | Arg |
| 225 | | | | | 230 | | | | | 235 | | | | | 240 |
| Val | Gln | Lys | Gly | Thr | Val | Leu | Cys | Glu | Cys | Pro | Trp | Asn | Gln | His | Leu |
| | | | | 245 | | | | | 250 | | | | | 255 | |
| Val | Gly | Asp | Lys | Cys | Ile | Ser | Asp | Cys | Val | Asp | Lys | Lys | Cys | His | Glu |
| | | | 260 | | | | | 265 | | | | | 270 | | |
| Glu | Phe | Met | Asp | Cys | Gly | Val | Tyr | Met | Asn | Arg | Gln | Ser | Cys | Tyr | Cys |
| | | 275 | | | | | 280 | | | | | 285 | | | |
| Pro | Trp | Lys | Ser | Arg | Lys | Pro | Gly | Pro | Asn | Val | Asn | Ile | Asn | Glu | Cys |
| | 290 | | | | | 295 | | | | | 300 | | | | |
| Leu | Leu | Asn | Glu | Tyr | Tyr | Tyr | Thr | Val | Ser | Phe | Thr | Pro | Asn | Ile | Ser |
| 305 | | | | | 310 | | | | | 315 | | | | | 320 |
| Phe | Asp | Ser | Asp | His | Cys | Lys | Arg | Tyr | Glu | Asp | Arg | Val | Leu | Glu | Ala |
| | | | | 325 | | | | | 330 | | | | | 335 | |
| Ile | Arg | Thr | Ser | Ile | Gly | Lys | Glu | Val | Phe | Lys | Val | Glu | Ile | Leu | Asn |
| | | | 340 | | | | | 345 | | | | | 350 | | |
| Cys | Thr | Gln | Asp | Ile | Lys | Ala | Arg | Leu | Ile | Ala | Glu | Lys | Pro | Leu | Ser |
| | | 355 | | | | | 360 | | | | | 365 | | | |
| Lys | Tyr | Val | Leu | Arg | Lys | Leu | Gln | Ala | Cys | Glu | His | Pro | Ile | Gly | Glu |
| | 370 | | | | | 375 | | | | | 380 | | | | |

| | | | | | | | | | | | | | | | |
|---|---|---|---|---|---|---|---|---|---|---|---|---|---|---|---|
| Trp<br>385 | Cys | Met | Met | Tyr | Pro<br>390 | Lys | Leu | Leu | Ile | Lys<br>395 | Lys | Asn | Ser | Ala | Thr<br>400 |
| Glu | Ile | Glu | Glu | Glu<br>405 | Asn | Leu | Cys | Asp | Ser<br>410 | Leu | Leu | Lys | Asn | Gln<br>415 | Glu |
| Ala | Ala | Tyr | Lys<br>420 | Gly | Gln | Asn | Lys | Cys<br>425 | Val | Lys | Val | Asp | Asn<br>430 | Leu | Phe |
| Trp | Phe | Gln<br>435 | Cys | Ala | Asp | Gly | Tyr<br>440 | Thr | Thr | Thr | Tyr | Glu<br>445 | Met | Thr | Arg |
| Gly | Arg<br>450 | Leu | Arg | Arg | Ser | Val<br>455 | Cys | Lys | Ala | Gly | Val<br>460 | Ser | Cys | Asn | Glu |
| Asn<br>465 | Glu | Gln | Leu | Glu | Cys<br>470 | Ala | Asn | Lys | Gly | Gln<br>475 | Ile | Cys | Val | Tyr | Glu<br>480 |
| Asn | Gly | Lys | Ala | Asn<br>485 | Cys | Gln | Cys | Pro | Pro<br>490 | Asp | Thr | Lys | Pro | Gly<br>495 | Glu |
| Ile | Gly | Cys | Ile<br>500 | Glu | Arg | Thr | Thr | Cys<br>505 | Asn | Pro | Lys | Glu | Ile<br>510 | Gln | Glu |
| Cys | Gln | Asp<br>515 | Lys | Lys | Leu | Glu | Cys<br>520 | Val | Tyr | Lys | Asn | His<br>525 | Lys | Ala | Glu |
| Xaa | Lys<br>530 | Cys | Pro | Asp | Asp | His<br>535 | Glu | Cys | Ser | Arg | Glu<br>540 | Pro | Ala | Lys | Asp |
| Ser<br>545 | Cys | Ser | Glu | Glu | Asp<br>550 | Asn | Gly | Lys | Cys | Gln<br>555 | Ser | Ser | Gly | Gln | Arg<br>560 |
| Cys | Val | Met | Glu | Asn<br>565 | Gly | Asn | Ala | Val | Cys<br>570 | Lys | Glu | Lys | Ser | Asp<br>575 | Ala |
| Thr | Thr | Ala | Ser<br>580 | Thr | Thr | Thr | Thr | Lys<br>585 | Ala | Lys | Asp | Lys | Asp<br>590 | Pro | Asp |
| Pro | Glu | Lys<br>595 | Ser | Ser | Ala | Ala | Ala<br>600 | Val | Ser | Ala | Thr | Gly<br>605 | Leu | Leu | Leu |
| Leu | Leu<br>610 | Ala | Ala | Thr | Ser | Val<br>615 | Thr | Ala | Ala | Ser | Leu<br>620 | | | | |

( 2 ) INFORMATION FOR SEQ ID NO:66:

( i ) SEQUENCE CHARACTERISTICS:
        ( A ) LENGTH: 2147 base pairs
        ( B ) TYPE: nucleic acid
        ( C ) STRANDEDNESS: double
        ( D ) TOPOLOGY: linear ( v i i ) IMMEDIATE SOURCE:
        ( B ) CLONE: Figure 16

( i x ) FEATURE:
        ( A ) NAME/KEY: CDS
        ( B ) LOCATION: 49..2001

( x i ) SEQUENCE DESCRIPTION: SEQ ID NO:66:

| | | | | | | |
|---|---|---|---|---|---|---|
| CAGGATCCGT | GGAAAGTGCG | ACAGCTGCGG | TGGTTCGACG | CAGTCGAG | ATG CGT GGC<br>Met Arg Gly<br>1 | 57 |
| ATC GCT TTG TTC GTC GCC GCT GTT TCA CTG ATT GTA GAG TGC ACA GCA<br>Ile Ala Leu Phe Val Ala Ala Val Ser Leu Ile Val Glu Cys Thr Ala<br>     5                      10                      15 | | | | | | 105 |
| GAA TCA TCC ATT TGC TCT GAC TTC GGG AAC GAG TTC TGT CGC AAC GCT<br>Glu Ser Ser Ile Cys Ser Asp Phe Gly Asn Glu Phe Cys Arg Asn Ala<br>20                      25                      30                      35 | | | | | | 153 |
| GAA TGT GAA GTG GTG CCT GGT GCA GAG GAT GAT TTC GTG TGC AAA TGT<br>Glu Cys Glu Val Val Pro Gly Ala Glu Asp Asp Phe Val Cys Lys Cys<br>                    40                            45                      50 | | | | | | 201 |
| CCG CGA GAT AAT ATG TAC TTC AAT GCT GCT GAA AAG CAA TGC GAA TAT | | | | | | 249 |

|     |     |     |     |     |     |     |     |     |     |     |     |     |     |     |     |
|---|---|---|---|---|---|---|---|---|---|---|---|---|---|---|---|
| Pro | Arg | Asp | Asn | Met | Tyr | Phe | Asn | Ala | Ala | Glu | Lys | Gln | Cys | Glu | Tyr |
|     |     |     | 55  |     |     |     |     | 60  |     |     |     | 65  |     |     |     |

```
AAA GAT ACG TGC AAG ACA AGG GAG TGC AGC TAT GGA CGT TGC GTT GAA      297
Lys Asp Thr Cys Lys Thr Arg Glu Cys Ser Tyr Gly Arg Cys Val Glu
        70              75                  80

AGT AAC CCG AGC AAG GGT AGC TGC GTC TGC GAA GCA TCG GAC GAT CTA      345
Ser Asn Pro Ser Lys Gly Ser Cys Val Cys Glu Ala Ser Asp Asp Leu
        85              90                  95

ACG CTA CAA TGC AAA ATT AAA AAT GAC TTC GCA ACT GAC TGC CGA AAC      393
Thr Leu Gln Cys Lys Ile Lys Asn Asp Phe Ala Thr Asp Cys Arg Asn
100             105             110                 115

CGA GGT GGC ACT GCT AAG TTG CGC ACG GAT GGG TTT ATT GGC CCA ACG      441
Arg Gly Gly Thr Ala Lys Leu Arg Thr Asp Gly Phe Ile Gly Pro Thr
                120             125                 130

TGT GAC TGT GGT GAA TGG GGT GCG ATG AAC AAG ACC ACA CGG AAC TGT      489
Cys Asp Cys Gly Glu Trp Gly Ala Met Asn Lys Thr Thr Arg Asn Cys
            135             140                 145

GTC CCT ACC ACG TGT CTT CGT CCC GAC TTG ACC TGC AAA GAC CTC TGC      537
Val Pro Thr Thr Cys Leu Arg Pro Asp Leu Thr Cys Lys Asp Leu Cys
        150             155                 160

GAG AAA AAC CTG CTT CAA AGG GAT TCT CGT TGT TGT CAG GGG TGG AAC      585
Glu Lys Asn Leu Leu Gln Arg Asp Ser Arg Cys Cys Gln Gly Trp Asn
165             170                 175

ACA GCA AAC TGT TCA GCC GCT CCT CCA GCT GAC TCC TAT TGC TCT CCT      633
Thr Ala Asn Cys Ser Ala Ala Pro Pro Ala Asp Ser Tyr Cys Ser Pro
180             185                 190                 195

GGG AGC CCC AAA GGA CCG GAC GGA CAG TGT AAA AAT GCT TGC AGG ACG      681
Gly Ser Pro Lys Gly Pro Asp Gly Gln Cys Lys Asn Ala Cys Arg Thr
                200             205                 210

AAA GAA GCT GGG TTT GTC TGC AAG CAT GGA TGC AGG TCC ACC GAC AAG      729
Lys Glu Ala Gly Phe Val Cys Lys His Gly Cys Arg Ser Thr Asp Lys
            215             220                 225

GCG TAC GAG TGC ACG TGC CCG AGT GGC TCT ACC GTC GCC GAA GAT GGC      777
Ala Tyr Glu Cys Thr Cys Pro Ser Gly Ser Thr Val Ala Glu Asp Gly
        230             235                 240

ATT ACC TGC AAA AGT ATT TCG TAC ACA GTC AGC TGC ACT GTT GAG CAA      825
Ile Thr Cys Lys Ser Ile Ser Tyr Thr Val Ser Cys Thr Val Glu Gln
        245             250                 255

AAA CAG ACC TGC CGC CCA ACC GAA GAC TGT CGT GTG CAG AAA GGA ACT      873
Lys Gln Thr Cys Arg Pro Thr Glu Asp Cys Arg Val Gln Lys Gly Thr
260             265                 270                 275

GTG TTG TGT GAG TGC CCG TGG AAT CAA CAT CTA GTG GGG GAC ACG TGC      921
Val Leu Cys Glu Cys Pro Trp Asn Gln His Leu Val Gly Asp Thr Cys
            280             285                 290

ATA AGT GAT TGC GTC GAC AAG AAA TGT CAC GAA GAA TTT ATG GAC TGT      969
Ile Ser Asp Cys Val Asp Lys Lys Cys His Glu Glu Phe Met Asp Cys
            295             300                 305

GGC GTA TAT ATG AAT CGA CAA AGC TGC TAT TGT CCA TGG AAA TCA AGG     1017
Gly Val Tyr Met Asn Arg Gln Ser Cys Tyr Cys Pro Trp Lys Ser Arg
        310             315                 320

AAG CCG GGC CCA AAT GTC AAC ATC AAT GAA TGC CTA CTG AAT GAG TAT     1065
Lys Pro Gly Pro Asn Val Asn Ile Asn Glu Cys Leu Leu Asn Glu Tyr
325             330                 335

TAC TAC ACG GTG TCA TTC ACC CCG AAC ATA TCT TTT GAT TCT GAC CAT     1113
Tyr Tyr Thr Val Ser Phe Thr Pro Asn Ile Ser Phe Asp Ser Asp His
340             345                 350                 355

TGC AAA CGG TAT GAG GAT CGT GTT TTG GAA GCG ATA CGG ACC AGT ATC     1161
Cys Lys Arg Tyr Glu Asp Arg Val Leu Glu Ala Ile Arg Thr Ser Ile
        360             365                 370

GGA AAA GAA GTT TTT AAG GTT GAG ATA CTT AAC TGC ACG CAG GAC ATT     1209
```

|  |  |  |  |  |  |  |  |  |  |  |  |  |  |  |  |
|---|---|---|---|---|---|---|---|---|---|---|---|---|---|---|---|
| Gly | Lys | Glu | Val<br>375 | Phe | Lys | Val | Glu | Ile<br>380 | Leu | Asn | Cys | Thr | Gln<br>385 | Asp | Ile |

| AAG | GCA | AGA | CTC | ATA | GCA | GAG | AAA | CCA | CTG | TCA | AAA | TAC | GTG | CTC | AGG | 1257 |
|---|---|---|---|---|---|---|---|---|---|---|---|---|---|---|---|---|
| Lys | Ala | Arg<br>390 | Leu | Ile | Ala | Glu | Lys<br>395 | Pro | Leu | Ser | Lys | Tyr<br>400 | Val | Leu | Arg | |

| AAA | CTA | CAA | GCA | TGC | GAG | CAT | CCA | ATC | GGC | GAA | TGG | TGC | ATG | ATG | TAT | 1305 |
|---|---|---|---|---|---|---|---|---|---|---|---|---|---|---|---|---|
| Lys | Leu<br>405 | Gln | Ala | Cys | Glu | His<br>410 | Pro | Ile | Gly | Glu | Trp<br>415 | Cys | Met | Met | Tyr | |

| CCG | AAG | TTG | CTG | ATC | AAG | AAA | AAC | TCT | GCA | ACA | GAA | ATT | GAA | GAA | GAG | 1353 |
|---|---|---|---|---|---|---|---|---|---|---|---|---|---|---|---|---|
| Pro<br>420 | Lys | Leu | Leu | Ile | Lys<br>425 | Lys | Asn | Ser | Ala | Thr<br>430 | Glu | Ile | Glu | Glu | Glu<br>435 | |

| AAC | CTT | TGC | GAC | AGT | CTG | CTC | AAG | AAT | CAG | GAA | GCT | GCC | TAC | AAA | GGT | 1401 |
|---|---|---|---|---|---|---|---|---|---|---|---|---|---|---|---|---|
| Asn | Leu | Cys | Asp | Ser<br>440 | Leu | Leu | Lys | Asn | Gln<br>445 | Glu | Ala | Ala | Tyr | Lys<br>450 | Gly | |

| CAA | AAC | AAA | TGC | GTC | AAG | GTC | GAC | AAC | CTC | TTC | TGG | TTC | CAG | TGC | GCT | 1449 |
|---|---|---|---|---|---|---|---|---|---|---|---|---|---|---|---|---|
| Gln | Asn | Lys | Cys<br>455 | Val | Lys | Val | Asp | Asn<br>460 | Leu | Phe | Trp | Phe | Gln<br>465 | Cys | Ala | |

| GAT | GGT | TAC | ACA | ACA | ACT | TAC | GAG | ATG | ACA | CGA | GGT | CGC | CTA | CGC | CGC | 1497 |
|---|---|---|---|---|---|---|---|---|---|---|---|---|---|---|---|---|
| Asp | Gly | Tyr<br>470 | Thr | Thr | Thr | Tyr | Glu<br>475 | Met | Thr | Arg | Gly | Arg<br>480 | Leu | Arg | Arg | |

| TCC | GTG | TGT | AAA | GCT | GGA | GTT | TCT | TGC | AAC | GAA | AAC | GAG | CAG | TTG | GAG | 1545 |
|---|---|---|---|---|---|---|---|---|---|---|---|---|---|---|---|---|
| Ser | Val | Cys<br>485 | Lys | Ala | Gly | Val<br>490 | Ser | Cys | Asn | Glu | Asn<br>495 | Glu | Gln | Leu | Glu | |

| TGT | GCT | AAC | AAA | GGT | CAA | ATA | TGT | GTC | TAC | GAA | AAC | GGC | AAA | GCG | AAT | 1593 |
|---|---|---|---|---|---|---|---|---|---|---|---|---|---|---|---|---|
| Cys<br>500 | Ala | Asn | Lys | Gly<br>505 | Gln | Ile | Cys | Val | Tyr<br>510 | Glu | Asn | Gly | Lys | Ala | Asn<br>515 | |

| TGC | CAA | TGC | CCA | CCA | GAC | ACT | AAA | CCA | GGG | GAG | ATT | GGC | TGC | ATT | GAG | 1641 |
|---|---|---|---|---|---|---|---|---|---|---|---|---|---|---|---|---|
| Cys | Gln | Cys | Pro | Pro<br>520 | Asp | Thr | Lys | Pro | Gly<br>525 | Glu | Ile | Gly | Cys | Ile<br>530 | Glu | |

| CGT | ACC | ACA | TGC | AAC | CCT | AAA | GAG | ATA | CAA | GAA | TGC | CAA | GAC | AAG | AAG | 1689 |
|---|---|---|---|---|---|---|---|---|---|---|---|---|---|---|---|---|
| Arg | Thr | Thr | Cys<br>535 | Asn | Pro | Lys | Glu | Ile<br>540 | Gln | Glu | Cys | Gln | Asp<br>545 | Lys | Lys | |

| CTC | GAG | TGC | GTT | TAC | AAA | AAC | CAT | AAA | GCA | GAA | TGC | AAG | TGT | CCT | GAT | 1737 |
|---|---|---|---|---|---|---|---|---|---|---|---|---|---|---|---|---|
| Leu | Glu | Cys<br>550 | Val | Tyr | Lys | Asn | His<br>555 | Lys | Ala | Glu | Cys | Lys<br>560 | Cys | Pro | Asp | |

| GAT | CAC | GAG | TGT | TCT | AGG | CAG | CCT | GCC | AAA | GAC | TCT | TGC | AGT | GAA | GAG | 1785 |
|---|---|---|---|---|---|---|---|---|---|---|---|---|---|---|---|---|
| Asp | His<br>565 | Glu | Cys | Ser | Arg | Gln<br>570 | Pro | Ala | Lys | Asp | Ser<br>575 | Cys | Ser | Glu | Glu | |

| GAT | AAT | GGT | AAA | TGT | CAA | AGC | AGT | GGG | CAG | CGT | TGT | GTA | ATG | GAA | AAC | 1833 |
|---|---|---|---|---|---|---|---|---|---|---|---|---|---|---|---|---|
| Asp | Asn<br>580 | Gly | Lys | Cys | Gln<br>585 | Ser | Ser | Gly | Gln | Arg<br>590 | Cys | Val | Met | Glu | Asn<br>595 | |

| GGA | AAG | GCT | GTT | TGC | AAA | GAG | AAG | TCT | GAA | GCA | ACA | ACA | GCT | GCG | ACT | 1881 |
|---|---|---|---|---|---|---|---|---|---|---|---|---|---|---|---|---|
| Gly | Lys | Ala | Val | Cys<br>600 | Lys | Glu | Lys | Ser | Glu<br>605 | Ala | Thr | Thr | Ala | Ala<br>610 | Thr | |

| ACA | ACA | ACG | AAA | GCG | AAA | GAC | AAG | GAT | CCA | GAT | CCT | GGA | AAG | TCA | AGT | 1929 |
|---|---|---|---|---|---|---|---|---|---|---|---|---|---|---|---|---|
| Thr | Thr | Thr | Lys<br>615 | Ala | Lys | Asp | Lys | Asp<br>620 | Pro | Asp | Pro | Gly | Lys<br>625 | Ser | Ser | |

| GCT | GCA | GCA | GTA | TCA | GCT | ACT | GGG | CTC | TTG | TTA | CTG | CTC | GCA | GCT | ACT | 1977 |
|---|---|---|---|---|---|---|---|---|---|---|---|---|---|---|---|---|
| Ala | Ala | Ala<br>630 | Val | Ser | Ala | Thr | Gly<br>635 | Leu | Leu | Leu | Leu | Leu<br>640 | Ala | Ala | Thr | |

| TCA | GTC | ACC | GTA | GCA | TCG | TTG | TAATGAAGAT | GTCCAACTTG | AATACGGAAC | 2028 |
|---|---|---|---|---|---|---|---|---|---|---|
| Ser | Val | Thr<br>645 | Val | Ala | Ser | Leu<br>650 | | | | |

AGCTTGAAAA TGTATATATA CATCGCGCTT ACATCGAACA CCTAGCTTGG TTTTTGGGAT    2088

TTCAATATTG CGCATGGGTA CTCACGTCAA CATGGGATGT ATTATTTGAG AATGACAAG    2147

( 2 ) INFORMATION FOR SEQ ID NO:67:

( i ) SEQUENCE CHARACTERISTICS:
        ( A ) LENGTH: 650 amino acids (B) TYPE: amino acid
(D) TOPOLOGY: linear (ii) MOLECULE TYPE: protein (xi) SEQUENCE DESCRIPTION: SEQ ID NO:67:

```
Met Arg Gly Ile Ala Leu Phe Val Ala Ala Val Ser Leu Ile Val Glu
 1               5                  10                  15
Cys Thr Ala Glu Ser Ser Ile Cys Ser Asp Phe Gly Asn Glu Phe Cys
                20                  25                  30
Arg Asn Ala Glu Cys Glu Val Val Pro Gly Ala Glu Asp Asp Phe Val
                35                  40                  45
Cys Lys Cys Pro Arg Asp Asn Met Tyr Phe Asn Ala Ala Glu Lys Gln
        50                  55                  60
Cys Glu Tyr Lys Asp Thr Cys Lys Thr Arg Glu Cys Ser Tyr Gly Arg
 65                  70                  75                  80
Cys Val Glu Ser Asn Pro Ser Lys Gly Ser Cys Val Cys Glu Ala Ser
                    85                  90                  95
Asp Asp Leu Thr Leu Gln Cys Lys Ile Lys Asn Asp Phe Ala Thr Asp
                100                 105                 110
Cys Arg Asn Arg Gly Gly Thr Ala Lys Leu Arg Thr Asp Gly Phe Ile
            115                 120                 125
Gly Pro Thr Cys Asp Cys Gly Glu Trp Gly Ala Met Asn Lys Thr Thr
    130                 135                 140
Arg Asn Cys Val Pro Thr Thr Cys Leu Arg Pro Asp Leu Thr Cys Lys
145                 150                 155                 160
Asp Leu Cys Glu Lys Asn Leu Leu Gln Arg Asp Ser Arg Cys Cys Gln
                165                 170                 175
Gly Trp Asn Thr Ala Asn Cys Ser Ala Ala Pro Pro Ala Asp Ser Tyr
            180                 185                 190
Cys Ser Pro Gly Ser Pro Lys Gly Pro Asp Gly Gln Cys Lys Asn Ala
    195                 200                 205
Cys Arg Thr Lys Glu Ala Gly Phe Val Cys Lys His Gly Cys Arg Ser
    210                 215                 220
Thr Asp Lys Ala Tyr Glu Cys Thr Cys Pro Ser Gly Ser Thr Val Ala
225                 230                 235                 240
Glu Asp Gly Ile Thr Cys Lys Ser Ile Ser Tyr Thr Val Ser Cys Thr
                245                 250                 255
Val Glu Gln Lys Gln Thr Cys Arg Pro Thr Glu Asp Cys Arg Val Gln
            260                 265                 270
Lys Gly Thr Val Leu Cys Glu Cys Pro Trp Asn Gln His Leu Val Gly
    275                 280                 285
Asp Thr Cys Ile Ser Asp Cys Val Asp Lys Lys Cys His Glu Glu Phe
    290                 295                 300
Met Asp Cys Gly Val Tyr Met Asn Arg Gln Ser Cys Tyr Cys Pro Trp
305                 310                 315                 320
Lys Ser Arg Lys Pro Gly Pro Asn Val Asn Ile Asn Glu Cys Leu Leu
                325                 330                 335
Asn Glu Tyr Tyr Tyr Thr Val Ser Phe Thr Pro Asn Ile Ser Phe Asp
                340                 345                 350
Ser Asp His Cys Lys Arg Tyr Glu Asp Arg Val Leu Glu Ala Ile Arg
            355                 360                 365
Thr Ser Ile Gly Lys Glu Val Phe Lys Val Glu Ile Leu Asn Cys Thr
    370                 375                 380
Gln Asp Ile Lys Ala Arg Leu Ile Ala Glu Lys Pro Leu Ser Lys Tyr
```

```
385                        390                        395                        400
Val  Leu  Arg  Lys  Leu  Gln  Ala  Cys  Glu  His  Pro  Ile  Gly  Glu  Trp  Cys
               405                      410                           415

Met  Met  Tyr  Pro  Lys  Leu  Leu  Ile  Lys  Lys  Asn  Ser  Ala  Thr  Glu  Ile
               420                      425                      430

Glu  Glu  Glu  Asn  Leu  Cys  Asp  Ser  Leu  Leu  Lys  Asn  Gln  Glu  Ala  Ala
          435                      440                      445

Tyr  Lys  Gly  Gln  Asn  Lys  Cys  Val  Lys  Val  Asp  Asn  Leu  Phe  Trp  Phe
     450                      455                      460

Gln  Cys  Ala  Asp  Gly  Tyr  Thr  Thr  Tyr  Glu  Met  Thr  Arg  Gly  Arg
465                      470                      475                      480

Leu  Arg  Arg  Ser  Val  Cys  Lys  Ala  Gly  Val  Ser  Cys  Asn  Glu  Asn  Glu
               485                      490                           495

Gln  Leu  Glu  Cys  Ala  Asn  Lys  Gly  Gln  Ile  Cys  Val  Tyr  Glu  Asn  Gly
               500                      505                      510

Lys  Ala  Asn  Cys  Gln  Cys  Pro  Pro  Asp  Thr  Lys  Pro  Gly  Glu  Ile  Gly
               515                      520                      525

Cys  Ile  Glu  Arg  Thr  Thr  Cys  Asn  Pro  Lys  Glu  Ile  Gln  Glu  Cys  Gln
     530                      535                      540

Asp  Lys  Lys  Leu  Glu  Cys  Val  Tyr  Lys  Asn  His  Lys  Ala  Glu  Cys  Lys
545                      550                      555                           560

Cys  Pro  Asp  Asp  His  Glu  Cys  Ser  Arg  Gln  Pro  Ala  Lys  Asp  Ser  Cys
               565                      570                      575

Ser  Glu  Glu  Asp  Asn  Gly  Lys  Cys  Gln  Ser  Ser  Gly  Gln  Arg  Cys  Val
               580                      585                      590

Met  Glu  Asn  Gly  Lys  Ala  Val  Cys  Lys  Glu  Lys  Ser  Glu  Ala  Thr  Thr
          595                      600                      605

Ala  Ala  Thr  Thr  Thr  Thr  Lys  Ala  Lys  Asp  Lys  Asp  Pro  Asp  Pro  Gly
     610                      615                      620

Lys  Ser  Ser  Ala  Ala  Ala  Val  Ser  Ala  Thr  Gly  Leu  Leu  Leu  Leu  Leu
625                      630                      635                           640

Ala  Ala  Thr  Ser  Val  Thr  Val  Ala  Ser  Leu
               645                      650
```

( 2 ) INFORMATION FOR SEQ ID NO:68:

( i ) SEQUENCE CHARACTERISTICS:
        ( A ) LENGTH: 441 base pairs
        ( B ) TYPE: nucleic acid
        ( C ) STRANDEDNESS: double
        ( D ) TOPOLOGY: linear ( v i i ) IMMEDIATE SOURCE:
        ( B ) CLONE: Figure 17

( i x ) FEATURE:
        ( A ) NAME/KEY: CDS
        ( B ) LOCATION: 1..441

( x i ) SEQUENCE DESCRIPTION: SEQ ID NO:68:

```
GCC  CTT  GTT  TTG  GAC  GCG  ATA  AAG  ACC  AGT  ATC  GGA  AGC  GAA  GTT  TCT      48
Ala  Leu  Val  Leu  Asp  Ala  Ile  Lys  Thr  Ser  Ile  Gly  Ser  Glu  Val  Ser
 1                  5                       10                      15

AAA  CTT  GAG  ATA  CTG  AAC  TGC  ACG  CAG  GAT  ATT  AAG  GCA  AGG  CTC  ATA      96
Lys  Leu  Glu  Ile  Leu  Asn  Cys  Thr  Gln  Asp  Ile  Lys  Ala  Arg  Leu  Ile
                    20                      25                      30

GTA  CCG  AAA  CCG  CTA  TCA  AAG  CAC  GTG  CTC  AAG  AAG  CTT  CAA  GCA  TGC     144
Val  Pro  Lys  Pro  Leu  Ser  Lys  His  Val  Leu  Lys  Lys  Leu  Gln  Ala  Cys
          35                      40                      45
```

| | | | | | | | | | | | | | | | | |
|---|---|---|---|---|---|---|---|---|---|---|---|---|---|---|---|---|
| GAG | CAT | CCC | GTC | GGG | GAC | TTG | TGT | ATG | CTG | TAT | CCG | AAG | TTG | CCG | ATC | 192 |
| Glu | His | Pro | Val | Gly | Asp | Leu | Cys | Met | Leu | Tyr | Pro | Lys | Leu | Pro | Ile | |
| | 50 | | | | | 55 | | | | | 60 | | | | | |
| AAG | AAA | AAC | TCT | GCG | ACA | GAA | ATT | GAA | GAA | GAG | AAC | CTT | TGC | GAC | AGC | 240 |
| Lys | Lys | Asn | Ser | Ala | Thr | Glu | Ile | Glu | Glu | Glu | Asn | Leu | Cys | Asp | Ser | |
| 65 | | | | | 70 | | | | | 75 | | | | | 80 | |
| CTC | CTC | AAG | CGT | CAG | GAA | GCT | GCC | TAC | AAG | GGT | CAG | AAC | AAA | TGC | GTC | 288 |
| Leu | Leu | Lys | Arg | Gln | Glu | Ala | Ala | Tyr | Lys | Gly | Gln | Asn | Lys | Cys | Val | |
| | | | | 85 | | | | | 90 | | | | | 95 | | |
| AAG | GTC | GGT | AAC | ATT | TTC | TGG | TTC | CAG | TGC | GCT | GAT | GGT | TAC | AGA | TCA | 336 |
| Lys | Val | Gly | Asn | Ile | Phe | Trp | Phe | Gln | Cys | Ala | Asp | Gly | Tyr | Arg | Ser | |
| | | | 100 | | | | | 105 | | | | | 110 | | | |
| GTT | TAC | GAC | ATC | ACA | CAA | GGT | CGC | CTA | CGC | CGC | TCC | GTG | TGC | GAA | CGT | 384 |
| Val | Tyr | Asp | Ile | Thr | Gln | Gly | Arg | Leu | Arg | Arg | Ser | Val | Cys | Glu | Arg | |
| | | | 115 | | | | | 120 | | | | | 125 | | | |
| GGA | ATT | TCT | TGC | AGT | GAT | AAT | GAA | CAG | TTG | GAG | TGT | GCC | AAG | AAA | GGA | 432 |
| Gly | Ile | Ser | Cys | Ser | Asp | Asn | Glu | Gln | Leu | Glu | Cys | Ala | Lys | Lys | Gly | |
| | | 130 | | | | 135 | | | | | 140 | | | | | |
| CAA | ATA | TGT | | | | | | | | | | | | | | 441 |
| Gln | Ile | Cys | | | | | | | | | | | | | | |
| 145 | | | | | | | | | | | | | | | | |

( 2 ) INFORMATION FOR SEQ ID NO:69:

( i ) SEQUENCE CHARACTERISTICS:
        ( A ) LENGTH: 147 amino acids
        ( B ) TYPE: amino acid
        ( D ) TOPOLOGY: linear ( i i ) MOLECULE TYPE: protein ( x i ) SEQUENCE DESCRIPTION: SEQ ID NO:69:

| | | | | | | | | | | | | | | |
|---|---|---|---|---|---|---|---|---|---|---|---|---|---|---|
| Ala | Leu | Val | Leu | Asp | Ala | Ile | Lys | Thr | Ser | Ile | Gly | Ser | Glu | Val | Ser |
| 1 | | | | 5 | | | | | 10 | | | | | 15 |
| Lys | Leu | Glu | Ile | Leu | Asn | Cys | Thr | Gln | Asp | Ile | Lys | Ala | Arg | Leu | Ile |
| | | | 20 | | | | | 25 | | | | | 30 | | |
| Val | Pro | Lys | Pro | Leu | Ser | Lys | His | Val | Leu | Lys | Lys | Leu | Gln | Ala | Cys |
| | | 35 | | | | | 40 | | | | | 45 | | | |
| Glu | His | Pro | Val | Gly | Asp | Leu | Cys | Met | Leu | Tyr | Pro | Lys | Leu | Pro | Ile |
| | 50 | | | | | 55 | | | | | 60 | | | | |
| Lys | Lys | Asn | Ser | Ala | Thr | Glu | Ile | Glu | Glu | Glu | Asn | Leu | Cys | Asp | Ser |
| 65 | | | | | 70 | | | | | 75 | | | | | 80 |
| Leu | Leu | Lys | Arg | Gln | Glu | Ala | Ala | Tyr | Lys | Gly | Gln | Asn | Lys | Cys | Val |
| | | | | 85 | | | | | 90 | | | | | 95 | |
| Lys | Val | Gly | Asn | Ile | Phe | Trp | Phe | Gln | Cys | Ala | Asp | Gly | Tyr | Arg | Ser |
| | | | 100 | | | | | 105 | | | | | 110 | | |
| Val | Tyr | Asp | Ile | Thr | Gln | Gly | Arg | Leu | Arg | Arg | Ser | Val | Cys | Glu | Arg |
| | | | 115 | | | | | 120 | | | | | 125 | | |
| Gly | Ile | Ser | Cys | Ser | Asp | Asn | Glu | Gln | Leu | Glu | Cys | Ala | Lys | Lys | Gly |
| | | 130 | | | | 135 | | | | | 140 | | | | |
| Gln | Ile | Cys | | | | | | | | | | | | | |
| 145 | | | | | | | | | | | | | | | |

( 2 ) INFORMATION FOR SEQ ID NO:70:

( i ) SEQUENCE CHARACTERISTICS:
        ( A ) LENGTH: 14 amino acids
        ( B ) TYPE: amino acid
        ( D ) TOPOLOGY: linear ( v i i ) IMMEDIATE SOURCE:
        ( B ) CLONE: F9

(xi) SEQUENCE DESCRIPTION: SEQ ID NO:70:

Lys Ala Asn Arg Gln Cys Pro Pro Asp Thr Arg Arg Gly Lys
1               5                   10

(2) INFORMATION FOR SEQ ID NO:71:

(i) SEQUENCE CHARACTERISTICS:
    (A) LENGTH: 14 amino acids
    (B) TYPE: amino acid
    (D) TOPOLOGY: linear (vii) IMMEDIATE SOURCE:
    (B) CLONE: F10

(xi) SEQUENCE DESCRIPTION: SEQ ID NO:71:

Lys Cys Asn Cys Asp Cys Pro Pro Asp Thr Arg Pro Gly Lys
1               5                   10